(12) United States Patent
Kubota et al.

(10) Patent No.: US 12,427,336 B2
(45) Date of Patent: *Sep. 30, 2025

(54) DEVICE FOR PROJECTING IMAGES ON THE RETINA

(71) Applicant: ACUCELA INC., Seattle, WA (US)

(72) Inventors: Ryo Kubota, Seattle, WA (US); Karim Haroud, Villeneuve (CH); Beat Wyss, Niederbipp (CH); Hans Bernhard, Schliern (CH); Jean-Noel Fehr, Neuchâtel (CH); Patrizia Weber, Bern (CH); Moritz Haeberli, Bern (CH); Amitava Gupta, Seattle, WA (US)

(73) Assignee: ACUCELA INC., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/632,487

(22) Filed: Apr. 11, 2024

(65) Prior Publication Data
US 2024/0252835 A1  Aug. 1, 2024

Related U.S. Application Data

(60) Continuation of application No. 18/153,000, filed on Jan. 11, 2023, now Pat. No. 11,986,669, which is a (Continued)

(51) Int. Cl.
*A61N 5/06* (2006.01)
*G02B 27/01* (2006.01)
*G02B 27/30* (2006.01)

(52) U.S. Cl.
CPC ....... *A61N 5/0622* (2013.01); *G02B 27/0172* (2013.01); *G02B 27/30* (2013.01);
(Continued)

(58) Field of Classification Search
CPC ............ A61N 5/0622; A61N 2005/063; A61N 2005/0648; A61N 2005/0652;
(Continued)

(56) References Cited

U.S. PATENT DOCUMENTS

| 2,350,386 | A  | 6/1944 | Christman |
| 6,516,808 | B2 | 2/2003 | Schulman |

(Continued)

FOREIGN PATENT DOCUMENTS

| CN | 101394809 | 3/2009 |
| CN | 103505345 | 1/2014 |

(Continued)

OTHER PUBLICATIONS

Zhou WJ, Zhang YY, Li H, Wu YF, Xu J, Lv S, Li G, Liu SC, Song SF. Five-year progression of refractive errors and incidence of myopia in school-aged children in western China. J Epidemiol. Jul. 5, 2016; 26(7):386-95. Epub Feb. 13, 2016.
(Continued)

*Primary Examiner* — Gary Jackson
*Assistant Examiner* — Sebastian X Lukjan
(74) *Attorney, Agent, or Firm* — FisherBroyles, LLP; John K. Shimmick

(57) ABSTRACT

A device to stimulate the retina comprises one or more light sources coupled to one or more optical elements. The one or more optical elements is configured to illuminate the retina with one or more images at a location away from a fovea of a wearer. In some embodiments, each of the one or more images comprises a depth of focus and a spatial resolution. The one or more images can be formed at a distance anterior to the retina, at a distance posterior to the retina or on the retina. In some embodiments, the depth of focus is less than the distance, and the spatial resolution greater than a spatial resolution of the retina at the location.

19 Claims, 22 Drawing Sheets

Related U.S. Application Data continuation of application No. 17/662,098, filed on May 5, 2022, now Pat. No. 11,583,696, which is a division of application No. 16/947,537, filed on Aug. 5, 2020, now Pat. No. 11,358,001, which is a continuation of application No. PCT/US2020/044571, filed on Jul. 31, 2020.

(60) Provisional application No. 62/925,948, filed on Oct. 25, 2019, provisional application No. 62/907,496, filed on Sep. 27, 2019, provisional application No. 62/885,035, filed on Aug. 9, 2019, provisional application No. 62/881,123, filed on Jul. 31, 2019.

(52) U.S. Cl.
CPC ............. *A61N 2005/063* (2013.01); *A61N 2005/0648* (2013.01); *A61N 2005/0652* (2013.01); *A61N 2005/0663* (2013.01); *G02B 2027/0178* (2013.01)

(58) Field of Classification Search
CPC .... A61N 2005/0663; A61N 2005/0659; A61N 2005/0662; A61N 2005/0626; G02B 27/0172; G02B 27/30; G02B 2027/0178; G02B 27/0093; G02C 7/02; G02C 7/04; G02C 2202/24
See application file for complete search history.

(56) References Cited

U.S. PATENT DOCUMENTS

| | | | |
|---|---|---|---|
| 7,018,040 B2 | 3/2006 | Blum | |
| 8,057,034 B2 | 11/2011 | Ho | |
| 8,246,167 B2 | 8/2012 | Legerton | |
| 8,432,124 B2 | 4/2013 | Foster | |
| 8,662,664 B2 | 3/2014 | Artal Soriano | |
| 8,857,983 B2 | 10/2014 | Pugh | |
| 8,960,899 B2 | 2/2015 | Etzkorn | |
| 9,054,079 B2 | 6/2015 | Etzkorn | |
| 9,176,332 B1 | 11/2015 | Etzkorn | |
| 9,345,813 B2 | 5/2016 | Hogg | |
| 9,482,882 B1 | 11/2016 | Hanover | |
| 9,482,883 B1 | 11/2016 | Meisenholder | |
| 9,726,904 B1 | 8/2017 | Lin | |
| 9,763,827 B2 | 9/2017 | Kelleher | |
| 9,885,884 B2 | 2/2018 | Drobe | |
| 9,889,615 B2 | 2/2018 | Pugh | |
| 9,918,894 B2 | 3/2018 | Lam | |
| 9,962,071 B2 | 5/2018 | Yates | |
| RE47,006 E | 8/2018 | To | |
| 10,133,092 B2 | 11/2018 | Tsubota | |
| 10,139,521 B2 | 11/2018 | Tran | |
| 10,146,067 B2 | 12/2018 | Tsai | |
| 10,231,897 B2 | 3/2019 | Tse | |
| 10,268,050 B2 | 4/2019 | To | |
| 10,288,909 B1 | 5/2019 | Youssef | |
| 10,359,648 B2 | 7/2019 | Kim | |
| 10,591,745 B1 | 3/2020 | Lin | |
| 10,788,686 B2 | 9/2020 | Tsai | |
| 10,884,264 B2 | 1/2021 | Hones | |
| 10,921,612 B2 | 2/2021 | Zhou | |
| 10,993,515 B1 | 5/2021 | Kim | |
| 11,000,186 B2 | 5/2021 | Linder | |
| 11,163,166 B1 | 11/2021 | Ebert | |
| 11,187,921 B2 | 11/2021 | Zhou | |
| 11,219,287 B1 | 1/2022 | Kim | |
| 11,275,259 B2 | 3/2022 | Kubota | |
| 11,281,022 B2 | 3/2022 | Buscemi | |
| 11,320,674 B2 | 5/2022 | Kubota | |
| 11,358,001 B2 | 6/2022 | Kubota | |
| 11,366,339 B2 | 6/2022 | Kubota | |
| 11,366,341 B1 | 6/2022 | Kubota | |
| 11,388,968 B2 | 7/2022 | Dabov | |
| 11,395,959 B2 | 7/2022 | Stemple | |
| 11,402,662 B2 | 8/2022 | Wyss | |
| 11,409,136 B1 | 8/2022 | Kubota | |
| 11,415,818 B2 | 8/2022 | Olgun | |
| 11,444,488 B2 | 9/2022 | Bohn | |
| 11,446,514 B2 | 9/2022 | Bahmani | |
| 11,460,720 B1 | 10/2022 | Kubota | |
| 11,467,423 B2 | 10/2022 | Buscemi | |
| 11,467,426 B2 | 10/2022 | Kubota | |
| 11,467,428 B2 | 10/2022 | Kubota | |
| 11,470,936 B2 | 10/2022 | Kim | |
| 11,480,813 B2 | 10/2022 | Kubota | |
| 11,497,931 B2 | 11/2022 | Buscemi | |
| 11,531,216 B2 | 12/2022 | Kubota | |
| 11,583,696 B2 * | 2/2023 | Kubota | A61N 5/0622 |
| 11,619,831 B2 | 4/2023 | Wyss | |
| 11,624,937 B2 | 4/2023 | Gupta | |
| 11,630,329 B2 | 4/2023 | Kubota | |
| 11,656,483 B2 | 5/2023 | Ice | |
| 11,681,162 B2 | 6/2023 | Zhou | |
| 11,681,164 B2 | 6/2023 | Jamshidi | |
| 11,693,259 B2 | 7/2023 | Buscemi | |
| 11,719,957 B2 | 8/2023 | Kubota | |
| 11,733,545 B2 | 8/2023 | Kubota | |
| 11,777,340 B2 | 10/2023 | Kubota | |
| 11,860,454 B2 | 1/2024 | Kubota | |
| 11,971,615 B2 | 4/2024 | Kubota | |
| 11,986,669 B2 * | 5/2024 | Kubota | G02C 7/04 |
| 12,085,786 B2 | 9/2024 | Buscemi | |
| 12,105,362 B2 | 10/2024 | Kubota | |
| 2002/0186345 A1 | 12/2002 | Duppstadt | |
| 2003/0011745 A1 | 1/2003 | Molebny | |
| 2004/0237971 A1 | 12/2004 | Radhakrishnan | |
| 2004/0246441 A1 | 12/2004 | Stark | |
| 2004/0257529 A1 | 12/2004 | Thomas | |
| 2005/0258053 A1 | 11/2005 | Sieg | |
| 2006/0082729 A1 | 4/2006 | To | |
| 2006/0227067 A1 | 10/2006 | Iwasaki | |
| 2007/0002452 A1 | 1/2007 | Munro | |
| 2007/0076217 A1 | 4/2007 | Baker | |
| 2007/0115431 A1 | 5/2007 | Smith | |
| 2007/0127349 A1 | 6/2007 | Hotta | |
| 2007/0153231 A1 | 7/2007 | Iuliano | |
| 2007/0281752 A1 | 12/2007 | Lewis | |
| 2008/0231799 A1 | 9/2008 | Iuliano | |
| 2008/0231801 A1 | 9/2008 | Iuliano | |
| 2008/0291391 A1 | 11/2008 | Meyers | |
| 2008/0309882 A1 | 12/2008 | Thorn | |
| 2009/0002631 A1 | 1/2009 | Campbell | |
| 2009/0187242 A1 | 7/2009 | Weeber | |
| 2009/0201460 A1 | 8/2009 | Blum | |
| 2009/0204207 A1 | 8/2009 | Blum | |
| 2010/0076417 A1 | 3/2010 | Suckewer | |
| 2010/0294675 A1 | 11/2010 | Mangano | |
| 2010/0296058 A1 | 11/2010 | Ho | |
| 2011/0085129 A1 | 4/2011 | Legerton | |
| 2011/0153012 A1 | 6/2011 | Legerton | |
| 2011/0157554 A1 | 6/2011 | Kawai | |
| 2011/0202114 A1 | 8/2011 | Kessel | |
| 2012/0055817 A1 | 3/2012 | Newman | |
| 2012/0062836 A1 | 3/2012 | Tse | |
| 2012/0199995 A1 | 8/2012 | Pugh | |
| 2012/0206485 A1 | 8/2012 | Osterhout | |
| 2012/0212399 A1 | 8/2012 | Border | |
| 2012/0215291 A1 | 8/2012 | Pugh | |
| 2013/0027655 A1 | 1/2013 | Blum | |
| 2013/0072828 A1 | 3/2013 | Sweis | |
| 2013/0135578 A1 | 5/2013 | Pugh | |
| 2013/0194540 A1 | 8/2013 | Pugh | |
| 2013/0278887 A1 | 10/2013 | Legerton | |
| 2013/0317487 A1 | 11/2013 | Luttrull | |
| 2013/0342808 A1 | 12/2013 | Hong | |
| 2014/0039048 A1 | 2/2014 | Olof | |
| 2014/0039361 A1 | 2/2014 | Siu | |
| 2014/0085601 A1 | 3/2014 | Etzkorn | |
| 2014/0194773 A1 | 7/2014 | Pletcher | |
| 2014/0218647 A1 | 8/2014 | Blum | |
| 2014/0240665 A1 | 8/2014 | Pugh | |
| 2014/0268029 A1 | 9/2014 | Pugh | |

(56) References Cited

U.S. PATENT DOCUMENTS

| | | |
|---|---|---|
| 2014/0277291 A1 | 9/2014 | Pugh |
| 2014/0306361 A1 | 10/2014 | Pugh |
| 2014/0379054 A1 | 12/2014 | Cooper |
| 2015/0018599 A1 | 1/2015 | Legerton |
| 2015/0057701 A1 | 2/2015 | Kelleher |
| 2015/0084584 A1 | 3/2015 | Monks |
| 2015/0109574 A1 | 4/2015 | Tse |
| 2015/0160477 A1 | 6/2015 | Dai |
| 2015/0200554 A1 | 7/2015 | Marks |
| 2015/0241706 A1 | 8/2015 | Schowengerdt |
| 2016/0016004 A1 | 1/2016 | Hudson |
| 2016/0056498 A1 | 2/2016 | Flitsch |
| 2016/0067037 A1 | 3/2016 | Rosen |
| 2016/0067087 A1 | 3/2016 | Tedford |
| 2016/0070105 A1 | 3/2016 | Tannoudiji |
| 2016/0091737 A1 | 3/2016 | Kim |
| 2016/0143801 A1 | 5/2016 | Lam |
| 2016/0158486 A1 | 6/2016 | Colbaugh |
| 2016/0212404 A1 | 7/2016 | Maiello |
| 2016/0270656 A1* | 9/2016 | Samec ............... A61B 3/1015 |
| 2016/0299357 A1 | 10/2016 | Hayashi |
| 2016/0377884 A1 | 12/2016 | Lau |
| 2017/0000326 A1 | 1/2017 | Samec |
| 2017/0001032 A1 | 1/2017 | Samec |
| 2017/0010480 A1 | 1/2017 | Blum |
| 2017/0014074 A1 | 1/2017 | Etzkorn |
| 2017/0055823 A1 | 3/2017 | Lu |
| 2017/0072218 A1 | 3/2017 | Rucker |
| 2017/0078623 A1 | 3/2017 | Hilkes |
| 2017/0097519 A1 | 4/2017 | Lee |
| 2017/0115512 A1 | 4/2017 | Pugh |
| 2017/0131567 A1 | 5/2017 | To |
| 2017/0184875 A1 | 6/2017 | Newman |
| 2017/0229730 A1 | 8/2017 | Flitsch |
| 2017/0236255 A1 | 8/2017 | Wetzstein |
| 2017/0270636 A1 | 9/2017 | Shtukater |
| 2017/0276963 A1 | 9/2017 | Brennan |
| 2017/0307779 A1 | 10/2017 | Marullo |
| 2017/0367879 A1 | 12/2017 | Lopath |
| 2018/0017810 A1 | 1/2018 | Wu |
| 2018/0017814 A1* | 1/2018 | Tuan ..................... A61B 3/107 |
| 2018/0052319 A1 | 2/2018 | Mccabe |
| 2018/0055351 A1 | 3/2018 | Yates |
| 2018/0074322 A1 | 3/2018 | Rousseau |
| 2018/0090958 A1 | 3/2018 | Steger |
| 2018/0092738 A1 | 4/2018 | Tai |
| 2018/0136486 A1 | 5/2018 | Macnamara |
| 2018/0136491 A1 | 5/2018 | Ashwood |
| 2018/0161231 A1 | 6/2018 | Tse |
| 2018/0173010 A1 | 6/2018 | Harant |
| 2018/0188556 A1 | 7/2018 | Portney |
| 2018/0221140 A1* | 8/2018 | Rosen .................. A61F 2/1613 |
| 2018/0264284 A1 | 9/2018 | Alvarez |
| 2018/0275427 A1 | 9/2018 | Lau |
| 2018/0345034 A1 | 12/2018 | Butzloff |
| 2019/0033618 A1 | 1/2019 | Choi |
| 2019/0033619 A1* | 1/2019 | Neitz ....................... G02C 7/02 |
| 2019/0038123 A1 | 2/2019 | Linder |
| 2019/0049730 A1 | 2/2019 | Miller |
| 2019/0076241 A1 | 3/2019 | Alarcon Heredia |
| 2019/0092545 A1 | 3/2019 | Oag |
| 2019/0107734 A1 | 4/2019 | Lee |
| 2019/0113757 A1 | 4/2019 | Van Heugten |
| 2019/0129204 A1 | 5/2019 | Tsubota |
| 2019/0227342 A1 | 7/2019 | Brennan |
| 2019/0235279 A1 | 8/2019 | Hones |
| 2019/0247675 A1 | 8/2019 | Legerton |
| 2019/0250413 A1 | 8/2019 | Martin |
| 2019/0250432 A1 | 8/2019 | Kim |
| 2019/0314147 A1 | 10/2019 | Blum |
| 2019/0318589 A1 | 10/2019 | Howell |
| 2020/0026082 A1 | 1/2020 | Park |
| 2020/0033637 A1 | 1/2020 | Jamshidi |
| 2020/0073148 A1 | 3/2020 | Alhaideri |
| 2020/0089023 A1 | 3/2020 | Zhou |
| 2020/0108272 A1 | 4/2020 | Bahmani |
| 2020/0110265 A1 | 4/2020 | Serdarevic |
| 2020/0133024 A1 | 4/2020 | Paune Fabre |
| 2020/0133030 A1 | 4/2020 | Eriksson |
| 2020/0142219 A1 | 5/2020 | Rousseau |
| 2020/0183169 A1 | 6/2020 | Peng |
| 2020/0264455 A1 | 8/2020 | Olgun |
| 2020/0360184 A1 | 11/2020 | Xiao |
| 2020/0364992 A1 | 11/2020 | Howell |
| 2021/0018762 A1 | 1/2021 | Zheleznyak |
| 2021/0031051 A1 | 2/2021 | Kubota |
| 2021/0048690 A1 | 2/2021 | Guillot |
| 2021/0069524 A1 | 3/2021 | Kubota |
| 2021/0231977 A1 | 7/2021 | Zhou |
| 2021/0263336 A1 | 8/2021 | Gupta |
| 2021/0298440 A1 | 9/2021 | Kim |
| 2021/0329764 A1 | 10/2021 | Linder |
| 2021/0356767 A1 | 11/2021 | Kubota |
| 2021/0376661 A1 | 12/2021 | Bohn |
| 2021/0379399 A1 | 12/2021 | Buscemi |
| 2021/0382325 A1 | 12/2021 | Kubota |
| 2021/0382326 A1 | 12/2021 | Kubota |
| 2021/0389607 A1 | 12/2021 | Buscemi |
| 2022/0057651 A1 | 2/2022 | Segre |
| 2022/0107508 A1 | 4/2022 | Zhou |
| 2022/0128842 A1 | 4/2022 | Ice |
| 2022/0179213 A1 | 6/2022 | Zhou |
| 2022/0197059 A1 | 6/2022 | Zhou |
| 2022/0231523 A1 | 7/2022 | Bristol |
| 2022/0257972 A1 | 8/2022 | Kubota |
| 2022/0299795 A1 | 9/2022 | Wyss |
| 2022/0390766 A1 | 12/2022 | Kubota |
| 2022/0390768 A1 | 12/2022 | Kubota |
| 2022/0397775 A1 | 12/2022 | Bahmani |
| 2022/0404641 A1 | 12/2022 | Kubota |
| 2022/0413318 A1 | 12/2022 | Kubota |
| 2023/0026567 A1 | 1/2023 | Buscemi |
| 2023/0089006 A1 | 3/2023 | Kubota |
| 2023/0291244 A1 | 9/2023 | Kasar |
| 2023/0324717 A1 | 10/2023 | Kubota |

FOREIGN PATENT DOCUMENTS

| | | | |
|---|---|---|---|
| CN | 204422891 | 6/2015 | |
| CN | 104749791 | 7/2015 | |
| CN | 108957788 | 12/2018 | |
| CN | 109445127 | 3/2019 | |
| CN | 109633925 | 4/2019 | |
| CN | 215494397 | 1/2022 | |
| EP | 3153139 | 4/2017 | |
| EP | 3232254 | 10/2017 | |
| EP | 3255478 | 12/2017 | |
| EP | 3413116 | 12/2018 | |
| EP | 3553594 | 10/2019 | |
| EP | 3640713 | 4/2020 | |
| EP | 4167022 | 4/2023 | |
| JP | H0650031 U | 7/1994 | |
| JP | 2006292883 | 10/2006 | |
| JP | 2007313313 | 12/2007 | |
| JP | 2011518355 | 6/2011 | |
| JP | 2014508585 | 4/2014 | |
| JP | 2017510851 | 4/2017 | |
| JP | 2017173847 | 9/2017 | |
| JP | 2017219847 | 12/2017 | |
| JP | 2019529968 | 10/2019 | |
| KR | 20180038359 A | 4/2018 | |
| TW | M356929 | 5/2009 | |
| TW | 201234072 | 8/2012 | |
| TW | 201621403 | 6/2016 | |
| TW | 201734580 | 10/2017 | |
| WO | 2009074638 A3 | 6/2009 | |
| WO | 2009121810 | 10/2009 | |
| WO | 2009129528 | 10/2009 | |
| WO | WO-2010015255 A1 * | 2/2010 | ............. A61F 9/008 |
| WO | 2010043599 | 4/2010 | |
| WO | 2011008846 | 1/2011 | |
| WO | 2011089042 | 7/2011 | |
| WO | 2011153158 | 12/2011 | |
| WO | 2011163559 | 12/2011 | |

(56) References Cited

FOREIGN PATENT DOCUMENTS

| | | |
|---|---|---|
| WO | 2012018583 | 2/2012 |
| WO | 2012036638 | 3/2012 |
| WO | 2012037019 | 3/2012 |
| WO | 2012106542 | 8/2012 |
| WO | 2012118777 | 9/2012 |
| WO | 2012129210 | 9/2012 |
| WO | 2012136470 | 10/2012 |
| WO | 2012138426 | 10/2012 |
| WO | 2013059195 | 4/2013 |
| WO | 2013059656 | 4/2013 |
| WO | 2013059663 | 4/2013 |
| WO | 2013087518 | 6/2013 |
| WO | 2013112748 | 8/2013 |
| WO | 2013112803 | 8/2013 |
| WO | 2013112862 | 8/2013 |
| WO | 2013112868 | 8/2013 |
| WO | 2013130803 | 9/2013 |
| WO | 2013151728 | 10/2013 |
| WO | 2013158418 | 10/2013 |
| WO | 2014004836 | 1/2014 |
| WO | 2014004839 | 1/2014 |
| WO | 2014018104 | 1/2014 |
| WO | 2014033035 | 3/2014 |
| WO | 2014050879 | 4/2014 |
| WO | 2014052012 | 4/2014 |
| WO | 2014117173 | 7/2014 |
| WO | 2014120928 | 8/2014 |
| WO | 2014161002 | 10/2014 |
| WO | 2014178221 | 11/2014 |
| WO | 2014191460 | 12/2014 |
| WO | 2015063097 | 5/2015 |
| WO | 2015095891 | 6/2015 |
| WO | 2015105881 | 7/2015 |
| WO | 2015164564 | 10/2015 |
| WO | 2015186723 | 12/2015 |
| WO | 2015192117 | 12/2015 |
| WO | 2016019346 | 2/2016 |
| WO | 2016019351 | 2/2016 |
| WO | 2016019359 | 2/2016 |
| WO | 2017039672 | 3/2017 |
| WO | 2017083770 | 5/2017 |
| WO | 2017083771 | 5/2017 |
| WO | 2017083774 | 5/2017 |
| WO | 2017094886 | 6/2017 |
| WO | 2017097708 | 6/2017 |
| WO | 2017168122 | 10/2017 |
| WO | 2018014712 | 1/2018 |
| WO | 2018014712 A1 | 1/2018 |
| WO | 2018014960 | 1/2018 |
| WO | 2018057804 | 3/2018 |
| WO | 2018058130 | 3/2018 |
| WO | 2018075229 | 4/2018 |
| WO | 2018085576 | 5/2018 |
| WO | 2018088980 | 5/2018 |
| WO | 2018089699 | 5/2018 |
| WO | 2018208724 | 11/2018 |
| WO | 2019100941 | 5/2019 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020025355 | 2/2020 |
| WO | 2020028177 | 2/2020 |
| WO | 20200028177 | 2/2020 |
| WO | 2020045567 | 3/2020 |
| WO | 2020069232 | 4/2020 |
| WO | 2020069232 A1 | 4/2020 |
| WO | 2020219518 | 10/2020 |
| WO | 2021022193 | 2/2021 |
| WO | 2021056018 | 3/2021 |
| WO | 2021116449 A1 | 6/2021 |
| WO | 2021168481 | 8/2021 |
| WO | 2021174290 | 9/2021 |
| WO | 2021231684 | 11/2021 |
| WO | 2021252318 | 12/2021 |
| WO | 2021252319 | 12/2021 |
| WO | 2021252320 | 12/2021 |
| WO | 2022217193 | 10/2022 |
| WO | 2022258572 A1 | 12/2022 |

OTHER PUBLICATIONS

"Design Considerations for Overmolding and Insert Molding," Proto Labs, retrieved May 6, 2024 from chrome-extension://efaidnbmnnnibpcajpcglclefindmkaj/https://vertassets.blob.core.windows.net/download/777c536d/777c536d-f935-4a3a-aa9e-bff37143c1dd/pl_designconsiderations_for_om_im_wp_final.pdf, applicant believes that the teachings of this reference was known prior to Apr. 6, 2021.

"What Is Insert Molding? Process, Considerations & Applications," retrieved May 6, 2024 from https://www.rapiddirect.com/blog/what-is-insert-molding/, applicant believes that the teachings of these reference was known prior to Apr. 6, 2021.

Adler, Daniel, et al., "The possible effect of under correction on myopic progression in children," Clin Exp Optom., 89:315-321 (2006).

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al, "Regression of early diabetic macular edema is associated with prevention of dark adaptation", in Eye, (2011). 25, pp. 1546-1554.

Benavente-Perez, A., et al., "Axial Eye Growth and Refractive Error Development Can Be Modified by Exposing the Peripheral Retina to Relative Myopic or Hyperopic Defocus," Invest Ophthalmol Vis Sci., 55:6765-6773 (2014).

Bonar, JR, et al, "High brightness low power consumption microLED arrays", in SPIE DigitalLibrary.org/conference-proceedings-of-spie, SPIE OPTO, 2016, San Francisco, California, United States, Abstract Only.

Brennan NA, Toubouti YM, Cheng X, Bullimore MA. Efficacy in myopia control. Prog Retin Eye Res. Jul. 2021; 83:100923. Epub Nov. 27, 2020.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cook, Colin A., et al., "Phototherapeutic Contact Lens for Diabetic Retinopahty," 2018 IEEE Micro Electro Mechanical Systems, pp. 62-65, XP033335512, (Jan. 21, 2018).

Cooper, J., et al, "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al, "Integrated parabolic microlenses on micro LED color pixels", in Nanotechnology, (2018); 29, 16, pp. 1018, Abstract Only.

Dolgin, Elie, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31(6):622-660 (2012).

(56) References Cited

OTHER PUBLICATIONS

Garner, L.F., et al., "Crystalline Lens Power in Myopia," Optometry and Vision Science, 69:863-865 (1992).
Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).
Gwiazda, Jane, et al, "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).
Haglund, Erik, et al., "Multi-wavelength VCSEL arrays using high-contrast gratings," Proc. of SPIE vol. 10113, 7 pages (2017).
Hammond, D.S., et al, "Dynamics of active emmetropisation in young chicks—influence of sign and magnitude of imposed defocus" Ophthalmic Physiol Opt. 33:215-222 (2013).
Henry W., "MicroLED Sources enable diverse ultra-low power applications", in Photonic Spectra, 2013.
International Search Report and Written Opinion for International Application No. PCT/US2020/044571, 17 pages (Nov. 19, 2020).
Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).
Jones, D., "Measure Axial Length to Guide Myopia Management," Review of Myopia Management, 5 pages (Apr. 9, 2020).
Kur, Joanna, et al., "Light adaptation does not prevent early retinal abnormalities in diabetic rats," Scientific Reports, 8 pages (Feb. 8, 2016).
Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).
Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).
Leo, Seo-Wei, et al., "An evidence-based update on myopia and interventions to retard its progression," J AAPOS, 15(2):181-189 (Apr. 2011).
Lingley, A.R., et al, : A single pixel wireless contact lens display, in J Micromech. Microeng., 2011; 21, 125014; doi:10.1088/0960-1317/21/12/125014, Abstract Only.
Martin, J.A., et al., "Predicting and Assessing Visual Performance with Multizone Bifocal Contact Lenses," Optom Vis Sci, 80(12):812-819 (2003).
Matkovic, K., et al., "Global Contrast Factor—a New Approach to Image Contrast," Computational Aesthetics in Graphics, Visualization and Imaging, 9 pages (2005).
McKeague C, et al. "Low-level night-time light therapy for age-related macular degeneration (ALight): study protocol for a randomized controlled trial", in Trials 2014, 15:246, http://www.trialsjournal.com/content/15/1/246.
Moreno, I, "Creating a desired lighting pattern with an LED array" in Aug. 2008, Proceedings of SPIE—The International Society for Optical Engineering 7058, DOI: 10.1117/12.795673.
Moreno, I., "Modeling the radiation pattern of LEDS", in Optics Express, 2008; 16, 3 pp. 1808.
Nickla, Debora L., et al., "Brief hyperopic defocus or form deprivation have varying effects on eye growth and ocular rhythms depending on the time-of-day of exposure," Exp Eye Res. 161:132-142 (Aug. 2017).
Ramsey, DJ, and Arden, GB, "Hypoxia and dark adaptation in diabetic retinopathy: Interactions, consequences and therapy", in Microvascular Complications—Retinopathy (JK Sun, ed.), Cur Dab Rep (2015) 15: 118, DOI 10.1007/s11892-015-0686-2, Abstract Only.
Read, Scott A., et al., "Choroidal changes in human myopia: insights from optical coherence tomography imaging," Clin Exp Optom, 16 pages (2018).
Read, Scott A., et al., "Human Optical Axial Length and Defocus," IOVS, 51(12):6262-6269 (2010).
Shivaprasad, S, et al, "Clinical efficacy and safety of a light mask for prevention of dark adaptation in treating and preventing progression of early diabetic macular oedema at 24 months (CLEOPATRA): a multicentre, phase 3, randomised controlled trial," in www.thelancet.com/diabetes-endocrinology vol. 6, pp. 382-391 ( May 2018).
Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).
Srinivasan, S., "Ocular axes and angles: Time for better understanding," J. Cataract Refract. Surg., 42:351-352 (Mar. 2016).
Torii, Hidemasa, et al., "Violet Light Exposure Can Be a Preventive Strategy Against Myopia Progression," EBioMedicine 15:210-219 (2017).
Walline JJ, Lindsley K, Vedula SS, Cotter SA, Mutti DO, Twelker JD. Interventions to slow progression of myopia in children. Cochran Database Syst Rev. Dec. 7, 2011; (12):CD004916.
Wallman, Josh, et al., "Homeostasis of Eye Growth and the Question of Myopia," Neuron, 43:447-468 (2004).
Wolffsohn, James A., et al., "Impact of Soft Contact Lens Edge Design and Midperipheral Lens Shape on the Epithelium and Its Indentation With Lens Mobility," IOVS, 54(9):6190-6196 (2013).
Legge, Gordon E., et al., "Tolerance to visual defocus," Journal of the Optical Society of America A, [Online] vol. 4, No. 5, May 1, 1987 (May 1, 1987), pp. 851-863, XP093207061.

\* cited by examiner

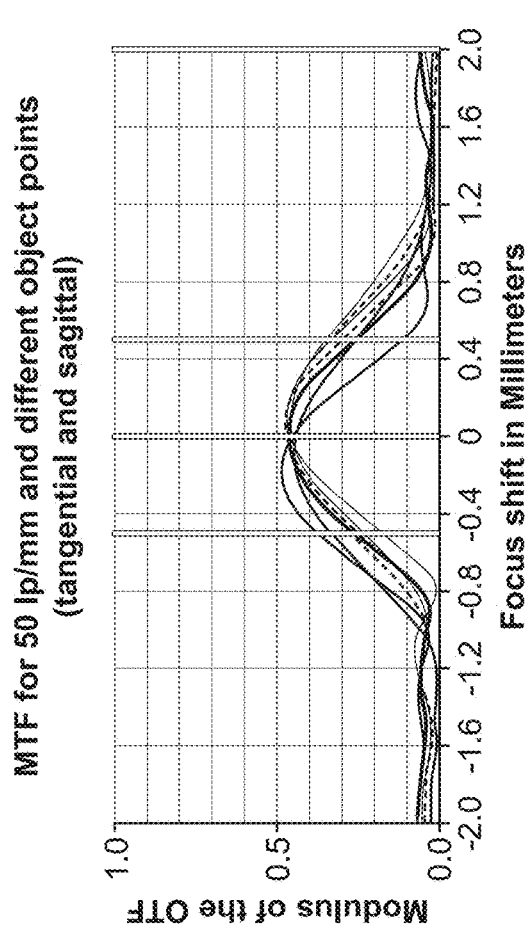
FIG. 7
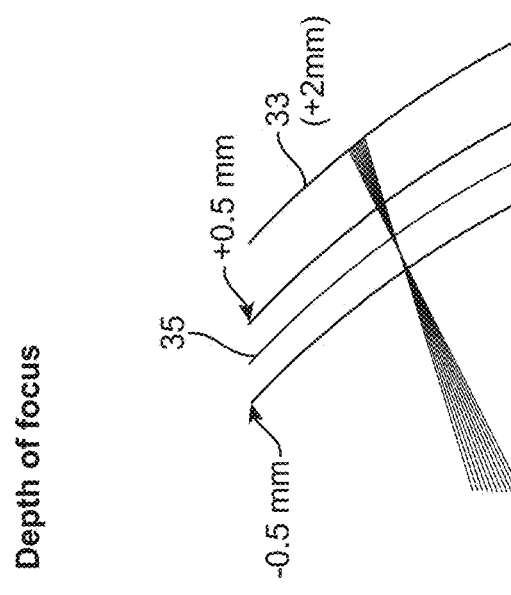
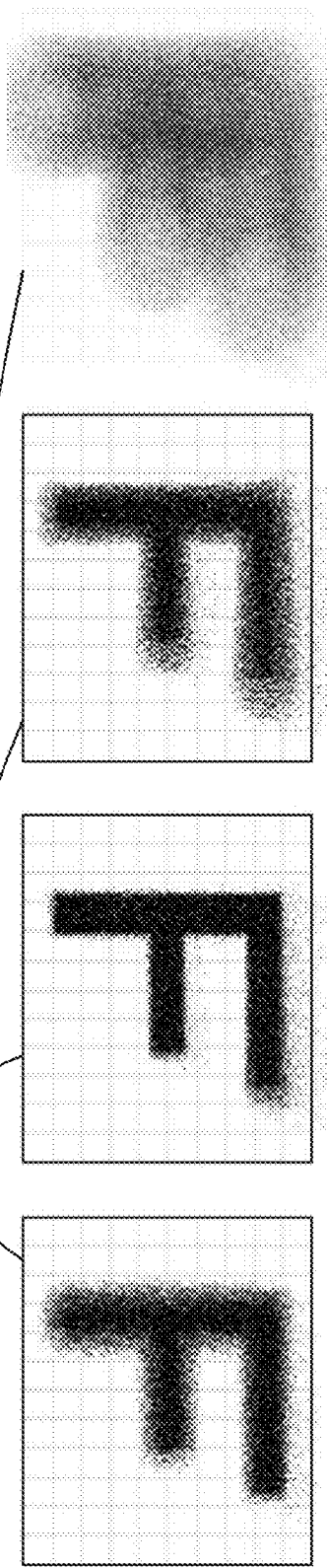
FIG. 6

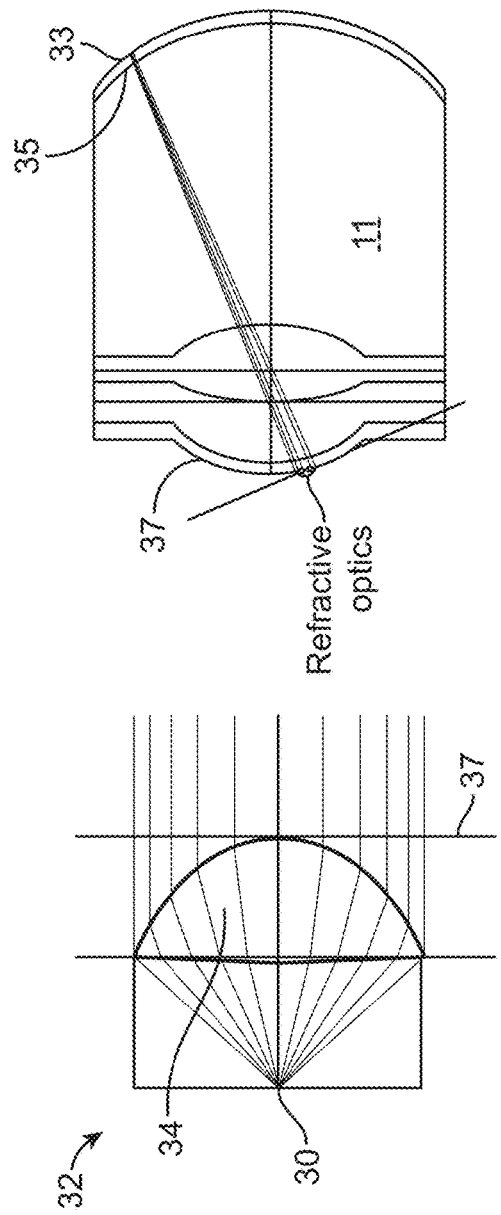
FIG. 8A
FIG. 8B
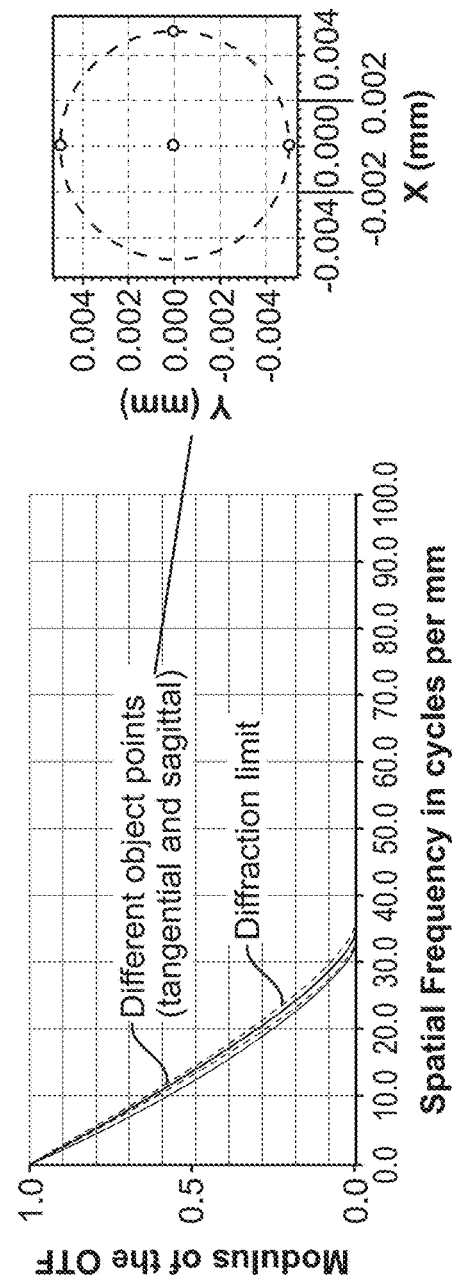
FIG. 9

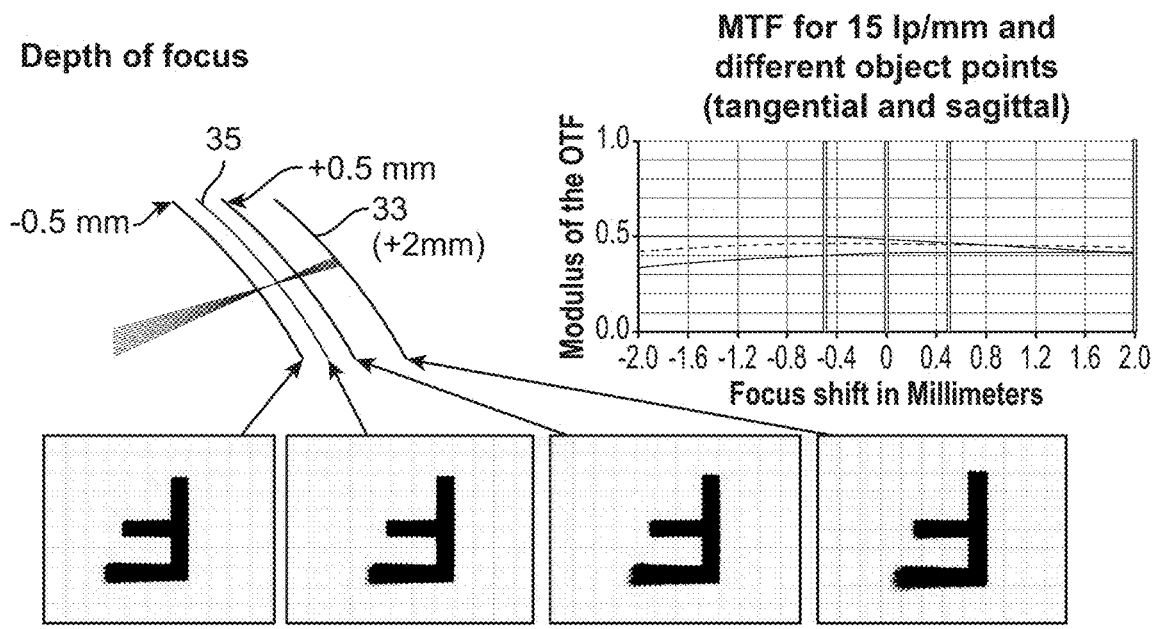
FIG. 10
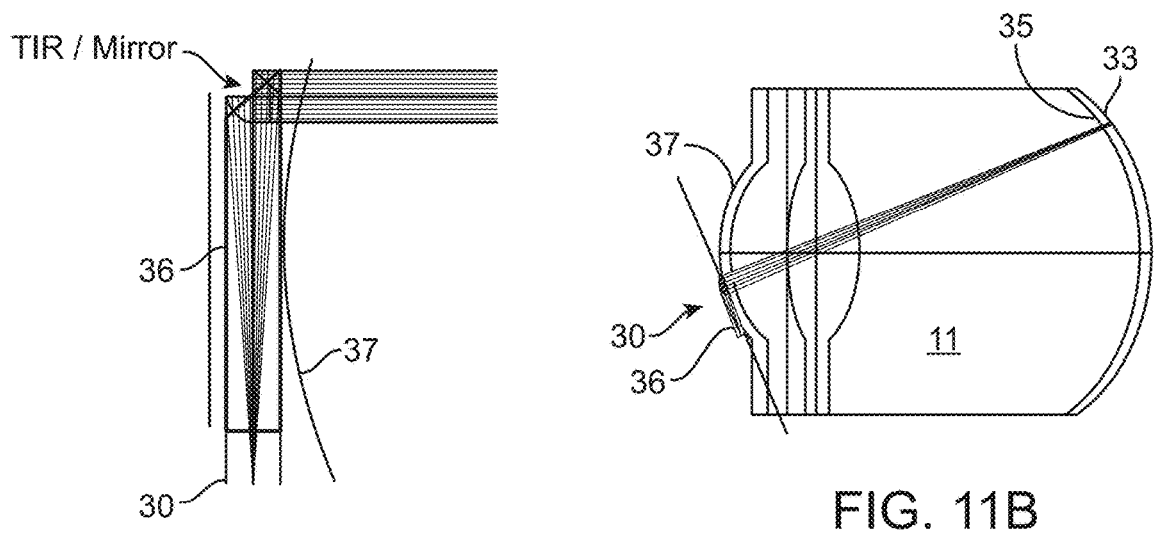
FIG. 11A
FIG. 11B

DEVICE FOR PROJECTING IMAGES ON THE RETINA

RELATED APPLICATIONS

This application is a continuation of U.S. patent application Ser. No. 18/153,000, filed Jan. 11, 2023, now U.S. Pat. No. 11,986,669, issued May 21, 2024, which is a continuation of U.S. patent application Ser. No. 17/662,098, filed May 5, 2022, now U.S. Pat. No. 11,583,696, issued Feb. 21, 2023, which is a divisional of U.S. patent application Ser. No. 16/947,537, filed Aug. 5, 2020, now U.S. Pat. No. 11,358,001, issued Jun. 14, 2022, which is a bypass continuation of International Application No. PCT/US2020/044571, filed Jul. 31, 2020, published as WO 2021/022193 on Feb. 4, 2021, which claims the benefit under 35 U.S.C. § 119 (e) of U.S. Provisional Patent Application No. 62/925,948, filed Oct. 25, 2019, of U.S. Provisional Patent Application No. 62/907,496, filed Sep. 27, 2019, of U.S. Provisional Patent Application No. 62/885,035, filed Aug. 9, 2019, and of U.S. Provisional Patent Application No. 62/881,123, filed Jul. 31, 2019, the entire disclosures of which are incorporated herein by reference.

BACKGROUND

Myopia, or near-sightedness, is a refractive error in which far objects are focused anterior to the retina. This can be related to the axial length of the eye. In general, a 1.0 mm increase in axial length of the eye corresponds to an increase in myopia of 2.5 Diopters ("D").

Spectacle lenses, contact lenses and refractive surgery can be used to treat refractive errors of the eye such as myopia. Although these approaches can be effective in treating myopia, the eye may continue to grow axially, such that the amount of myopia continues to increase. The relatively high prevalence of myopia has prompted studies to understand the underlying mechanisms of axial growth and the development of possible treatment directed to axial growth.

While myopia is known to have genetic causes, the dramatic increase in the incidence of myopia cannot be explained by genetic factors alone; rather, they must be interpreted simply as the remarkable ability of the visual system to adapt to altered environmental conditions, specifically a shift in visual habits from long to short distances and from open to enclosed spaces.

It is known that the retina of many species, including human beings responds to defocused images and grows in order to minimize the blur caused by the defocus. The mechanism of the generation of the growth signal is still under study, but the one of the observable phenomena of the response of retinal tissue to the growth signal is the change in thickness of the choroid. A myopically defocused image can cause the choroid to grow thicker, thus effectively shortening the axial length of the eye, while a hyperopically defocused image can cause the choroid to grow thinner, leading to an increase in axial length. Work in relation to the present disclosure suggests that the change in axial length caused by retinal response to a hyperopic blur or defocus can contribute to myopia development.

While the defocus of images can play a role in choroidal thickness and changes in the axial length of the eye, the prior methods and apparatus are less than ideally suited to address changes in retinal thickness and axial length of the eye. For example, pharmaceutical treatments have been proposed to treat myopia associated with axial length growth, these treatments can have less than ideal results in at least some instances. While atropine and other muscarinic agents can slow myopia progression, possible concerns about post treatment rebound effects and the short and long-term side effects associated with prolonged treatment may have discouraged the widespread use of these drugs.

Although animal studies have demonstrated that refractive development and axial growth can be regulated by visual feedback associated with the eye's effective refractive status, the methods and apparatus used in these animal studies are less than ideally suited for the treatment of myopia in humans.

Work in relation to the present disclosure suggests that the retinal shell becomes more aspheric as the eye becomes more myopic. Examples of image shells on the retina with myopic eyes and traditional correction are described in Cooper, J, "A Review of Current Concepts of the Etiology and Treatment of Myopia" in Eye & Contact Lens, 2018; 44: pp 231. With traditional spherical lenses, the peripheral aspheric retina of the myopic eye receives light focused behind the retina while light is focused at the center of the retina, which can trigger a growth signal because the peripheral light is focused behind the retina, similarly to an eye with insufficient axial length. A conventional spherical or toric lens (e.g. a contact lens or a spectacle lens) generally cannot generate an image shell that matches the optimum shape required for refractive correction that would stop the growth signal to the retina to become even more myopic. One approach has been to provide an aspheric lens that focuses light onto the peripheral regions of the aspheric retina.

Previous refractive correction devices to prevent myopia progression may produce less than ideal results in at least some instances. The refractive correction to provide appropriate focus at the peripheral retina can require a highly aspheric image shell, that can be created by a highly aspheric optic. Unfortunately, such an aspheric optic can generate a central image with a substantial aberration, compromising far vision and reducing quality of vision of the wearer in at least some instances. One approach has been to limit the amount of asphericity to about 2 D or less in order to provide distance vision without significant aberrations to central vision, but this limitation on the amount of asphericity can also limit the amount of correction to peripheral portions of the retina, which can lead to a less than ideal treatment in some instances.

A second approach adopted by some prior art devices is to provide a bifocal or multifocal optic, comprising a central optical zone dedicated to correction of refractive error only, while the peripheral zones generally have more plus power to form a myopically defocused image on the peripheral retina. Ray tracing analyses show that these bifocal optics can create one or more foci at the fovea, compromising the image quality at the fovea.

Studies in animal models as well as clinical studies have suggested that the retina can distinguish a "plus blur" from a "minus blur", or image blur caused by a myopic defocus from a hyperopic defocus, possibly by utilizing longitudinal chromatic aberration as a guide, since the sign of the longitudinal chromatic aberration will be opposite, depending on whether the image blur is hyperopic or myopic. However, prior clinical approaches may not have adequately addressed chromatic aberration to decrease myopia progression in at least some instances.

Therefore, new approaches are needed to treat refractive error of the eye and promote changes to axial length of the eye and choroidal thickness that ameliorate at least some of the limitations of the prior approaches.

SUMMARY

In some embodiments, a device to stimulate to the retina is configured to project one or more images on the retina that falls outside the fovea. The stimulation can be configured to promote a change in the axial length and/or choroidal thickness of the eye. The projected image may comprise a still image or a dynamic image, for example with a refresh rate in the range from 1 Hz to 500 Hz. The light may comprise monochromatic or polychromatic light within a range from 400 nm to 800 nm. The one or more images can be configured in many ways with an image structure corresponding to information or content of the image associated with spatial frequencies. In some embodiments, the one or more images comprises a spatial frequency within a range from 1 cycle per degree to 180 cycles per degree or from 1 cycle per degree to 30 cycles per degree or from 1 cycle per degree to 10 cycles per degree, and a contrast within a range 99.9% to 2.5%, for example. The projected image can be projected on to the retina with an eccentricity in relation to the fovea, and the eccentricity can be within a range from 5 degrees to 40 degrees. The projected image may cover the whole retina within the specified range of eccentricity, for example with an annular pattern, or the projected image may cover a portion of the retina within the range of eccentricity. The stimulation may be continuous or periodic or aperiodic. When periodic, the stimulation may persist for a duration within a range 1 sec to 24 hours. The stimulation may be applied in many ways, for example when the subject is awake or asleep and combinations thereof. The retinal stimulation may be applied using a light projection system. The light projection system can be configured in many ways and is suitable for combination with one or more of many devices. The projection optics as described herein can be integrated into one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens. For example, the projection optics can be combined with a combination of these devices.

In some embodiments, a device to simulate the retina comprises a light source and optics to form an image in front of the retina, behind the retina or on the retina with one or more of an appropriate resolution, depth of focus or diffraction. The image formed on a region of the retina may comprise a resolution finer than the resolution of the retina at the region, such as the highest resolution of the retina at the region. The light beam can be directed to the region of the retina at an angle relative to the optical axis of the eye, so as to illuminate an outer portion of the retina away from the fovea with a resolution finer than the corresponding location of the retina. The depth of focus can be configured to illuminate the retina with an appropriate amount of blurring of the image on the retina, and the diffraction of the spot can be appropriately sized to provide resolution of the image formed in front of the retina finer than the resolution of the retina.

In accordance with some embodiments, a device to stimulate the retina comprises micro-displays located away from a center of a lens and toward a periphery of the lens, in which each of the micro-displays is coupled to a micro-lens array located posteriorly to the micro-display. The micro-displays may comprise an OLED (organic light emitting diode) or an array of micro-LEDs. The micro-lens arrays can be optically coupled with the displays to efficiently collect light from the micro-displays, and substantially collimate the light and/or converge the light before projecting the light into the entrance pupil. The images created by these displays can be myopically or hyperopically defocused and placed symmetrically in a plurality of regions on the retina, such as four sectors (nasal-inferior, nasal-superior, temporal-inferior and temporal-superior). The micro displays can be located away from the optical center of the lens by a distance within a range from 1.5 mm to 4.0 mm, such as 2.5 mm to 3.5 mm. The central optical zone 14 of the lens can be configured to provide emmetropic vision for the wearer, and may have a diameter within a range 3.0 to 5.0 mm. Each micro-display can generate a retinal image with an appropriate shape, such as circular or arcuate and at an angle of about 20 to 60 degrees with respect to the fovea. In some embodiments, the retinal images are formed at the peripheral retina at an eccentricity in the range of 7.5 degrees to about 45 degrees or 15 degrees to about 45 degrees or 15 degrees to 40 degrees, for example within a range from 15 to 30 degrees, 20 to 30 degrees, or 25 to 30 degrees. The lens may comprise an electronic control system mounted with the micro-displays on a flexible transparent sheet of material such as plastic and other components.

In some embodiments, the micro displays comprise OLEDs with pixel sizes within a range from 2.0 micrometers (microns) to 5.0 microns, with a pitch within the range of 3.0 microns to 10.0 microns. In some embodiments, the micro displays comprise OLEDs with pixel sizes within a range from 5.0 micrometers (microns) to 50.0 microns, with a pitch within the range of 10.0 microns to 100.0 microns. In some embodiments, the micro-displays embedded in the lens comprise micro-LEDS illuminating an object, such as a thin film placed in front of it and toward the eye. The film may be transparent or translucent comprising a printed pattern that may be a Fourier transform of the image designed to be projected on the retina. The micro-displays may comprise polychromatic or monochromatic micro-displays. The polychromatic images can be formed by RGB pixels in the OLED or micro-LEDS of different colors, organized in arrays so as to form an RGB display. In some embodiments, the wavelength for stimulation of the retain is within a range from about 450 nm to about 560 nm (in some embodiments, from about 410 nm to about 560 nm), and can be near 500 nm, the peak wavelength of stimulation of rods in the eye, although other wavelengths may be used. In some embodiments, the chromaticity of the light sources includes violet light comprising a wavelength within the range from 400 to 450 nm.

In some embodiments, an optical configuration comprises one or more light sources coupled to one or more projection optics that comprise one or more of a collimating lens, a compound lens such as a Gabor lens, a prism, an array of prisms, a mirror, a lightguide, a waveguide, a plurality of mirrors, or holographic mirrors. In some embodiments, the waveguide is configured to preserve a phase of the wavefront transmitted therethrough. The one or more projection optics can be configured to image the one or more light sources so as to a project an image of the light source in front of, behind, or on the peripheral retina. In some embodiments, the optic configuration is placed at or near the anterior surface of the lens, and rays from the micro-displays are focused by the lens. In some embodiments, the lens is configured to provide refractive correction to the wearer, and the display optics configured to provide additional focus to provide the defocused image of the micro-display on the retina. In some embodiments, the amount defocus is in within a range from about 2.00 Diopter (D) to 6.00D, and can be within a range from about 2.0 D to 4.0D.

In some embodiments, a spectacle lens is configured with a near eye display that projects a 2.0 to 5.0 D or 2.0 to 7.0 D myopically defocused image at the outer retina toward the retinal periphery, while maintaining central vision. In some embodiments, a device comprises pair of spectacle lenses is configured with near eye displays that project a pair of 2.0 to 5.0 D or 2.0 to 7.0 D myopically defocused images at the retinal periphery, while maintaining central vision. Each optic of the device may be coupled to a near eye display to project the one or more myopically defocused images at the retinal periphery while the optical center of the spectacle lens optic provides the required refractive correction to the wearer for far vision. The optic can be configured to provide the refractive correction in order to allow comfortable and clear viewing of the real world at all object distances, while the display projects the 2.0 to 5.0 D or 2.0 to 7.0 D myopically defocused images toward an outer portion of the retina.

In some embodiments, a spectacle lens is configured to project myopically defocused images at the retinal periphery while maintaining good focus at the central retina. In some embodiments, a spectacle lens is configured to provide a light field, in which the refractive power of the lens varies with the gaze direction and object distance across the body of the spectacle lens optic. In some embodiments, the spectacle lens is configured to provide a match between vergence, image magnification and refractive correction. In some embodiments, near vision is usually associated with a lower gaze angle (inferior gaze), and the refractive power of a multifocal or progressive addition spectacle lens optic increases downwards. In some embodiments, the spectacle is configured for a wearer who can accommodate the spectacle provides less plus power. Additionally, the optical design of a binocular optic may be adjusted to promote binocular summation while executing conjugate eye movements. In some embodiments, the area of the spectacle lens optic that is left unmodified is an area approximately 8 to 15 mm, preferably 10 to 12 mm in diameter disposed around the optical center of the spectacle lens optic. In some embodiments, the area of the spectacle lens optic that is left unmodified is an area preferably 10 to 15 mm in diameter disposed around the optical center of the spectacle lens optic.

In some embodiments, the near eye display comprises a microminiature light source, such as an organic light emitting diode ("OLED"), a transparent organic LED ("TOLED") or an i-LED, and a micro-lens array to substantially collimate the light emanating from the light source and direct it to the pupil of the eye. Alternatively or in combination, a micro-mirror array can be used to collimate the light emanating from the light source and direct it to the pupil of the eye. In some embodiments, the light source is mounted on a transparent substrate (e.g., a TOLED), while in some embodiments, it may be mounted on an opaque substrate, such as silicon. The light source may comprise an active matrix or a passive matrix. The components can be held together in a transparent hermetically sealed package. In some embodiments, the hermetic sealing package may be conformal, comprising a multilayer film of total thickness within a range from 5 microns to 25 microns, for example from 10 microns to 15 microns. The device can also include a component that can monitor eye movements such as a gaze tracker. In some embodiments, a gaze tracker is configured to locate the point on the spectacle lens optic corresponding to the point of regard, at which the optic axis of the eye intersects the optic for a particular position of the eye as the eye executes pursuit eye movement such as tracking of a moving object. In some embodiments, eye movement may be monitored and followed by an eye tracker which may comprise a coil embedded in the eyeglass frame that senses movement of the eye through the development of a transient magnetic field during eye movement, for example from movement of a coil such as a coil within a contact lens worn on the eye. In some embodiments, retinal images formed by the light rays from the display are myopically defocused by 2.0D to 5.0D or 2.0 to 7.0 D anteriorly to the retina and are incident on the outer portions of the retina so as to form images anteriorly to the retina. While the images can be formed anteriorly to the retina in many ways, in some embodiments the images are formed about 15 degrees to 40 degrees eccentric to the fovea. In some embodiments the images are formed about 5 degrees to 40 degrees eccentric to the fovea.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 6 shows analysis of depth of focus of the optic configuration shown in FIG. 3;

FIG. 7 shows the MTF for the analysis of FIG. 6.

FIGS. 8A and 8B show an optical configuration comprising a lens to focus light onto the retina, in accordance with some embodiments;

FIG. 9 shows analysis of retinal image quality generated by the optic configuration shown in FIGS. 8 and 8B, in accordance with some embodiments;

FIG. 10 shows analysis of depth of focus of the optic configuration shown in FIGS. 8A and 8B.

FIGS. 11A and 11B show a light-pipe in order to increase the optical path length, in accordance with some embodiments;

DETAILED DESCRIPTION

Figure 1:
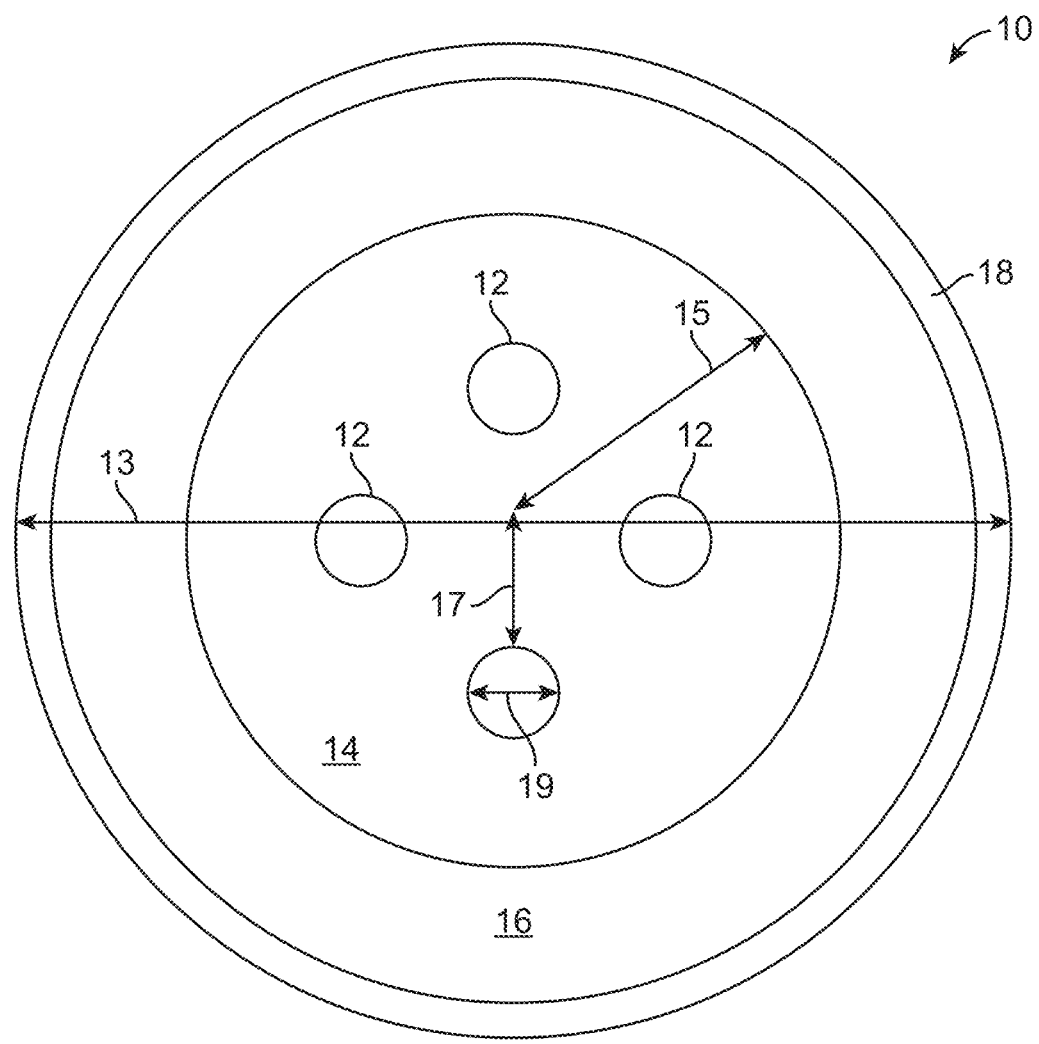
FIG. 1 shows a soft contact lens, in accordance with some embodiments.

The presently disclosed methods and apparatus can be configured in many ways to provide retinal stimulation as described herein. The presently disclosed methods and apparatus are well suited for combination with many prior devices such as, one or more of an ophthalmic device, a TV screen, a computer screen, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens. Although specific reference is made to spectacles and contact lenses, the presently disclosed methods and apparatus are well suited for use with any of the aforementioned devices, and a person of ordinary skill in the art will readily appreciate how one or more of the presently disclosed components can be interchanged among devices, based on the teachings provided herein. For example, although specific reference is made to a contact lens with projection optics, light sources and circuitry to stimulate the retina away from the fovea, the projection optics, light sources and circuitry can be incorporated into one or more of an ophthalmic device, a TV screen, a computer screen, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens, in order to provide retinal simulation as disclosed herein.

The methods and apparatus for retinal stimulation as described herein can be configured in many ways and may comprise one or more attributes to encourage a user to receive therapy. For example, the retinal stimulation as described herein can be combined with a display of a game to encourage a user to wear the treatment device. In some embodiments, the retinal stimulation can be combined with another stimulus, such as an emoji, to encourage a user to wear the device for treatment.

The retinal stimulation device may comprise global positioning system (GPS) circuitry for determining the location of the wearer, and an accelerometer to measure body movement such as head movement. The retinal stimulation device may comprise a processor coupled to one or more of the GPS or the accelerometer to receive and store measured data. The retinal stimulation device may comprise communication circuitry such as wireless communication circuitry, e.g. Bluetooth or WiFi, or wired communication circuitry, e.g. a USB, in order to transmit data from the device to a remote server, such as a cloud based data storage system. This transmission of data to the remote server can allow the treatment and compliance of the wearer to be monitored remotely. In some embodiments, the processor comprises a graphics processing unit (GPU). The GPU can be used to efficiently and rapidly process content from the web in order to utilize this content in forming the stimulus as described herein.

In some embodiments, the device comprises one or more cameras that are capable of capturing still images or video images of the real world scenery that may be used to form the stimulus signal.

In some embodiments, one or more projection optics is configured to project a defocused image on the retina away from the central field that includes the macula in order to stimulate an increase in choroidal thickness. In some embodiments, one or more projection optics is configured to project a defocused image on the retina away from the central field that includes the macula in order to stimulate a transient increase in choroidal thickness. The one or more projection optics can be configured to stimulate the retina without degrading central vision and corresponding images formed on one or more of the foveal or macular regions of the retina. In some embodiments, the one or more projection optics do not decrease the image forming characteristics of the vision correction optics prescribed to correct refractive errors of the wearers. The correction optics may comprise one or more of contact lenses, spectacle lenses, intraocular lenses, corneal onlays or corneal inlays. The one or more projection optic can be coupled to one or more light sources to illuminate the retina with one or more defocused images. In some embodiments, the one or more light sources comprises an optical display such as a micro-optical display, and the one or more projection optics comprises a micro-optical array. The components can be mounted on a flexible printed circuit board ("PCB") substrate to support the electronic and optical components. In some embodiments, the micro-display is optically coupled to a micro-optical array that substantially collimates and focuses the light emanating from the micro-display. The micro-display may comprise miniaturized pixels each with a size within a range from 2 microns to 100 microns. The micro-display can be coupled to and supported with the body of the correction optic such as a contact lens, or a spectacle lens, for example. In some embodiments, the micro-displays are coupled to and supported with one or more of an intraocular lens, a corneal prosthesis, a corneal onlay, or a corneal inlay. The optical configurations described herein with reference to a contact lens can be similarly used with one or more of an intraocular lens, a corneal prosthesis, a corneal onlay, or a corneal inlay, for example.

In some embodiments, one or more projection optics is coupled to and supported with a pair of spectacles. For example, the projection optics can be coupled to the outer surface or embedded in a pair of spectacle lenses. In some embodiments, the projection optics comprise a pico-projector mounted on the temples of an eyeglass frame. In some embodiments, the projection optics are optically coupled with one or more optical fibers that deliver the projected image to an eyeglass optics and be directed to the pupil of the eye, for example with a partially transmitting mirror. In these embodiments, an eye tracker can be configured to monitor eye movements so that the activation of the pixels in the micro-display can be programmed to compensate for the eye movement recorded by the eye tracker. In some embodiments, the eye tracker comprises a search coil mounted in the inner surface of the frame of the spectacle lens. The search coil can be configured in many ways to detect eye movement. In some embodiments, the subject is fitted with a contact lens to provide refractive correction for the eye of the subject. A metallic wire or magnetic material is embedded into the contact lens that creates a magnetic field in the search coil when eye movement occurs. In some embodiments, the magnetic field is analyzed with a processor to determine the start and stop point of the eye, and the time taken to execute the eye movement. In some embodiments the micro-display and the circuitry coupled to the display are configured to respond to the eye movement and selectively activate a different plurality of pixels in response to the eye movement within an appropriate time. The time to selectively switch to a second plurality of pixels in response to the eye movement can be less than 100 milliseconds, for example less than 20 milliseconds.

In some embodiments, the micro-displays and the micro-optic arrays are mounted immediately adjacent to each other on the same correction optic, separated by a fixed distance in order to project a bundle of rays to the pupil of the eye, at an orientation that it forms a myopically defocused image at a desired location on the retina as described herein. In some embodiments, the one or more projection optics is mounted on or in the one or more correction optics, such that rays from the projection optics are refracted through the correction optics. The correction optics refract the rays from the projection optics to be convergent or divergent as helpful for emmetropia, so that the micro-optical array can provide the desired magnitude of additional power that may be plus or minus, depending on the magnitude and sign of the defocus desired. The micro-display may be monochromatic or polychromatic, for example. The micro-display may have a luminance within a range from 1 nit to 10,000 nits or 10 nits to 1000 nits, or from 100 lux to 5,000 lux, for example. In some embodiments the micro-display may have a luminance within a range from 100 nits to 50000 nits, or from 50 lux to 5,000 lux, for example. In some embodiments, the micro-display is positioned eccentrically with respect to the optical center of the correction optic, at distances within a range from 1.0 mm to 4.0 mm from the center of the correction optic. In some embodiments, the micro-display forms an extended array of pixels, characterized by a pixel size and a pixel pitch, in which the pixel size and the pixel pitch together correspond to a fill factor of the micro-display. As described herein, pixel sizes may range from 2 microns to 100 microns, and the pixel pitch may range from 10 microns to 1.0 mm, for example. The corresponding fill factor can range from 0.1% to 10%. In some embodiments, the pixel array is optically coupled with a micro-optic array in order to substantially collimate and focus light from the pixels. In some embodiments, a layer of the micro-display and a layer of micro-optic array are encapsulated in a substantially transparent medium configured to decrease light scatter. The encapsulated image delivery system comprising the one or more light sources and the one or more projection optics may be subsequently coated with a conformal, hermetically sealing transparent multilayer coating, for example.

In some embodiments, the micro-display may be mounted on a correction optic such as a spectacle lens while the micro-optic array may be mounted on a second correction optic such as a contact lens, a corneal onlay or a corneal inlay. Alternately or in combination, an augmented reality (AR) or a virtual reality (VR) display may be used to project the defocused image on the retina. The AR or VR device can be mounted on an eyeglass frame, a goggle, or a head mounted display. Refractive correction may be provided by a spectacle lens or a contact lens, while optics coupled to the micro-optic array of the AR or the VR device provides the defocus.

In some embodiments, the projected defocused image can be provided by a screen comprising one or more of an LCD screen, a screen driven by OLEDS (organic light emitting diodes), TOLEDS, AMOLEDS, PMOLEDS, or QLEDS. The screen may be appear to the subject at a far distance of east least 6 meters or more, for example.

The stimulation can be configured in many ways and may comprise monocular stimulation or binocular stimulation.

The micro-optic array can be configured in many ways and may comprise one or more of an array of lenslets, an array of compound lenses, such as Gabor lenses, one or more mirrors, prisms, a lightpipe or a light guide, or a waveguide.

In some embodiments, the projected image comprises image structure content configured to provide a range of spatial frequencies, for example within a range from 2 cycles per degree to about 60 cycles per degree. In some embodiments, the projected image comprises image structure content configured to provide a range of spatial frequencies between 2 cycles per degree and about 30 cycles per degree. Work in relation to the present disclosure suggests that the capability of the peripheral retina to detect blur is higher than its ability to resolve images. The size and shape of the projected image may within a range from 100 microns to 2.5 mm, subtending a range of angles with respect to the fovea from 15 degrees to 360 degrees or from 5 degrees to 360 degrees, for example. The location of the image may be within a range from 5 degrees to 30 degrees eccentric to the fovea, for example within a range from 12 degrees to 30 degrees. Alternatively, the projected image may cover the whole retina for a pan-retinal treatment of defocus.

In some embodiments, the brightness of the projected image is within a range from 1 Troland to 250 Trolands. In some embodiments, the image brightness is adjustable based on the brightness of ambient illumination. The range of contrast of the projected image can be within a range from 99.9% to 2.5%, for example within a range of 99.9% to 10%.

Projection of the defocused image as described herein may be sustained over any appropriate amount of time, for example over a substantial part of a day (e.g. 8 hours or more), and the stimulation may be repeated every day at approximately the same time, so as to not to disturb circadian rhythms. The projected image may have a duration as short as 15 minutes, repeated throughout the day at hourly intervals, for example. The projected image may be continuous over a time within a range from 15 minutes to 12 hours per day. The stimulation may be provided over periods of 1 day to 3 years or as long as treatment is beneficial.

In accordance with some embodiments, a soft contact lens comprises peripheral micro-displays, each of which is fronted eye side by a micro-lens array. The micro-displays may comprise an OLED (organic light emitting diode) or an array of micro-LEDs. Light emitted by these displays is typically Lambertian. The micro-lens arrays are optically coupled with the displays, so that they can efficiently extract light from the micro-displays, collimate the light and focus it before projecting them into the entrance pupil. The virtual images created by these displays will be myopically defocused and will be placed symmetrically in the four sectors (nasal-inferior, nasal-superior, temporal-inferior and temporal-superior), in some embodiments. The micro displays will be located away from the optical center of the lens by a distance within a range from 1.5 mm to 4.0 mm, preferably 2.5 mm to 3.5 mm, in some embodiments. The central optic of the contact lens can be selected to bring the wearer as close to emmetropia as possible, and may have a diameter within a range 3.0 to 5.0 mm. Each micro-display will be circular, rectangular or arcuate in shape and will each have an area within a range from 0.01 mm$^2$ to 8.0 mm$^2$, for example within a range from 0.04 mm$^2$ to 8.0 mm$^2$, for example within a range from 1 mm$^2$ to 8 mm$^2$, or preferably within a range from 1.0 mm$^2$ to 4.0 mm$^2$, in some embodiments. In some embodiments, each of the plurality of micro-displays comprises the light source, the back plane and associated electronics with the dimensions and shapes as described herein. The contact lens will have an electronic control system as well as the micro-displays mounted on a flexible transparent sheet of plastic. The electronic system may comprise an ASIC or a microcontroller, a rechargeable Lithium ion solid state battery, a voltage ramping module e.g., a buck boost converter, a flash memory and an EEPROM, an RFID module to provide wireless recharging, or an antenna preferably disposed radially along the edge of the contact lens, and any combination thereof. The contact lens comprises a biocompatible material, such as a soft hydrogel or silicone hydrogel material, and may comprise any material composition that has proven to be compatible with sustained wear on the eye as a contact lens.

In some embodiments, virtual images focused at a target distance from the peripheral retina, equivalent to a myopic defocus. Rays forming these images do not come from outside environment but from the micro-displays themselves, so the optics of the micro-lens arrays can be solely designed to process the rays emanating from the micro-displays. The area of each of these micro-displays and micro-lens arrays in front of each is small, so the obscuration of the real image is small, as shown in FIGS. 1 and 2.

The device as described herein can give each caregiver substantial flexibility in setting and testing such parameters for an individual patient, then refining the preferred parameters of treatment based on observations of patient response.

Some embodiments comprise a contact lens of diameter 14.0 mm, with an edge zone of 1.0 mm and a peripheral zone 16 whose inner diameter is 6.0 mm and outer diameter is 12.0 mm. The overall diameter of the lens may be in the range of 13.0 mm and 14.5 mm, preferably 13.5 and 14.5 mm. The central optical zone 14 is designed to cover the pupil of all wearers under all illumination conditions, and should therefore have a diameter in the range of 5.0 mm and 8.0 mm. The peripheral or the blend zone is primarily designed to provide a good fit to the cornea, including good centration and minimum decentration. The central optical zone 14 is designed to provide emmetropic correction to the wearer and may be provided with both spherical and astigmatic correction (FIG. 1). Contact lens designs suitable for incorporation in accordance with embodiments disclosed herein are described in Douthwaite, D. A., "Contact lens optics and lens design", 3$^{rd}$ edition, 2006; ISBN 978-0-7506-88-79-6; Butterworth-Heinemann.

In some embodiments, the inner surface of the contact lens is embedded with a set of four micro-displays coupled eye side with micro-lens arrays of the same size. The function of the micro-lens arrays is to collimate the light being emitted by the micro-displays, collimate it, and focus it at a focus that is designed to be in the front of the eye, to provide hyperopic defocus. The micro-displays can be sized in many ways, and each of these micro-displays is only about 0.04 mm$^2$ to 2 mm$^2$ in area, for example from 1 mm$^2$ to 2 mm$^2$ in area, so that these displays cover less than 1% of the contact lens optic, in some embodiments. Each of the displays will generate about 30-50 cd/m$^2$ or greater of illumination, quite sufficient for forming a relatively bright image at the focus of each of these micro-displays. The focused images will appear approximately 1.5-2.5 mm in front of the peripheral retina, since they will be designed to be myopic by about 2.0D to 5.0D, for example 2.0D to 4.0D, or preferably 2.5D to 3.5D, for example.

In some embodiments, the micro displays may be OLEDs with pixel size of 2.0 microns to 5.0 microns, with a pitch in the range of 2.0 microns to 10.0 microns. In some embodiments, the micro-displays embedded in the contact lens as described herein will consist of micro-LEDS illuminating an object, such as a thin film placed in front of it, eye side. The micro-displays may be polychromatic or they may be monochromatic. The polychromatic images are formed by RGB pixels in the OLED or micro-LEDS of different colors, organized in arrays so as to form an RGB display. Data on wavelength dependence of axial length alteration of the projected hyperopic or myopic image at the peripheral retina are lacking. A preferred wavelength for stimulation of change in axial length is 500 nm, the peak wavelength of stimulation of rods in the eye, although other wavelengths may be used.

The amounts and location of illumination on outer locations of the retina to provide a therapeutic benefit can be determined by one of ordinary skill in the art without undue experimentation in accordance with the teachings disclosed herein. The length and duration of peripheral stimulation can be determined, for example optimized, based on available preclinical data in animal models. For example, some studies suggest that changes in axial length in animal models can be obtained on repeated application of defocus stimuli, in preference to a single sustained period of equivalent duration of imposed defocus. Examples of studies with information on illumination changes in axial length suitable for incorporation in accordance with the embodiments disclosed herein include: Wallman, J., et al, "Homeostatis of eye growth and the question of myopia", in Neuron, 2004; 43: pp 447; Benavente-Perez, A, et al, "Axial Eye Growth and Refractive Error Development Can Be Modified by Exposing the Peripheral Retina to Relative Myopic or Hyperopic Defocus" In IOVS 2014; 55: pp 6767; and Hammond, D. S., et al, "Dynamics of active emmetropisation in young chicks—influence of sign and magnitude of imposed defocus" in Ophthalmic Physiol Opt. 2013; 33: pp 215-222.

Work in relation to the present disclosure suggests that the duration and distribution of application of peripheral myopic defocus will depend on individual physiology and the precise shape of the retina. An embodiment comprises a reprogrammable MCU or ASIC controlling the operation of the micro-displays, and a real time clock that will enable adjustment of the treatment duration and periodicity by the caregiver, throughout the treatment. This embodiment also enables the caregiver to test whether nocturnal stimulation (sustained or repeated sequence of short pulses) has an efficacy for certain individuals.

In some embodiments, the electronic components are populated on a flexible thin film on which interconnects and electrical bus are deposited by means of vapor deposition or a 3D printing process. In some embodiments, the electronics and the micro-displays are further coated with a flexible stack of thin barrier film, such as a stack of Paralyne C and $SiO_x$ film of total thickness 5-10 microns, developed by Coat-X, a corporation located in Neuchatel, Switzerland.

Some embodiments of the device deploy a set of one to eight micro-displays, each circular or arcuate in shape, and they are disposed radially on the inner surface of the contact lens, all at the same distance from the optical center of the lens. In one embodiment, they may be monochromatic. In another embodiment they may be designed to provide white light output. In a third embodiment, they may be designed to output illumination matched to the retinal sensitivity. These micro-displays are operated and controlled by a reprogrammable microcontroller (MCU) or an ASIC.

In some embodiments, the contact lens is worn during sleep, and the micro-displays are programmed to operate only when the wearer is asleep. Such a programmed stimulation of reduction of the axial length will interfere minimally with daily activities, including reading and computer work. The contact lens may even be removed during daytime activities, while it is fit on the cornea just before going to sleep. Other embodiments may utilize other programming algorithms, for example a combination of daytime and nighttime stimulations.

In some embodiments, the contact lens may be a daily disposable lens, obviating the need for disinfecting and cleaning the lens or recharging it. Another embodiment consists of a contact lens of planned replacement modality.

In some embodiments, each micro-display (1 $mm^2$ to 4 $mm^2$) will consume about 10 microwatts of electrical energy. In these embodiments, a set of four micro-displays may use about 125 microwatt-hours of electricity for 2 hours of operation, so that the total daily energy consumption for this design will be expected to be 0.2 milliwatt-hour. In some embodiments, each micro-display comprises a cross-sectional area within a range from about 0.04 $mm^2$ to 4 $mm^2$ and consumes about 10 microwatts of electrical energy. In some embodiments, the electrical power is supplied by a rechargeable, solid state lithium ion battery. A bare die solid state rechargeable lithium ion battery, marketed by Cymbet Corporation, may be populated on the same flexible substrate as the electronics of the lens. For example, a 50 uAH rechargeable lithium ion solid film battery has dimensions of 5.7×6.1 mm×0.200 mm (Cymbet Corporation CBC050). In some embodiments, the battery comprises sufficient mass to stabilize the contact lens. For example, the battery can be located on an inferior position of the lens in order to stabilize the lens with gravity. The inferiorly located battery may comprise a mass sufficient to decrease rotational movement such as spinning when the wearer blinks.

In some embodiments, an electronic contact lens projects a 2.0 to 5.0 D or 2.0 to 7.0 D myopically defocused image at the retinal periphery, while maintaining excellent vision at the center.

In some embodiments, the electronic soft contact lens comprises microscopic light sources and microscale optics embedded at the periphery of the lens optic. The contact lens optic can be designed to provide excellent vision at the central retina, while the outer light sources project images at the outer portions of the retina that are myopically defocused. In some embodiments, the light sources comprise micro displays. In some embodiments, the outer images formed anterior to the retina may to stimulate the retina to move forward, reducing the axial length and deepening the vitreous compartment. In some embodiments the contact lens is configured to one or more of decrease myopia progression, substantially stop myopia progression, or reverse myopia in the eye wearing the lens. In some embodiments, the contact lens can be configured for extended wear and replaced once a month, for example. The contact lens can be replaced more frequently or less frequently, for example, once a week, or once every three months. In some embodiments, the contact lens is designed to be worn by teens and young adults, who can be at greater risk of myopia progression than people of other ages.

In some embodiments, the amount of myopic defocus of the peripheral image is within a range from about or 2.0D to about 7.0D, for example from 2.0D to about 5.0D or from about 2.5D to about 5D. Based on the teachings disclosed herein a person of ordinary skill in the art can conduct studies such as clinical studies to determine appropriate amounts of defocus, illumination intensities and times of illumination. In some embodiments, one or more of the amount of defocus, the retinal locations of the retinal illumination or the times of illumination can be customized to an individual, for example in response to physiological characteristics of the individual patient. The duration of treatment can be within a range from 1 to 3 years, for example about 2 years. In some embodiments, the treatment is performed with a number of lenses within a range from about 10 lenses to about 40 lenses, for example from about 10 lenses to about 30 lenses. The prescription of the optical zone 14 comprising the central lens optic may change with time during treatment, and the prescription of the contact lens can be changed is appropriate. The contact lenses as disclosed herein may also be subsequently worn as needed, for example if myopia progression returns.

The electronic contact lens can be configured in many ways to correct refractive error of the wearer. In some embodiments, the contact lens comprises a plurality of micro-displays that emit light near a periphery of the optical zone 14 of the contact lens, a plurality of micro-optics to collect, collimate and focus the light rays emanating from the light sources, a miniaturized rechargeable solid state battery to provide power to the light sources (e.g. a Lithium ion solid state battery), an antenna to wirelessly receive power to recharge the battery, and a micro-controller to control actuating and controlling functions, and a memory to store data or software instructions.

In some embodiments, the outer image comprises a peripheral image located outside the macula, for example within a range from about 20 degrees to about 30 degrees eccentric to the fovea.

The contact lens can be configured in many ways with a plurality of optics such as micro-optics to collect light from a plurality of light sources (e.g. microscope light sources) and form an image anterior to an outer portion of the retina such as anterior to a peripheral portion of the retina. In some embodiments, the plurality of optics comprises one or more of a light-pipe and a reflective component, such as mirrors, for example microscopic mirrors.

The device as described herein can be used to treat advancement of refractive error such as myopia. In some embodiments, each caregiver has substantial flexibility in setting and testing parameters for an individual patient, then refining the preferred parameters of treatment based on observations of patient response.

In some embodiments, the optical design of the refractive properties of the contact lens substantially unaltered and can be configured in many ways. For example, the central optical zone 14 of the contact lens can be optimized for best correction of the far image at the fovea, while providing images at the periphery of the retina that are anterior to the image shell of the contact lens optic, so as to decrease the advancement of refractive error. In some embodiments, the light sources may comprise a surface area of no more than 2 mm$^2$ of the optical surface, and the size of the optical surface to correct refractive error can be within a range from about 25 mm$^2$ to about 50 mm$^2$, which can decrease the effect of the light source on vision. An intensity of the peripheral image that can be provided independently of the level of ambient illumination, and the intensity of the light sources can be adjusted over several orders of magnitude by selecting light sources of appropriate power. The soft contact lens can be configured to provide appropriate amounts of illumination response to input from the wearer or a health care provider.

FIG. 1 shows micro-displays 12 embedded in a lens as described herein, such as a contact lens 10. Although reference is made to a contact lens, the lens 10 may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

The soft contact lens 10 comprises an optical zone 14 configured to provide far vision correction to the wearer, for example with a visual acuity of 20/20 or better. The optical zone 14 may comprise a distance across such as a diameter or a radius 15, which may comprise any suitable size such as a radius of about 3 mm. The micro-displays 12 can be configured to provide the images in front of the peripheral portion of the retina as described herein. This configuration can allow the user to have good visual acuity while receiving therapy from the images focused in front of the retina as described herein. The micro-displays 12 can be located outside the optical zone 14, or inside the optical zone 14. Each of the micro-displays 12 may comprise a maximum distance across, such as a diameter 19, which can be any suitable size, for example about 1 mm.

The micro-displays 12 may comprise micro-LEDS illuminating an object, such as a thin film placed in front of it, eye side. The light emitted by these micro-displays 12 can be Lambertian and directed to an optical element such as a lens to direct the light beam toward the retina. The contact lens 10 comprises a diameter 13 suitable for placement on an eye. For example, the contact lens 10 may comprise a diameter within a range from about 10 mm to 15 mm, for example 14.0 mm. The contact lens 10 may comprise a plurality of embedded micro-displays 12. Each of the plurality of micro-display 12 can be optically coupled to an optical configuration that collects light emitted by the micro-display 12 and projects an image on or in front of the retina of the wearer at a specified eccentricity. Each of the displays 12 can generate an illumination within a range from about 1 cd/m$^2$ to about 50 cd/m$^2$. In some embodiments each of the displays 12 can generate an illumination within a range from about 50 cd/m$^2$ to about 50000 cd/m$^2$ or from about 100 cd/m$^2$ to about 50000 cd/m$^2$. The amount of illumination can be sufficient for forming a relatively bright image at the focus of each of these micro-displays 12.

In some embodiments, the amount of illuminance is intermediate between photopic and mesopic levels of illumination and intermediate levels of sensitivity of rods and cones. In some embodiments the amount of illumination is within a range from about 10 cd/m$^2$ to about 50000 cd/m$^2$, such as from 100 cd/m$^2$ to about 50000 cd/m$^2$, preferably from 10 cd/m$^2$ to 2000 cd/m$^2$ at the pupil plane. In some embodiments, the amount of illumination is within a range from about 0.1 cd/m$^2$ to about 10 cd/m$^2$, for example from 0.5 cd/m$^2$ to 5 cd/m$^2$ at the pupil plane. The amount of illuminance may correspond to an amount of light between moonlight and indoor lighting, for example. In some embodiments, the amount of illumination corresponds to mesopic vision.

In some embodiments, the micro-displays 12 can comprise light sources that emit polychromatic light composed of light of different wavelengths. In other embodiments, the light sources emit monochromatic light. In some embodiments, the wavelength of the monochromatic illumination can be in the range of 500 nm to 560 nm, preferably from 500 nm to 530 nm, more preferably from 500 nm to 510 nm.

In some embodiments, the polychromatic light sources provide chromatic cues to the peripheral retina. The chromatic cues may comprise negative chromatic aberration. In some embodiments, a poly chromatic light beam is focused anterior to the retina, in which the polychromatic light beam comprises a positive chromatic aberration prior to an image plane 35 or a focal plane and a negative chromatic aberration after the image plane 35 or focal plane so as to illuminate the retina with a negative chromatic aberration.

While the polychromatic illumination can be configured in many ways, in some embodiments, the polychromatic illumination comprises red illumination, blue illumination and green illumination, although other wavelengths of light may be used.

In some embodiments, the projected images appear approximately 1.5 mm to about 2.5 mm in front of the peripheral retina, since they will be designed to be myopic by about 2.0D to 4.0D, for example from 2.5D to 3.5D. In some embodiments, the projected images appear approximately 1.5 mm to about 2.5 mm in front of the peripheral retina, since they will be designed to be myopic by about 2.0D to 7.0D, preferably 2.5D to 5.5D. In general, 1 mm in front of the retina corresponds to about 2.5 D of myopia, for example about 2.7 D of myopia.

This approach of peripheral stimulation of change in axial length through thickening or thinning of the choroid can be based on repeated and confirmed observations of the efficacy of application localized hyperopic or myopic defocus in stimulating change in the axial length of the eye 11. The length and duration of peripheral stimulation can be based on available preclinical data in animal models as is known to one of ordinary skill in the art. For example, the rate of change in axial length can obtained on repeated application of defocus stimuli, in preference to a single sustained period of equivalent duration of imposed defocus.

In some embodiments, the duration and distribution of application of peripheral myopic defocus depends on individual physiology and the shape of the retina. In some embodiments, the contact lens 10 comprises a programmable processor such as a microcontroller unit (MCU) or application specific integrated circuitry (ASIC) for controlling the operation of the micro-displays 12. The contact lens 10 may comprise a real time clock to adjust the treatment duration and periodicity by the caregiver, and the treatment duration and periodicity may be provided throughout the treatment. In some embodiments, the caregiver tests whether nocturnal stimulation (sustained or repeated sequence of short pulses) has an efficacy for certain individuals.

Spectacles for Retinal Simulation

Figure 1A:
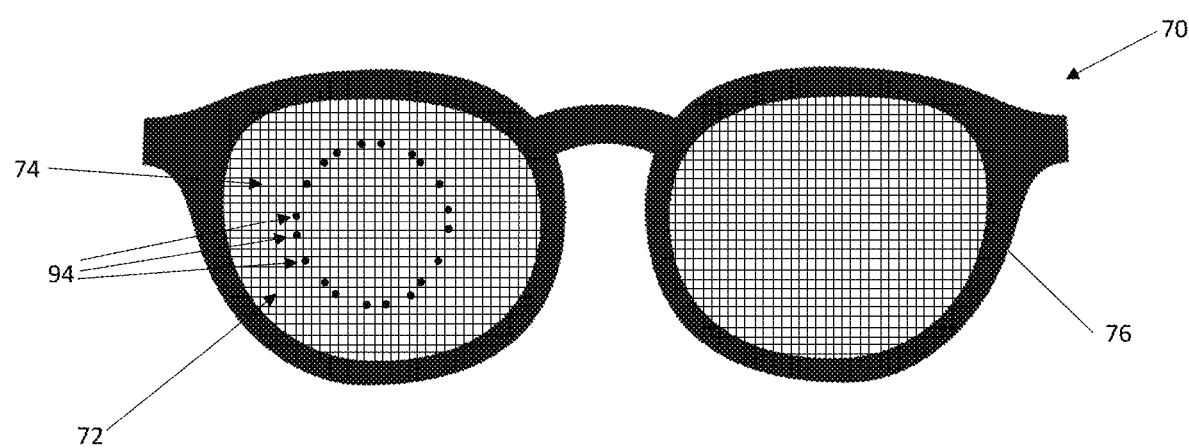
FIGS. 1A and 1B show spectacles suitable for incorporation with the present disclosure, in accordance with some embodiments.
Figure 1B:
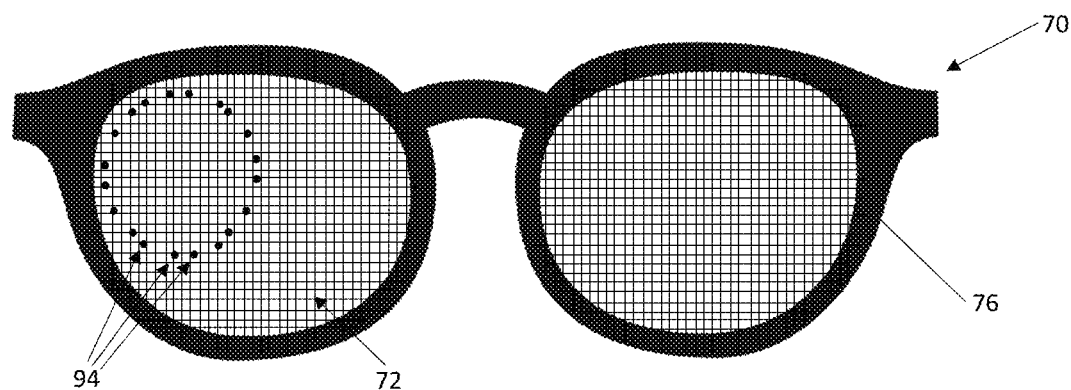

FIGS. 1A and 1B depict spectacles 70 for the treatment of refractive error of the eye and suitable for incorporation in accordance with the present disclosure. Although reference is made to spectacles, the light sources can be provided on any vision device described herein to treat refractive error of the eye and to decrease myopia progression or reverse myopia, such as augmented reality ("AR") devices. A plurality of light sources is arranged to treat myopia. The plurality of light sources may comprise any suitable light source as described herein, such as a micro display or projection units, for example. In some embodiments, the light sources are configured to provide illumination at the peripheral retina in order to promote changes in choroidal and scleral tissue corresponding to different changes in axial length as described herein. The lens may comprise an optical zone with optical properties, e.g. refractive properties, configured to treat refractive error of the eye and to decrease myopia progression or reverse myopia. This refractive treatment of can be combined with retinal stimulation as described herein.

The spectacles 70 may comprise one or more components of commercially available augmented reality glasses, such as the ORA-2 commercially available from Optinvent (with a presence on the Internet at optinvent.com). The spectacle 70 may comprise one or more displays 72 for retinal stimulation. The near eye displays 72 may be mounted to lenses 74. The lenses 74 may be spectacle lenses supported by eyeglass frame 76. The lens 74 may be a corrective or non-corrective lens. The lens 74 may be a plano lens, a spherical corrective lens, an astigmatic correction lens, or a prism correction lens. In some embodiments, the near eye display is located away from an optical zone to provide clear central vision, such as of the real world over a field of view in the range of +/−2.0 degrees to +/−15.0 degrees or +/−2.0 degrees to +/−12.5 degrees. An optical axis may extend along a line of sight from an object of the patient's regard, though the lens 74 to a fovea of the eye. In some embodiments, the spectacle 70 comprises an eye tracker suitable for incorporation in accordance with the present disclosure. The near eye display 72 can be programmed to selectively activate pixels 94, in order to provide peripheral stimulation to the retina, as described herein. In some embodiments, a layer of a plastic substrate bearing micro-lenses is attached to the micro-display in order to generate the desired level of defocus and stimulation at the retina. The selectively activatable pixels can be arranged to provide an appropriate eccentricity with respect to a line of sight of the patient, so as to provide peripheral retinal stimulation as described herein.

In some embodiments a near eye display 72 comprises a combination of a micro-display and a micro-optic. The micro-display can be placed sufficiently close to the eye so that the eye does not accommodate to focus light rays emanating from the near eye display, even with the full range of natural accommodation available to the human eye. In some embodiments, the micro-optic is configured to collect, substantially collimate and focus the light rays emanating from the micro-display. In some embodiments, the micro-optic is configured to form an image of the display anterior to or posterior to the retina as described herein. In some embodiments, the distance of the near eye display from the entrance pupil of the eye is within any suitable range, such as a range from about 10 mm to about 30 mm, or a range from about 18 mm to 25 mm, for example at a distance of about 15 mm. The micro-display can be placed on a transparent substrate, such as the front or back surface of the lens 74 of the spectacles 70. When the micro-display is placed on the front surface of the lens 94, then the focus of the micro-displays may be affected by the refractive correction on the back surface of the lens 94.

In some embodiments, the focus of the pixels in a micro-display may vary based on their location on the lens 74 and the refractive correction provided by the lens in that area. In some embodiments, the focus of the pixels may be fixed. In some embodiments, the focus of the pixels may vary based on the sensed position of the cornea to account for the refraction of the cornea and the lens of the eye. In some embodiments, the pixels are defocused to create a defocused spot on the retina about 1 mm in diameter.

Light emitted by the pixels 94 in the micro-display of the near eye display can be one or more of substantially collimated or focused before being directed to the pupil of the eye. In some embodiments, a micro-lens array is aligned to the pixels of the near eye display, so that rays from the near eye display can enter the pupil and form an image anterior to or posterior to the retina. In some embodiments, the width of the near eye display corresponds to a patient's field of view. In some embodiments, the extent of the near eye display may be substantially similar to the extent of the lens 74 of the spectacles 70. In some embodiments, the near eye display can be curved so that rays from pixels over the whole width of the display can be normal with respect to the pupillary plane. In some embodiments, a prismatic tilt is provided to be provided to the lenses in the micro-lens array, in order to compensate for the tilt of the plane of the micro-display away from the pupillary plane.

Work in relation to the present disclosure suggests that a myopically defocused retinal stimulus is likely to be more effective in preventing myopia progression when applied peripherally than when the foveal and/or the macular image is also myopically defocused. The device can be configured to be worn for any suitable amount of time to provide myopia treatment. The myopia treatment device can be worn at appropriate times for a treatment of two years or longer to maintain the emmetropia of the wearer or to direct the growth of the eye toward emmetropia, for example if the wearer has an inclination to shift to a myopic optical configuration of the eye. In some embodiments, the vision corrective device is configured to be worn for relatively long periods for example, for several hours per day over a period of 1 month and up to 2 years, depending on the rate of myopia reversal, for example. The refractive prescription of the central optical zone can be changed in response to the treatment. For example, if myopia is decreased, the myopic correction of the central optical can be decreased. The refraction of the treated eye can be measured at any appropriate time period, such as monthly, and the prescription of the central optical zone changed when appropriate.

In some embodiments, the device provides unimpaired central vision so that the quality of life and quality of vision of the wearers are not adversely affected. In some embodiments, central vision comprises of a field of view of +/−12.5 degrees, covering the macula, while foveal vision used for fixation has a field of view of +/−2.0 degrees. In some embodiments, central vision comprises of a field of view of +/−4.5 degrees, covering the macula, while foveal vision used for fixation has a field of view of +/−2.0 degrees. In some embodiments, the defocused image is projected at an outer portion of the retina toward the periphery of the retina, for example within a range from 15 degrees to 40 degrees eccentric to the fovea and can be within a range from 20 degrees to 30 degrees. In some embodiments, the micro-display 72 does not obstruct the central vision field of view. In some embodiments, the pixels 94 do not obstruct the central vision field of view.

Alternatively or in combination with the eccentricity of the myopically defocused image, the device can be configured to illuminate an appropriately sized area of the image or image footprint on the retinal image shell. Work in relation to the present disclosure suggests that illuminating at least a portion of each of four quadrants of the retina can be helpful. In some embodiments, each image on a quadrant of the retina occupies approximately 45 degrees of arc circumferentially. In some embodiments, each image on a quadrant of the retina occupies approximately 30 degrees of arc circumferentially. Suitable amounts of illumination at appropriate locations can provide stimulation to the eye to remodel the choroid and ultimately the sclera and to reduce the axial length of the eye and lead to a reduction of myopia.

The micro display and optics can be configured in many ways to provide appropriate stimulation to outer regions of the retina toward the periphery. In some embodiments, the micro-displays and optics are configured to project light onto outer regions of the retina sufficiently far from the fovea, that the illumination remains substantially fixed even with eye movement. In some embodiments, the point of regard is monitored and the desired location of the pixels to be activated on the micro-display is determined, e.g. by a computations with a processor, such that an image is projected at the desired location on the retina, allowing persistent stimulation at the same retinal location. In some embodiments, the point of regard on the spectacle plane or the plane of the micro-display is calculated by monitoring the horizontal, the vertical and torsional displacement of the eye relative to the primary position.

The point of regard can be determined with a in many ways, for example with an eye position sensor such as a magnetic sensor or an optical sensor. In some embodiments, a search coil embedded in the eyeglass frame is used to track eye movements. The coil embedded in the eyeglass frame can be coupled to a magnetic structure placed on the eye, such as one or more of a coil on a contact lens, a coil implanted in the eye, a magnetic material on a contact lens, or a magnetic material implanted in the eye. In some embodiments, the sensor comprises an optical sensor, such as a position sensitive detector or an array sensor to measure a position of the eye optically. The optical sensor can be configured to measure a position of the eye in many ways, for example configured to measure a position of one or more of a corneal reflex from a light source, a pupil, a limbus or a sclera. The eyeglass frame may support an additional light source to illuminate the eye, for example to generate a corneal reflex. Data from the sensor can provide the location of the coaxially sighted corneal light reflex ("CSCLR"), and hence the direction of the visual axis and the location of the fovea. The point of regard, visual axis, optical axis, nodes of the eye, and CSCLR are described in "Ocular axes and angles: time for better understanding", Srinivasan, S., in J CATARACT REFRACT SURG—VOL 42, MARCH 2016.

In some embodiments, the near eye display comprises a transparent, flexible substrate that matches the curvature of the eyewear worn by the user. The near eye display can be mounted on the outer side of the optic and the frame of the eyewear. The frame and the temples can be made hollow or appropriately shaped in order to accommodate the electronics, including the electronic driver of the display, the rechargeable battery used to provide power to the system, a memory to store algorithms that control the operation of the near eye display. The device can be recharged in many ways, for example by using a micro-USB port, or wirelessly, by using a recharging module.

In some embodiments, the processor, using the eye position sensor, may be configured to adjust the optics, such as the pixels in the micro display to reduce movement of the stimulated locations of the retina in response to eye movement. In some embodiments, target locations of the peripheral images are computed from the location of the fovea based on the information form the eye position sensor and a real time ray tracing calculation provides the locations of the pixels to be activated in the micro-display. The time to selectively switch to a second plurality of pixels in response to the eye movement can be less than 100 milliseconds, for example less than 20 milliseconds.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard. For example, FIG. 1A shows active pixels 94 when a patient is looking level and straight ahead, so-called primary gaze, while FIG. 1B shows active pixels 94 when a patient is looking up and to the left. In such a case, the shape of the array of pixels may be the same, but translated up and to the left, or the shape of the array may change. In some embodiments, the plurality of light sources, e.g. active pixels 74, are configured to change so as to maintain alignment of the optical axis of the eye. This alignment can be provided with processor instructions configured to selectively activate pixels in accordance with the eye movement and the optical axis of the eye.

In some embodiments a near eye display module is mounted on the outer side of a spectacle lens. Alternatively, the near eye display can be mounted on an inner side of a spectacle lens. In some embodiments, the device is binocular and comprises a micro-display and optics for each eye of the wearer. The micro-display can be optically coupled with one or more micro-optical components, designed to substantially collimate the illumination generated by the pixels of the micro-display and rendered convergent, before entering the pupil.

In some embodiments, a display 72, e.g. a display module, is mounted on the outer side of a spectacle lens and aligned with the spectacle lens optic such that the near eye display can provide a field of view of +/−40 degrees or greater, so that the micro-display can continue to provide peripheral retinal stimulus for the normal range of eye movements, typically +/−15 degrees laterally, such as +/−5 degrees laterally, and +10 to −20 degrees vertically, such as +/−7, or +/−20 degrees vertically, including downgaze when reading or viewing near objects. In some embodiments, light from the micro-display is transmitted through the spectacle lens optic and provided with the refractive correction of the wearer.

In embodiments, the refractive correction comprises one or more of a spherical correction, or a correction for astigmatism. In some embodiments, the correction comprises a prismatic correction for correction of strabismus and correction for inadequate accommodation that can vary across the spectacle lens optic, such as a progressive addition lens ("PAL"). In some embodiments, the micro-optic of the near eye display is configured to provide myopic defocus required to generate the peripheral retinal stimulation for the prevention of myopia progression as described herein, for example with stimulation to outer regions of the retina with images formed anteriorly to the retina.

In some embodiments, the optical system is configured to form the images anterior to the retina and comprises one or more of a single micro-lens (lenslet), a plurality of micro-lenses (lenslet array), a compound lens, such as a Gabor lens, a micro-prism, or a micro-mirror, or a combination thereof. In some embodiments, light baffles and micro-mirrors are arranged to ensure that the amount of light not captured by the micro-optic is substantially decreased, e.g. minimized, in order to reduce stray light and light escaping from the front side of the display.

In some embodiments, a pixel fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns leads to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels 94 can be collected, collimated and focused to be directed to the pupil of the wearer at primary gaze. The density of these micro-optical elements can control the overall visibility of the near eye display. In some embodiments, the micro-optic has a low fill factor (preferably equal to or less than 0.1) so that the overall light transmission through the near eye display will be acceptable to wearers and allow the patient to view objects.

In some embodiments the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

In some embodiments, the location of the pixels in the micro-display to be activated to form the outer image toward the periphery of the retina is referenced from the optical center of the eyeglass optics, since it is the point of regard at primary gaze. In some embodiments, the location of the point of regard is calculated by taking into account eye movement relative to the position of the eye at primary gaze and calculating the location of the pixels to be activated with reference to the new point of regard.

In some embodiments, a plurality of pixels is activated to form the light source that is imaged by the micro-optics. The optical design of the micro-optics and its separation from the micro-display can be configured to provide the focal length of the image delivery system, the image magnification of the image projected on the retina and the blur caused by diffraction, as measured as the Airy disc diameter of the optical delivery system.

The technical specifications are given in Table 1, in accordance with some embodiments.

TABLE 1

Optical specifications of the augmented reality near eye display for prevention of myopia progression.

| Optical Specification | Preferred Magnitude | Range |
| --- | --- | --- |
| Field of View | +/−25 degrees (50 degrees total) or +/−10 degrees (20 degrees total) | 40-80 degrees or 5-80 degrees |
| Eye Box | 8 mm | 4-10 mm |
| Eye relief | 15-18 mm | 15-25 mm |
| Optical power additional to refractive correction | Myopic defocus of 3.5 D | 2.0 D to 5.0 D or 2.0 D to 7.0 D |
| Display color | Green | Polychromatic (RGB) or white |
| Brightness | 300-500 cd/m2 or 100-1000 cd/m2 | 100-10,000 cd/m2 |
| Resolution | 2.5 min arc/pixel or 1.0 min arc/pixel | 1-10 min arc/pixel |

Optical resolution or quality of the peripherally projected image can be related to three factors: depth of focus, image magnification and Airy disk diameter. Depth of focus of near eye display depends on the focal length and the aperture of the near eye display as well as image magnification (Equation 1).

$$\text{Depth of focus} = 2N^{*}c^{*}(1+m) \quad \text{(Equation 1)}$$

when N is the f number (f/D, where f is focal length and D is diameter), c is the minimum circle of confusion and m is image magnification.

In typical eyes, a myopic defocus of 1.0D causes the image at best focus to move forward by 0.35 mm approximately.

The resolution of the retina decreases with eccentricity, so that retinal resolution in the desired range of eccentricity drops to 20 line pairs/mm at eccentricities in the range of 20-40 degrees. It has been found that even at these eccentricities, the retina is capable of detecting the presence of a stimulus at a higher level of spatial frequency. Accordingly, in some embodiments the micro-optic array designed to form and project a peripheral image is corrected for optical aberrations and is capable of forming an image for which the modulus of OTF is equal to or better than 0.3 at a spatial frequency of 50 lp/mm or greater.

Work in relation to the present disclosure suggests that the retina perceives changes in image blur caused by higher order aberrations present in the defocused image (in addition to the spherical defocus), including longitudinal chromatic aberration (LCA), higher order spherical aberration, astigmatism, etc. that are sensitive to the sign of the defocus. Based on the teachings provided herein a person of ordinary skill in the art can conduct experiments to determine whether the retina can recognize a myopic blur from a hyperopic blur when the depth of focus of the device is greater than or nearly equal to the magnitude of defocus. The device as described herein can be appropriately configured to provide appropriate amounts of defocus at appropriate locations, for example.

The device can be configured to provide appropriate image magnification, diffraction that limits the image resolution and depth of focus in relation to the magnitude of myopic defocus being applied and the rate of change of image blur or image sharpness gradient as a function of the magnitude of defocus. The human eye may have a lower threshold of blur perception. Since the intensity of the growth signal to the retina and the choroid depends on the magnitude of myopic defocus perceived in terms of image defocus, the extent of defocus and blur perception can be considered in estimating the expected strength of growth signal generated by a particular optical configuration relative to the magnitude of myopic defocus applied to the retinal image by the near eye display.

In some embodiments, the near eye display is configured to provide a clear, substantially undistorted field of view of the foveal and macular image for comfortable vision. In some embodiments, the field of view of the central image is at least +/−12 degrees or at least +/−5 degrees and can be more in order to account for differences in interpupillary distance (IPD) of different wearers. Image quality and field of view of the real image can be provided with a substantially transparent near eye display transparent, and by reducing the fill factor of light emitting pixels in the microdisplay. In some embodiments, a fill factor less than 10% (0.1) is sufficiently sparse to provide a clear view of the foveal and macular image. In some embodiments, the fill factor is in the range of 0.01 to 0.3 and can be within a range from 0.05 to 0.20. For example, an array of pixels of pixel size 5 microns and a pixel pitch of 20 microns will lead to a fill factor of 0.06. A low fill factor may also reduce the complexity of the manufacturing process and reduces the cost of such micro-optic displays.

In some embodiments, the micro-optic array is designed to be optically aligned with the display, so that light from a single or a plurality of pixels can be collected, collimated and focused to be directed to the pupil of the wearer at primary gaze. The population density of these micro-optical elements can control the overall visibility of the near eye display. In some embodiments, the micro-optic has a low fill factor (preferably equal to or less than 0.1) so that the overall light transmission through the near eye display will be acceptable to wearers.

In some embodiments the device comprises a switchable micro-optic array that can be switched between a plano (no optical power) state and an activated state by electro-optical components, utilizing for example a liquid crystal or a LC based material that can be switched from one refractive index to another, or one polarization to another, for example. In some embodiments, the micro-optic array does not scatter light or distort images of the real world when it is not activated.

Retinal Stimulation Light Sources and Circuitry

Figure 2A:
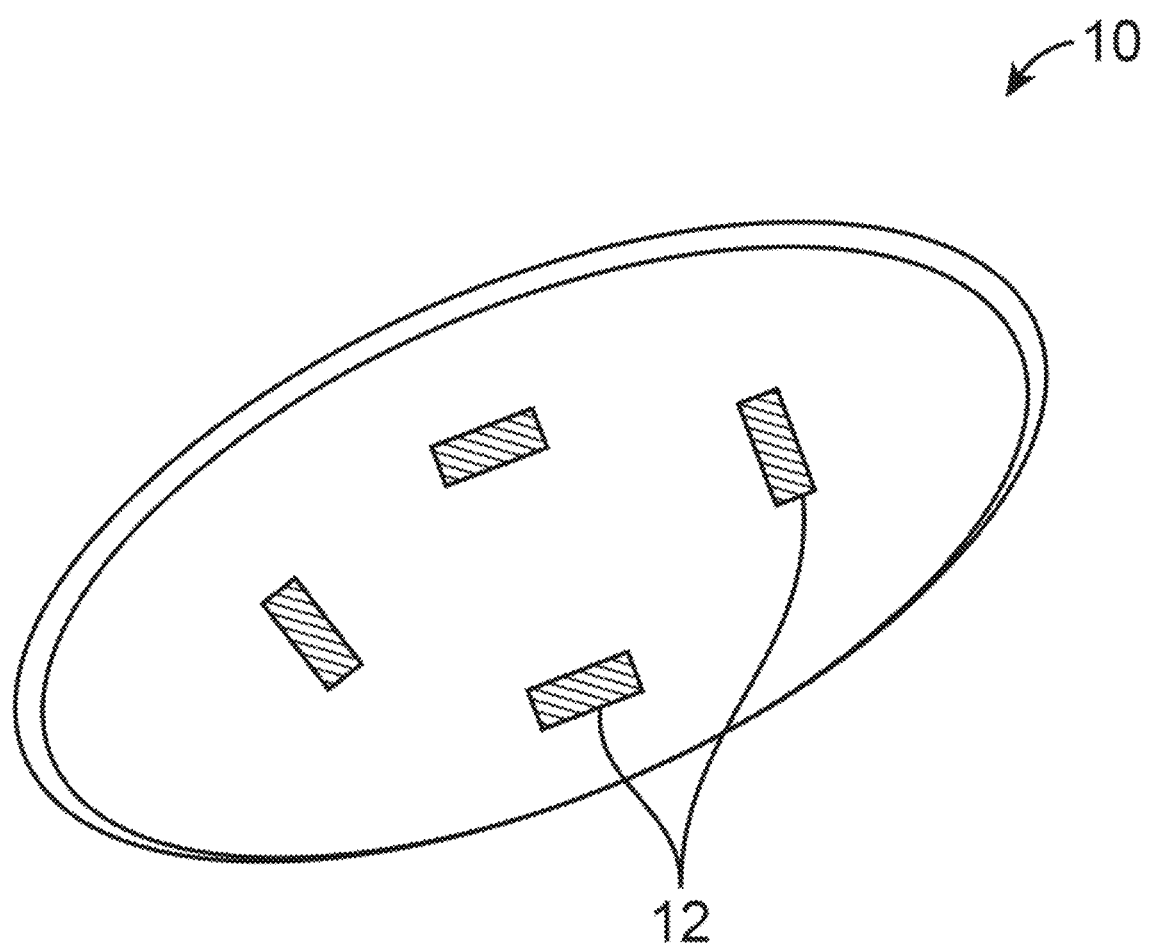
FIG. 2A shows OLED micro displays embedded into a soft contact lens, optically coupled with micro lens arrays for projecting images with myopic defocus on the periphery of the retina of a wearer, in accordance with some embodiments.

FIG. 2A shows OLED micro displays 12 mounted on the inner surface of a lens such as a soft contact lens 10, optically coupled with micro lens arrays for projecting images with defocus on the periphery of the retina of a wearer.

Figure 2B:
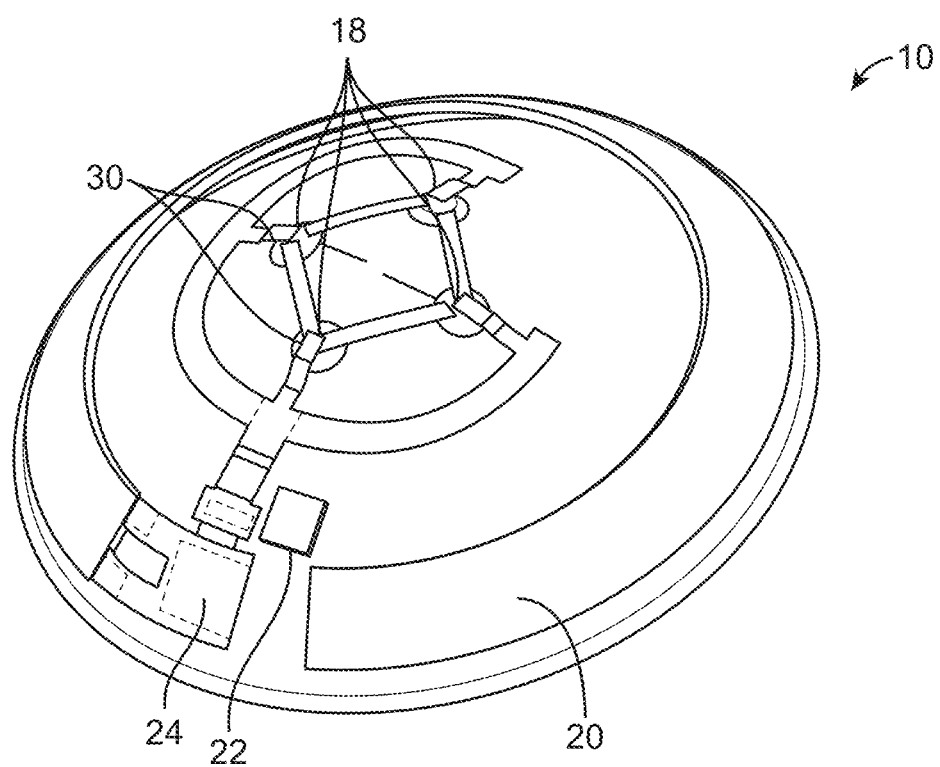
FIG. 2B shows a soft contact lens comprising a plurality of light sources and optics and associated circuitry, in accordance with some embodiments.

FIG. 2B shows a lens such as a soft contact lens 10 comprising a plurality of light sources and optics and associated circuitry, in accordance with some embodiments.

Although FIGS. 2A and 2B refer to a contact lens, the lens may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

The contact lens 10 comprises a plurality of projection units 18. Each of the plurality of projection units 18 comprises a light source and one or more optics to focus light in front of the retina as described herein. Each of the optics may comprise one or more of a mirror, a plurality of mirrors, a lens, a plurality of lenses, a diffractive optic, a Fresnel lens, a light pipe or a wave guide. The contact lens 10 may comprise a battery 20 and a sensor 22. The contact lens 10 may comprise a flex printed circuit board (PCB) 24, and a processor can be mounted on the PCB 24. The processor can be mounted on the PCB 24 and coupled to the sensor 22 and the plurality of light sources 30. The soft contact lens 10 may also comprise wireless communication circuitry and an antenna for inductively charging the contact lens 10. Although reference is made to a battery 20, the contact lens 10 may comprise any suitable energy storage device. The soft contact lens 10 may comprise a lens body composed of any suitable material such as a hydrogel. The hydrogel can encapsulate the components of the soft contact lens 10.

The processor can be configured with instructions to illuminate the retina with the plurality of light sources 30. The processor can be programmed in many ways, for example with instructions received with the wireless communication circuitry. The processor can receive instructions for a user mobile device.

The sensor 22 can be coupled to the processor to allow the user to control the contact lens 10. For example, the sensor 22 can be configured to respond to pressure, such as pressure from an eyelid. The processor can be coupled to the sensor 22 to detect user commands.

The electronic control system may comprise a processor such as an ASIC or a microcontroller, a rechargeable Lithium ion solid state battery, a voltage ramping module e.g., a buck boost converter, a flash memory and an EEPROM, an RFID module to provide wireless recharging, or an antenna preferably disposed radially near an edge of the contact lens 10, and any combination thereof. The contact lens 10 may comprise a biocompatible material, such as a soft hydrogel or silicone hydrogel material, and may comprise any material composition that has proven to be compatible with sustained wear on the eye 11 as a contact lens 10.

Figure 2C:
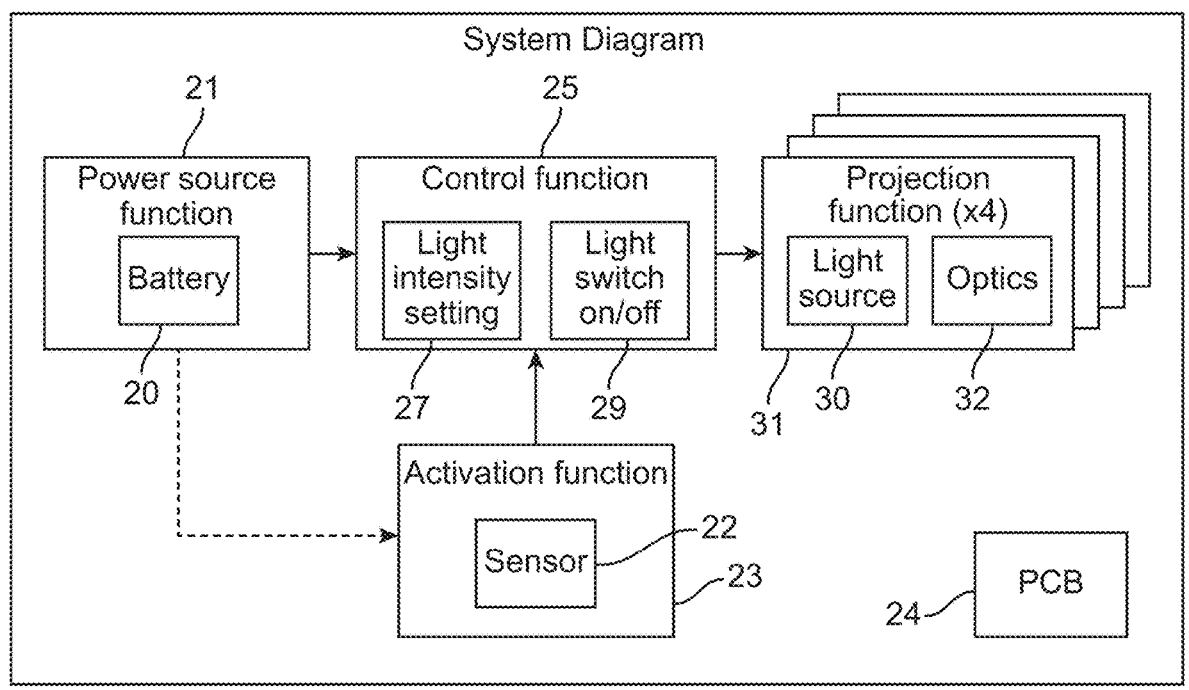
FIG. 2C shows a system diagram of the function of the components of the contact lens as in FIG. 2B.

FIG. 2C shows mechanical integration of the function of the components of the lens such as a contact lens 10 as in FIG. 2B. These components can be supported with the PCB 24. For example, the power source such as a battery 20 can be mounted on the PCB 24 and coupled to other components to provide a power source function 21. The sensor 22 can be configured to provide an activation function 23. The sensor 22 can be coupled to a processor mounted on the PCB 24 to provide a control function 25 of the contact lens 10. The control function 25 may comprise a light intensity setting 27 and a light switch 29. The processor can be configured to detect signal from the sensor 22 corresponding to an increase in intensity, a decrease in intensity, or an on/off signal from the sensor 22, for example with a coded sequence of signals from the sensor 22. The processor is coupled to the light projection units 18 which can comprise a light source 30 and optics 32 to provide the projection function 31. For example, the processor can be coupled to the plurality of light sources 30 to control each of the light sources 30 in response to user input to the sensor 22.

Optical Configurations and Projection Optics

Figure 3:
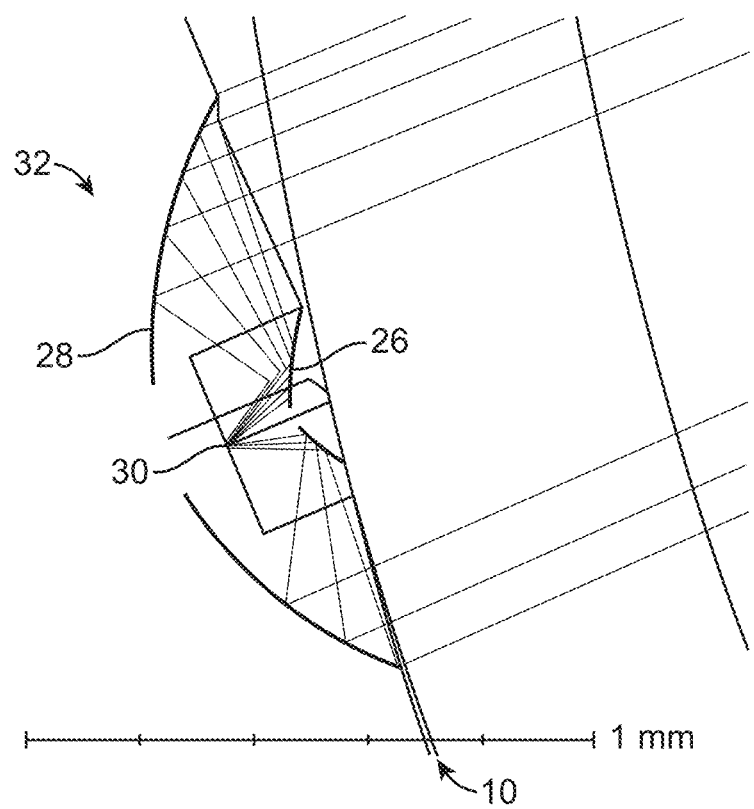
FIG. 3 shows an optical configuration in which the optical path length is increased by folding back the optical path using two mirrors, in accordance with some embodiments.
Figure 4:
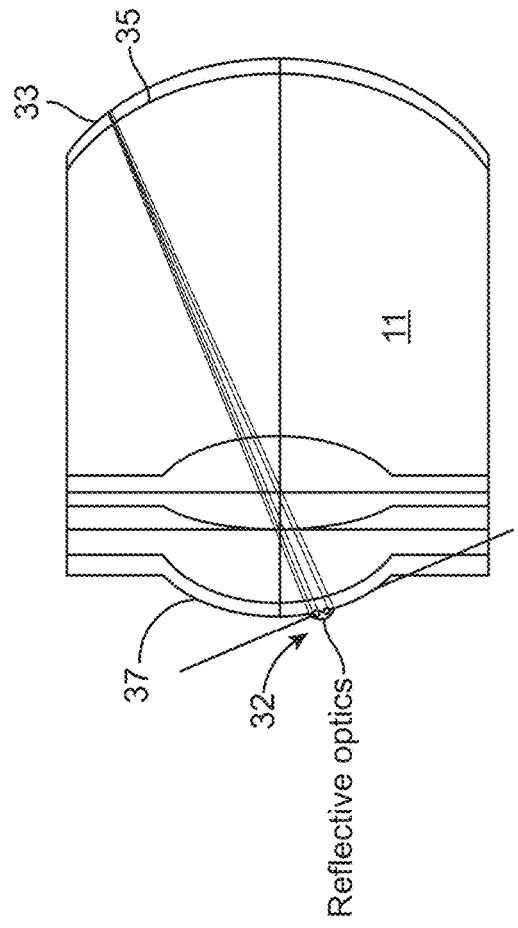
FIG. 4 shows a ray tracing simulation of the optical configuration shown in FIG. 3, in which the Liou Brennan eye model has been used to compute the retinal image, in accordance with some embodiments.

In some embodiments, the optic configuration 32 comprises a plurality of mirrors configured to collect light emitted by the micro-displays 12, then direct the light beam to the pupil of the eye 11, in order to form an eccentric retinal image, as shown in FIGS. 3 and 4. The mirrors may collimate the light beam, or direct the light beam toward the retina 33 with a suitable vergence so as to focus the light beam onto the retina 33.

Although the optic configurations shown in FIGS. 3 and 4 refer to a lens, such as a contact lens, a similar optical configuration can be used with a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens. Also, although reference is made to a myopic defocus, the defocus may comprise a hyperopic defocus, or an image focused onto the retina, for example.

The specifications of an exemplary optical configuration are shown in Table 2.

TABLE 2

Basic optic parameters of the optic configuration shown in FIG. 3.

| Characteristics | Value (Reflective Design) | Value (Single Lens Design) |
|---|---|---|
| Size of the light source | 10 microns | 10 microns |
| Diameter of the optic | 1.1 mm | 0.292 mm |
| Decentration of the light source from the center of the contact lens | 1.75 mm | 1.75 mm |
| Wavelength | 507 nm | 507 nm |
| Thickness of optic | 300 microns | 250 microns |
| Retinal image location | 27 degrees eccentric | 27 degrees eccentric |
| Size of the retinal image | 200 microns | 1100 microns |

A comparison of the simulated image size for the optic configuration shown in FIG. 3 and the retinal resolution at 27 degrees eccentricity shows that the peripheral retina 33 at this eccentricity will be able to perceive this image.

In some embodiments, three performance attributes of the optic configuration include one or more of:
1. Image magnification, controlling image resolution;
2. Depth of focus, controlled by the optical path length of the optic configuration; and
3. Diffraction, as measured by the Airy Diameter.

The mirror assembly shown in FIG. 3 achieves a depth of focus that is less than 1D, enabling the applied defocus of 2.0 to 4.0D or 2.0 to 7.0D to be clearly perceived by the peripheral retina 33 at the specified eccentricity (20 to 30 degrees or 10 to 40 degrees).

In some embodiments, the spots size of the image focused in front of the retina 33 comprises a resolution finer than the resolution of the retina 33. Retinal resolution generally decreases as a function of eccentricity. For example, at an angle of 0 degrees of eccentricity, retinal resolution is approximately 10 micrometers. At 5 degrees of eccentricity, the retinal resolution is approximately 30 micrometers. At 20 degrees of eccentricity, the resolution is approximately 100 micrometers and at 30 degrees the retinal resolution is approximately 150 micrometers.

Figure 5B:
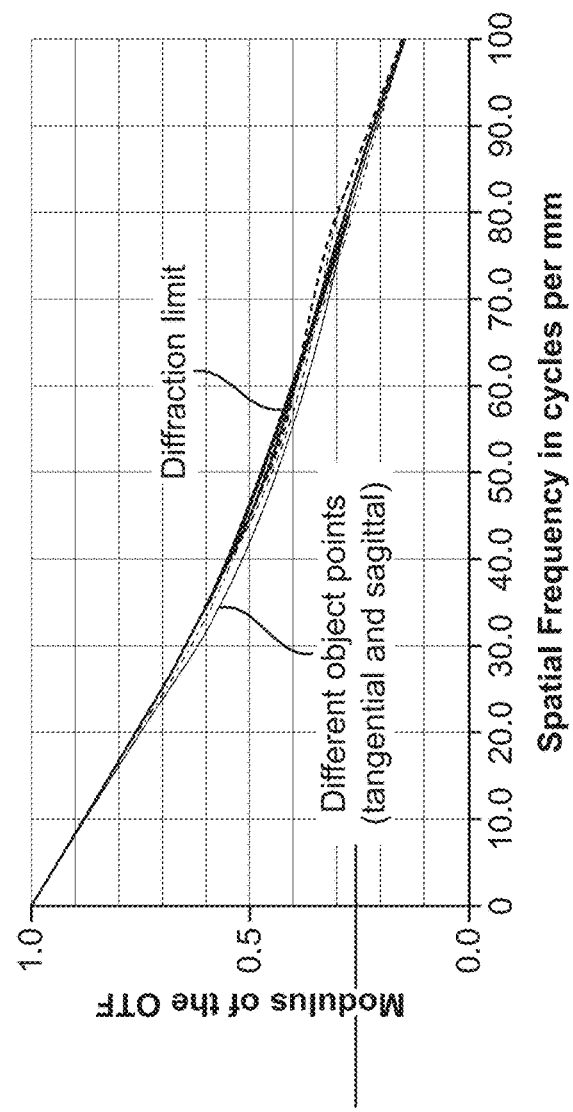
FIGS. 5A and 5B show analysis of retinal image quality generated by the optic configuration of FIG. 3.
Figure 5A:
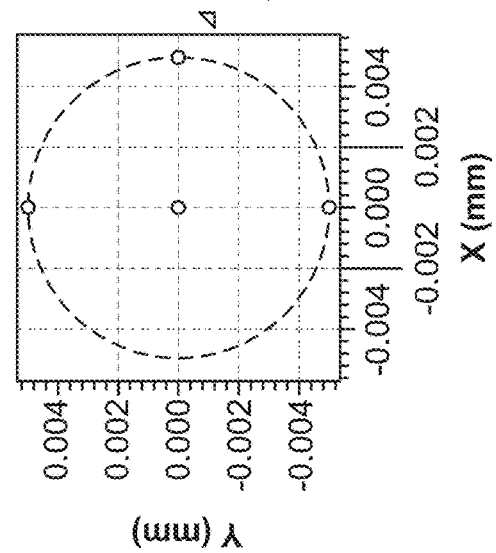

FIGS. 5A and 5B show analysis of retinal image quality generated by the optic configuration of FIG. 3. Images formed by three of the four light sources 30 have been simulated. The temporal point has been omitted because it is symmetrical to the nasal point. The analysis shows that the image quality exceeds the resolving power of the retina 33 at 27 degrees eccentricity. The modulation transfer function of the retinal image created by the mirror assembly of FIG. 3 is diffraction limited, indicating that aberrations of the optical elements deployed are not causing significant deterioration of image quality, in accordance with this embodiment. Furthermore, the spatial resolution of the optics exceeds the resolution of the retina 33 at the preferred image location.

FIG. 6 shows analysis of depth of focus of the optic configuration shown in FIG. 3. Each millimeter of distance from the retina 33 represents a defocus of 2.7D. This analysis shows that the depth of focus is sufficiently small that a defocus of 0.5 mm (1.35D) is perceivable by the retina 33 at the point of incidence of the image (27 degrees eccentricity). Depth of focus depends on effective path length of the stimulating beam.

FIG. 7 shows the plot of MTF values against defocus shows the depth of focus of image created by each of the light sources (object).

A second embodiment comprises optics 32 comprising a converging or collimating lens in optical coupling with light source 30, as shown in FIGS. 8A and 8B. In this configuration a lens 34, which may comprise a single lens, is used to collimate the light output from the stimulation source and direct it to the cornea 37 through the lens such as contact lens 10. Although reference is made to a contact lens, the lens 10 may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

The effectiveness of the collimating lens 34 depends on its refractive index and should be sufficiently high in order to create a substantial difference in refractive indices between the lens material and the material of the contact lens 10 that functions as the substrate. In this example, the refractive index of the embedded lens 34 has been assumed to be 2.02 (e.g., refractive index of a lanthanum fluorosilicate glass $LaSF_5$), although other materials may be used.

Optical performance of the embodiment of FIGS. 8A and 8B is shown in FIGS. 9 and 10. Images formed by three of the four light sources 30 have been simulated. The temporal point has been omitted because it is symmetrical to the nasal point. Each millimeter of distance from the retina 33 represents a defocus of 2.7D. This analysis shows that the depth of focus is substantially higher than ID, so that image blur caused by a defocus of 0.5 mm (1.35D) may not be perceivable by the retina 33 at the point of incidence of the image (27 degrees eccentricity).

The analysis shows that the image quality exceeds the resolving power of the retina 33 at 27 degrees eccentricity. The optical path length of the single lens design is much shorter in this case, therefore, image magnification is substantially higher (110×, as opposed to 8× or 20× for the reflective design.). The spatial frequency resolution at 50% contrast (Modulus of OTF) is lower, approximately 15 line pairs per millimeter ("lp/mm"), compared with 50 lp/mm for the reflective design. Depth of focus has been estimated for this embodiment, again using Liou Brennan eye model to simulate the ocular optics, including ocular aberrations, as shown in FIG. 10. The depth of focus is greater than 1.0 D, indicating that changes in image resolution as a function of defocus may not be easily perceivable by the peripheral retina 33, especially since the resolution capability of the retina 33 at that eccentricity (20 to 30 degrees or 10 to 30 degrees), derived mainly from rods is relatively poor as described herein.

A third embodiment comprises a light-pipe 36 in order to increase the optical path length, as shown in FIGS. 11A and 11B. The light-pipe 36 can provide an increased optical path length to decrease image magnification and retinal image size. However, depth of focus is relatively large, and the resolution is relatively coarse (15 lp/mm at 50% MTF).

Although reference is made to a light pipe 36 on a cornea 37 as would occur with a contact lens, the lens combined with the light pipe 36 may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

Numerous other optical configurations may be used, including the use of a micro-lens array with a point source, use of diffractive optics in order to use a thinner lens, generation of multiple retinal images using a single point source and an optical processing unit. In all case, the three characteristics listed above may be used as metrics in order to evaluate the suitability of a particular design.

Each embodiment disclosed herein can be combined with any one or more of the other embodiments disclosed herein, and a person of ordinary skill in the art will recognize many such combinations as being within the scope of the present disclosure.

Exemplary Lens Embodiments

The presently disclosed methods and apparatus are well suited for combination with many types of lenses, such as one or more of: smart contact lenses, contact lenses with antennas and sensors, contact lenses with integrated pulse oximeters, contact lenses with phase map displays, electro-optic contact lenses, contact lenses with flexible conductors, autonomous eye tracking contact lenses, electrochromic contact lenses, dynamic diffractive liquid crystal lenses, automatic accommodation lenses, image display lenses with programmable phase maps, lenses with tear activated micro batteries, tear film sensing contact lenses, lenses with multi-colored LED arrays, contact lenses with capacitive sensing, lenses to detect overlap of an ophthalmic device by an eyelid, lenses with active accommodation, lenses with electrochemical sensors, lenses with enzymes and sensors, lenses including dynamic visual field modulation, lenses for measuring pyruvate, lenses for measuring urea, lenses for measuring glucose, lenses with tear fluid conductivity sensors, lenses with near eye displays with phase maps, or lenses with electrochemical sensor chips.

Figure 12:
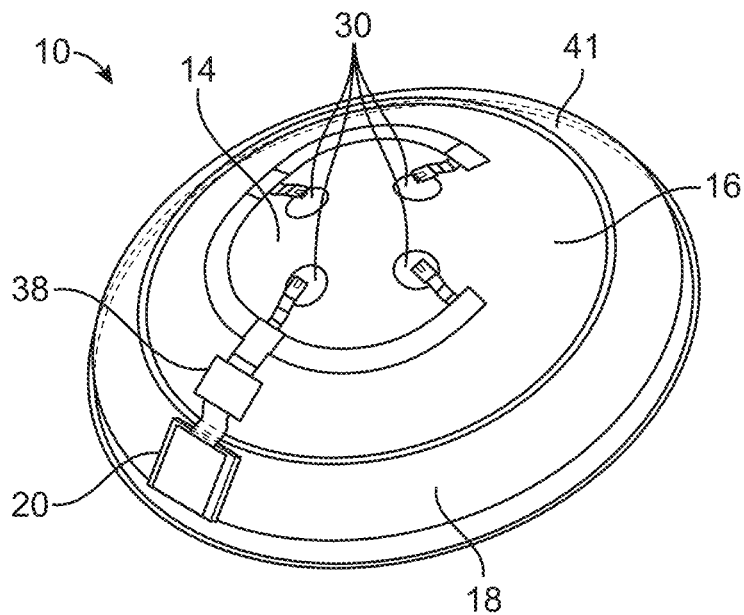
FIG. 12 shows soft contact lens with embedded light sources, optics and electronics, in accordance with some embodiments.

A lens such as a soft contact lens 10 is shown in FIG. 12. Although reference is made to a contact lens, the lens 10 may comprise a lens of one or more of a projector, an ophthalmic equipment, a TV screen, a computer screen, a handheld device such as a smart phone, a wearable device such as a spectacle lens, a near eye display, a head-mounted display, a goggle, a contact lens, a corneal onlay, a corneal inlay, a corneal prosthesis, or an intraocular lens.

This contact lens 10 comprises a base or carrier contact lens comprising embedded electronics and optics. The base soft contact lens 10 is made of a biocompatible material such as a hydrogel or a silicone hydrogel polymer designed to be comfortable for sustained wear. In some embodiments, the contact lens 10 has a central optical zone 14 of diameter within a range from 6 mm to 9 mm, for example within a range from 7.0 mm to 8.0 mm. The central optical zone 14 is circumscribed by an outer annular zone, such as a peripheral zone 16 of width in a range 2.5 mm to 3.0 mm. The outer annular zone is surrounded by an outermost edge zone 18 of width in the range from 0.5 mm to 1.0 mm. The optical zone 14 is configured to provide refractive correction and can be spherical, toric or multifocal in design, for example. The outer annular zone peripheral to the optical zone 14 is configured to fit the corneal curvature and may comprise rotational stabilization zones for translational and rotational stability, while allowing movement of the contact lens 10 on the eye 11 following blinks. The edge zone 18 may comprise a thickness within a range from 0.05 mm to 0.15 mm and may end in a wedge shape. The overall diameter of the soft contact lens 10 can be within a range from 12.5 mm to 15.0 mm, for example within a range from 13.5 mm to 14.8 mm.

The embedded light sources 30 and the electronics are preferably located in the outer annular zone of the contact lens 10, as shown in FIG. 12. The central optical zone 14 is preferably free from electronics and light sources 30 in order to not compromise the quality of central foveal or macular vision, in accordance with some embodiments. In some embodiments, the edge zone 18 does not comprise circuitry in order to maintain contact with the corneal surface and provide comfort.

The light sources can be arranged in many ways on the contact lens. For example, the light sources can be arranged in a substantially continuous ring around the central optical zone. In some embodiments, the plurality of light sources and the plurality of optics (e.g., lenses, mirrors or light guides) are coupled together to form a continuous ring of illumination.

The contact lens 10 of FIG. 12 comprises of a body composed of a soft biocompatible polymer with high oxygen permeability embedded with a transparent film populated with all the electronic and optical components. This transparent film may comprise a transparent printed circuit board ("PCB") substrate. The thickness of the PCB can be within a range from about 5 microns to 50 microns and may comprise a plurality of layers of the film in order to utilize both surfaces of the PCB substrate for population of electronics. The PCB substrate can be curved to conform to the geometry of the base contact lens 10, with a curvature within a range about 7.5 mm to about 10.0 mm, for example within a range from about 8.0 mm to about 9.5 mm, for example. The PCB substrate can be configured for suitable oxygen permeability. In some embodiments, the PCB is perforated to improve permeability of oxygen, tear fluid, nutrients and carbon dioxide through it. In some embodiments, the PCB has a low tensile modulus, for example within a range from about 1 MPa to about 50 MPa, although stiffer films may also be used for example. In some embodiments, a preferred material for a transparent flexible PCB substrate comprises a polyimide that is cast from a liquid or a solution, and may be in the form of a polyamic acid when spin cast on a flat substrate, subsequently cured thermally to form a polyimide such as Kapton™.

The contact lens 10 may comprise one or more components shown in FIG. 12. The architecture of the electronic system, shown in FIG. 12 comprises a plurality of light sources 30 mounted on a bus, a microcontroller 38 that comprises a power and data management system, an onboard memory and an RFID module, a sensor that is designed to detect a physical or physiological trigger and issue a signal that turns the light sources 30 ON or OFF, an antenna 41 for wireless exchange of data that also functions as a wireless receiver of power, operating on a single or multiple frequency bands for transmission of data and power and a rechargeable solid state Lithium ion battery 20. In some embodiments, the microcontroller 38 comprises an application specific integrated circuitry ("ASIC"). The plurality of light sources 30 may comprise microscopic light sources 30 as described herein.

The light sources 30 can be positioned along a circumference of diameter in the range 1.5 mm to 5.0 mm from the center.

Figure 13:
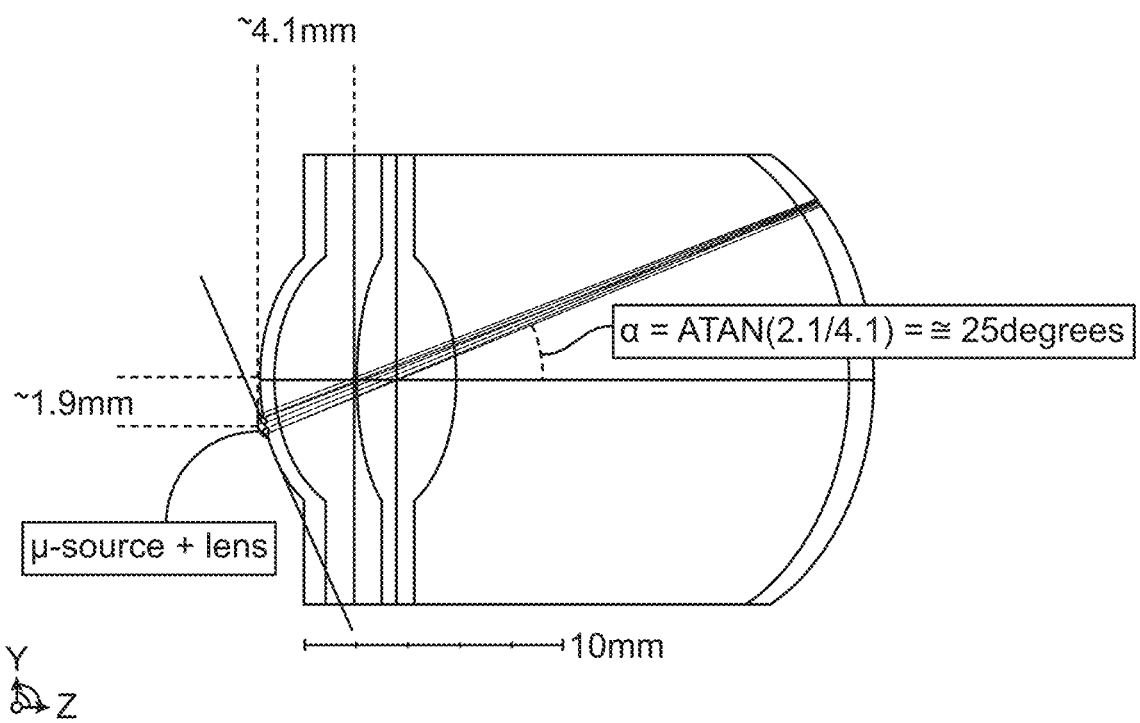
FIG. 13 shows a ray tracing simulation of the peripheral retinal image formed by a combination of a microscopic light source and a micro-optic, in accordance with some embodiments.

FIG. 13 shows a ray tracing analysis of the image of a light source 30 formed on an outer region of the retina 33 such as the peripheral retina 33. In this simulation, the anterior chamber depth is assumed to be 4.1 mm, typically between 2.9 mm and 5.0 mm for human subjects, the axial length has been assumed to be 25.0 mm, and the contact lens 10 is positioned on the cornea. The microscopic light source 30 is placed 1.9 mm away from the center of the contact lens 10, leaving a central optical zone 14 of 3.8 mm in diameter that is clear.

Referring again to FIGS. 12 and 13, a combination of a light source 30 and a lens such as a micro-lens can be used to direct light to an outer region of the retina 33. The micro-lens can be configured to collect light emitted by the light source 30. The collected light can be one or more of collimated or focused and directed to the pupil of the eye 11. In some embodiments, a projection system comprises the combination of the microlight source 30 and the image forming optics 32.

The light source 30 may comprise one or more of an organic light emitting diode (OLED), a quantum dot light emitting diode (QLED), a transparent light emitting diode (TOLED), an inorganic light emitting diode (i-LED), a CRT display, or a Vertical Cavity Surface Emitting Laser (VCSEL). The light source 30 may comprise one or more pixels, populated on a transparent or opaque substrate. The light source 30 may comprise one or more display components such as a passive matrix or an active matrix, for example. In some embodiments, a size of individual pixels is within a range from 1 to 10 microns, for example within a range from 2 to 5 microns. The brightness of each of the plurality of pixels when turned ON can be more than 500 nits ($Cd/m^2$), more than 5000 nits, or within a range from 10,000 to 25,000 nits.

The resolving power of the retina 33 is highest at the center, the fovea. Healthy young persons are capable of angular resolution of 0.6 arc minute, equivalent to 20/12 in Snellen terminology. Resolution capability is typically reduced to 20/200 (10 arc minute) at 25 degrees eccentricity. There are few if any cones at this eccentricity, and the population of rods is also much diminished.

In some embodiments, the image delivery system provides an image resolution equal or exceeding the level of retinal image resolution. In some embodiments, there is no additional benefit can be expected if the projected image resolution exceeds the resolution capability of the retina 33 at the location of the image. In some embodiments, the spot size of the image at the retinal periphery is therefore 150 microns or less.

The wavelengths of light emitted by the light source 30 can be configured in many ways. The wavelength of light emitted by the light source 30 can be determined by clinical studies in accordance with the present disclosure. In some embodiments, the wavelength of the light source 30 comprises light that corresponds to the peak sensitivity of retinal photoreceptors at the desired eccentricity, e.g. substantially matches the peak sensitivity. In some embodiments light is projected at an eccentricity of 10 to 30 degrees, such as 20 to 30 degrees, where rods are predominant, and the light from the source comprises wavelengths within a range from about from about 410 nm to 600 nm, such as 420 nm to 600 nm, for example from about 490 nm to 530 nm, for example within a range from about 500 to 520 nm, for example from about 502 to 512 nm. In some of the wavelength simulations disclosed herein 507 nm light is used as the input wavelength parameter. The optical designs disclosed herein are applicable to all wavelengths, even though the precise results of optimized design parameters may change with wavelength, due to chromatic dispersion of the material comprising the projection unit.

Work in relation to the present disclosure suggest that two design constraints may influence the selection of design input parameters in some of the embodiments that follow. These are:

1. Dimensions of the projection unit 18, so that they can be embedded into the contact lens 10 without the lens thickness being too high. In some embodiments, the maximum lens thickness in the outer annular zone is 400 microns, which is consistent with current soft contact lenses for refractive corrections.
2. Optical path length between the microscopic light source 30 and the image forming system. This is related to control of image magnification and magnitude of image blur caused by diffraction, which can be quantified as the Airy Disk diameter. Image magnification is given by the ratio of the focal length of the image projection unit to the focal length of the eye 11, which is generally assumed to be 17 mm for first order estimates. In some embodiments, it is specific to the individual eye. In some embodiments, the Airy disk diameter, (2.44×λ(in microns)×f/#) is no more than the retinal resolution limit at image location. For example, the minimum spot size at eccentricity of 25 degrees is 150 microns, so the Airy Disk diameter should not exceed 150 microns and can be less than 150 microns. Since the focal length of the eye 11 is fixed, the aperture of the projection optic controls the Airy Disk diameter at any wavelength.

In some embodiments, size of the Airy Disk of the collection optics and light sources 30 and associated image as described herein is related to the retinal image resolution.

For example, at 30 degrees, 25 degrees, 20 degrees, 15 degrees and 10 degrees, the Airy Disk size may be no more than about 150 micro-meters ("microns", "um") about 125 um, about 100 um, about 75 um, and about 60 um, respectively.

The image forming system can be configured in many ways including without limitation, diffractive optical elements, Fresnel lenses, refractive optics or reflective optics.

The following simulations provide optical results in accordance with some embodiments disclosed herein.

TABLE 3

Input parameters of the second optical simulations.

| Optical Component or property | Value |
| --- | --- |
| Size of Light Source | 10 microns |
| Max Thickness of the light projection unit | 300 microns |
| Image location on the retinal periphery | 27° eccentric to the fovea |
| Diameter of the projection unit | 1.1 mm |
| Optic design | Aspheric $8^{th}$ order, $4^{th}$ order Zernike polynomials |
| Offset between the center of the contact lens and the light projection unit | 1.75 mm |
| Wavelength of Light | 507 nm |

Figure 14:
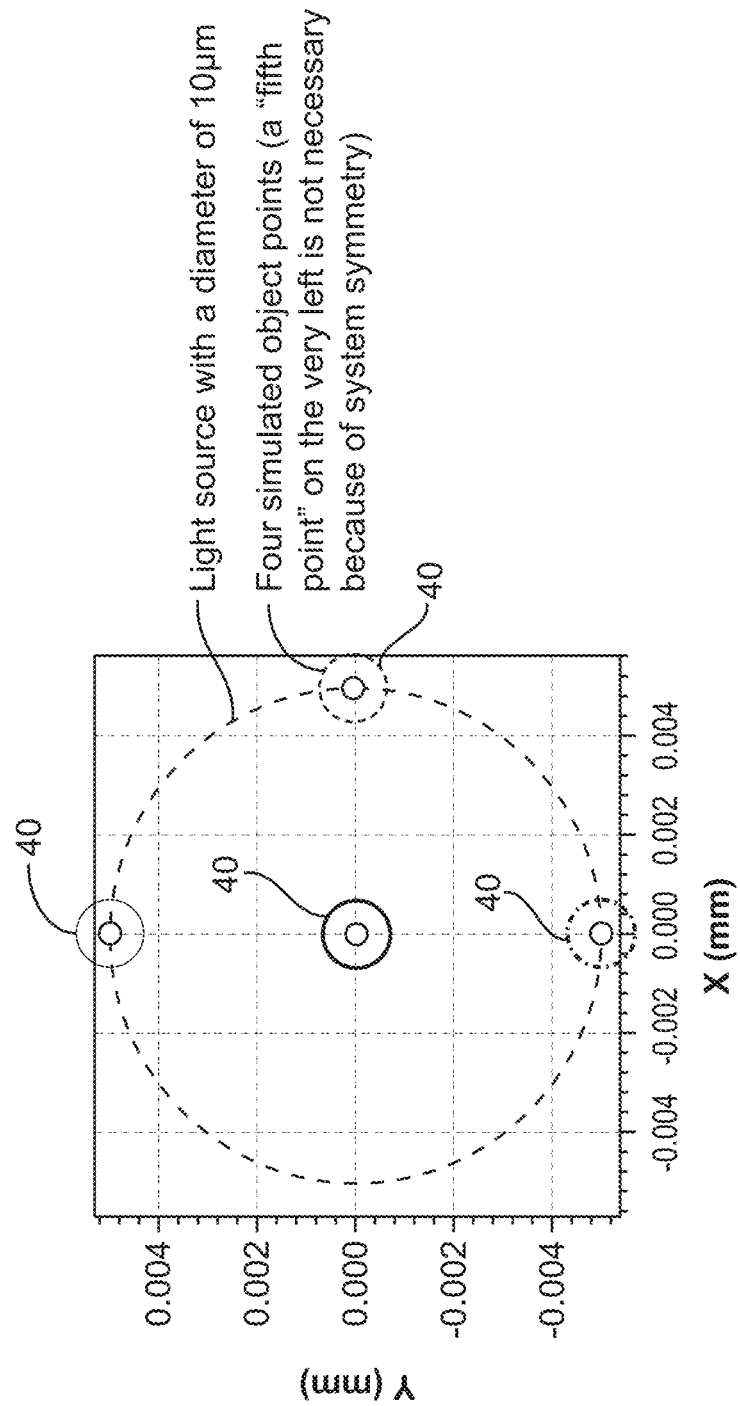
FIG. 14 shows four object points used to simulate image quality using ray tracing for a light source comprising four simulated object points, in accordance with some embodiments.

In some embodiments, the area covered by the overall image is preferably an arcuate segment of 5-10 degrees by 30-45 degrees, or 150-450 degree$^2$ for every light source, or about 3.0-6.0 mm$^2$ in area. In some embodiments, four such light sources 30 at each quadrant of the contact lens 10 deliver four such peripheral images for optimum neurostimulation to the retina 33. An embodiment in accordance with the second simulations of the image delivery system is shown in FIG. 3. In this embodiment, a system of convex 26 and concave 28 micro-mirrors is used to increase optical path length and thereby image magnification of the peripheral retinal image. FIG. 4 shows the light path of the peripheral image through the eye 11 for this embodiment. An exemplary light source 30 can be defined, assuming that the diameter of the light source 30 is 10 μm, and thickness is 100 μm. Four object points 40 can be specified to simulate the image quality, as shown in FIG. 14. With reference to FIG. 14, the simulated light source 30 is shown with the dashed circle of 10 μm and the simulated object points 40 includes the smaller circles and the center points of each of the smaller circles. Table 3 shows the input parameters of the simulation.

Figure 15:
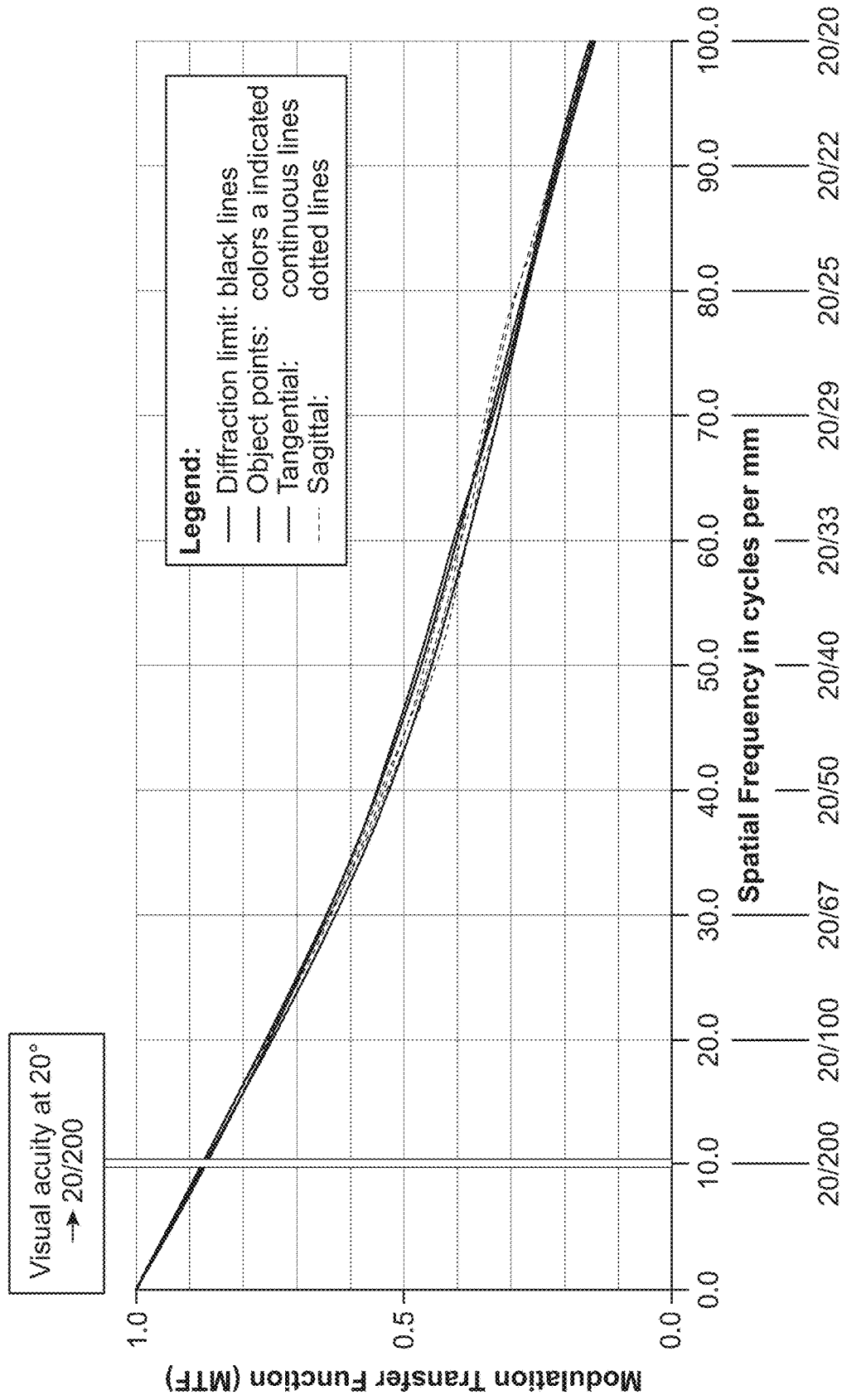
FIG. 15 shows the quality of a peripheral image generated by a reflective optic, in which Modulation transfer functions (MTF) of all the object points are substantially coincident, in accordance with some embodiments.

Output of the simulation are: Image magnification and size, Image quality and Depth of focus. The same input and output parameters were used to simulate all the preferred embodiments. Image size of the first preferred embodiment was found to be 200 microns, image magnification being 20×. Results of simulation of image quality is shown in FIG. 15 for this simulation. All MTF plots are virtually coincident. The MTF plots indicate that the resolution of the peripheral image is substantially better than the limits of retinal resolution at this eccentricity.

Figure 16:
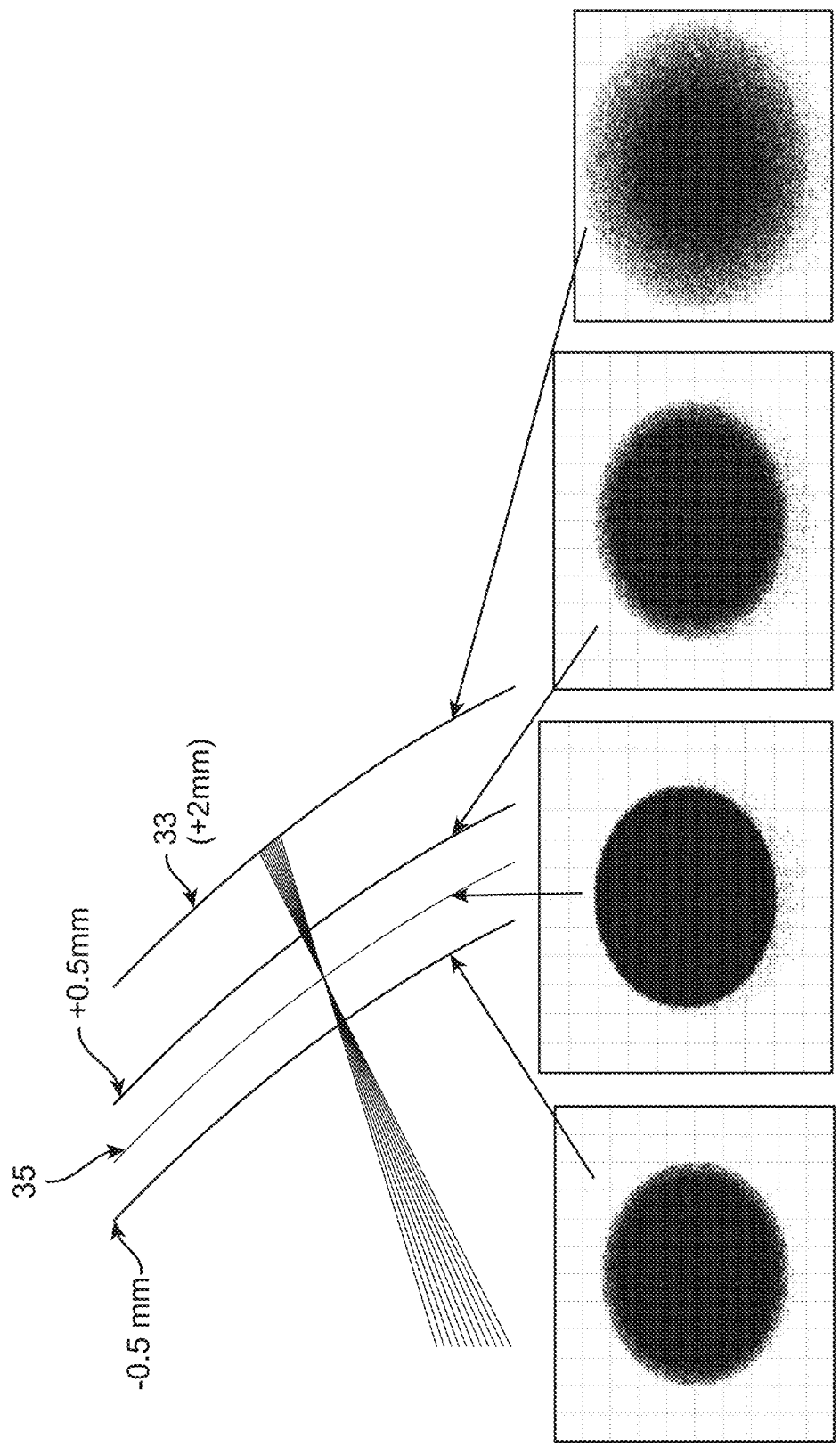
FIG. 16 shows depth of focus of the peripheral image formed by the reflective optic, in accordance with some embodiments.

The depth of focus of the peripheral image was also simulated for the reflective optic in the second simulations and is shown in FIG. 16. In some embodiments, the image is optimally formed at a distance of 2.0 mm in front of the retina 33, causing it to be myopically defocused on the retina 33. In some embodiments, the blur induced by this myopic defocus overcomes the effect of depth of focus, so that the retina 33 perceives a blurred image for it to perceive a neurostimulation to move forward, reducing the axial length of the eye 11. In some embodiments, the neural stimulation is sufficient to decrease axial growth of the eye 11.

Figure 17:
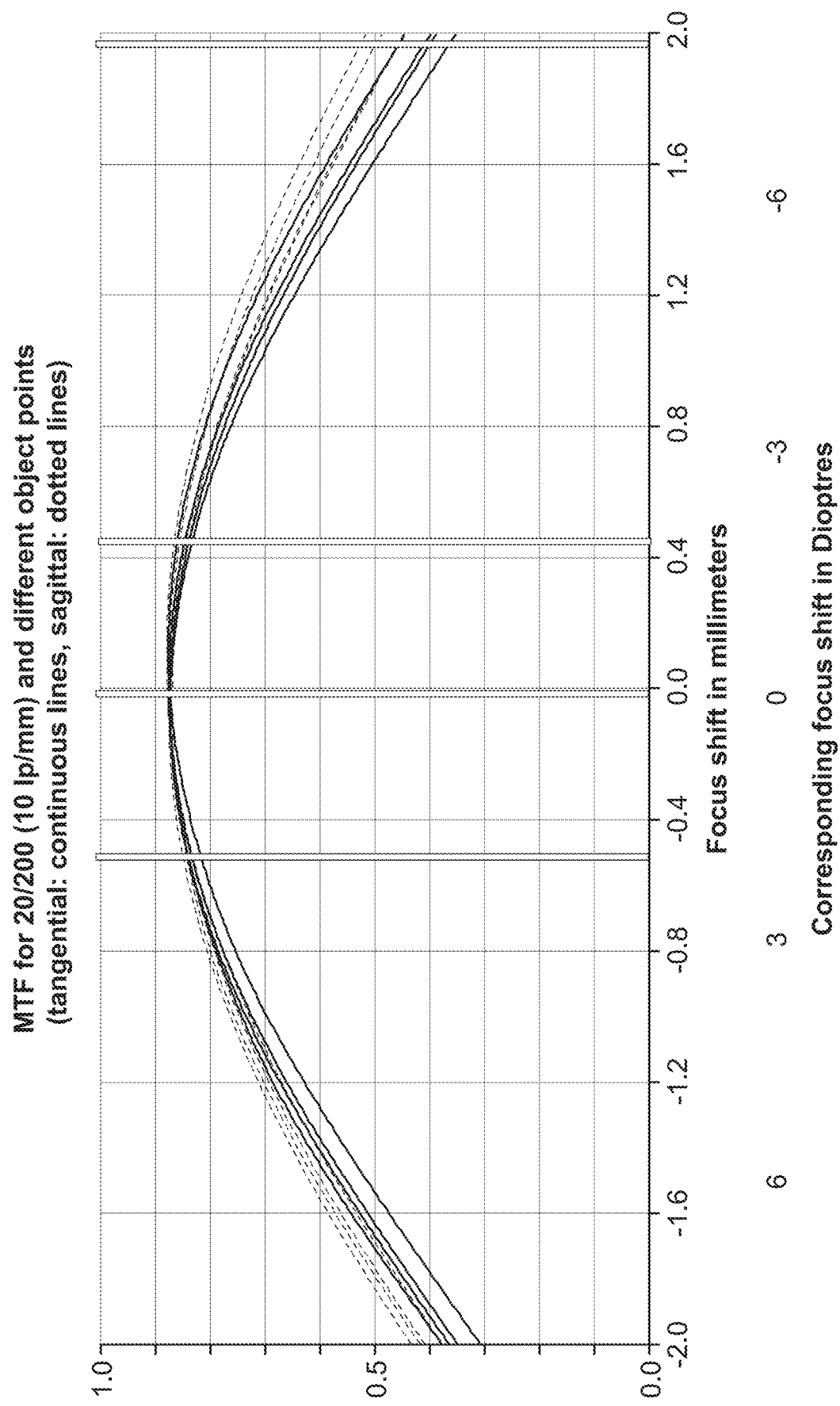
FIG. 17 shows the effect of myopic blur on image resolution of the peripheral retinal image formed by the reflective optic, as measured by change of the magnitude of MTF at a single spatial frequency (20/200 or 10 line pair per mm "lp/mm" or 10 arc min) as a function of the magnitude of myopic defocus for the reflective optical design, in accordance with some embodiments.

FIG. 17 shows the effect of image blur caused by myopic defocus in the form of loss of contrast or the modulus of simulated MTF plots shown for a particular spatial frequency (20/200 or 10 arc minutes) for the second simulations. The increase in spot size shown in FIG. 16 is reflected in and consistent with the loss of the magnitude of the MTF plots as a function of the magnitude of myopic defocus. The second simulations indicate that the focal length of the projection unit is 0.85 mm with an image size 200 microns and an image magnification is 20×. The Airy disk diameter is computed to be 8.9 microns, while the Raleigh criterion is 10.9 microns.

Referring again FIGS. 8A and 8B which show a lens to collect light from the light source 30 and direct light toward the retina 33, and the path of light along the eye 11, respectively. In some embodiments, the light source 30 faces a refractive lens that approximately collimates the light which is finally projected in front of the peripheral retina 33, creating a myopic defocus of the peripheral image. Although reference is made to a refractive lens, other lenses can be used such as diffractive optics and gradient index (GRIN) lenses. Table 4 shows the design parameters of the refractive lens used for the third simulations of the peripheral image.

TABLE 4

Design input parameters of the third simulations.

| Lens Parameters | Value |
| --- | --- |
| Diameter of the light source | 10 microns |
| Wavelength used for simulation | 507 nm |
| Diameter of the optic | 292 microns |
| Thickness of the optic | 250 microns |
| Refractive index of the micro-lens | 2.2 |
| Image location on the retina | 27 degrees eccentric |
| Thickness of the projection optic | 350 microns |
| Distance of light source from center of contact lens | 1.75 mm |
| Collimating lens design | $14^{th}$ order aspheric |

Figure 18:
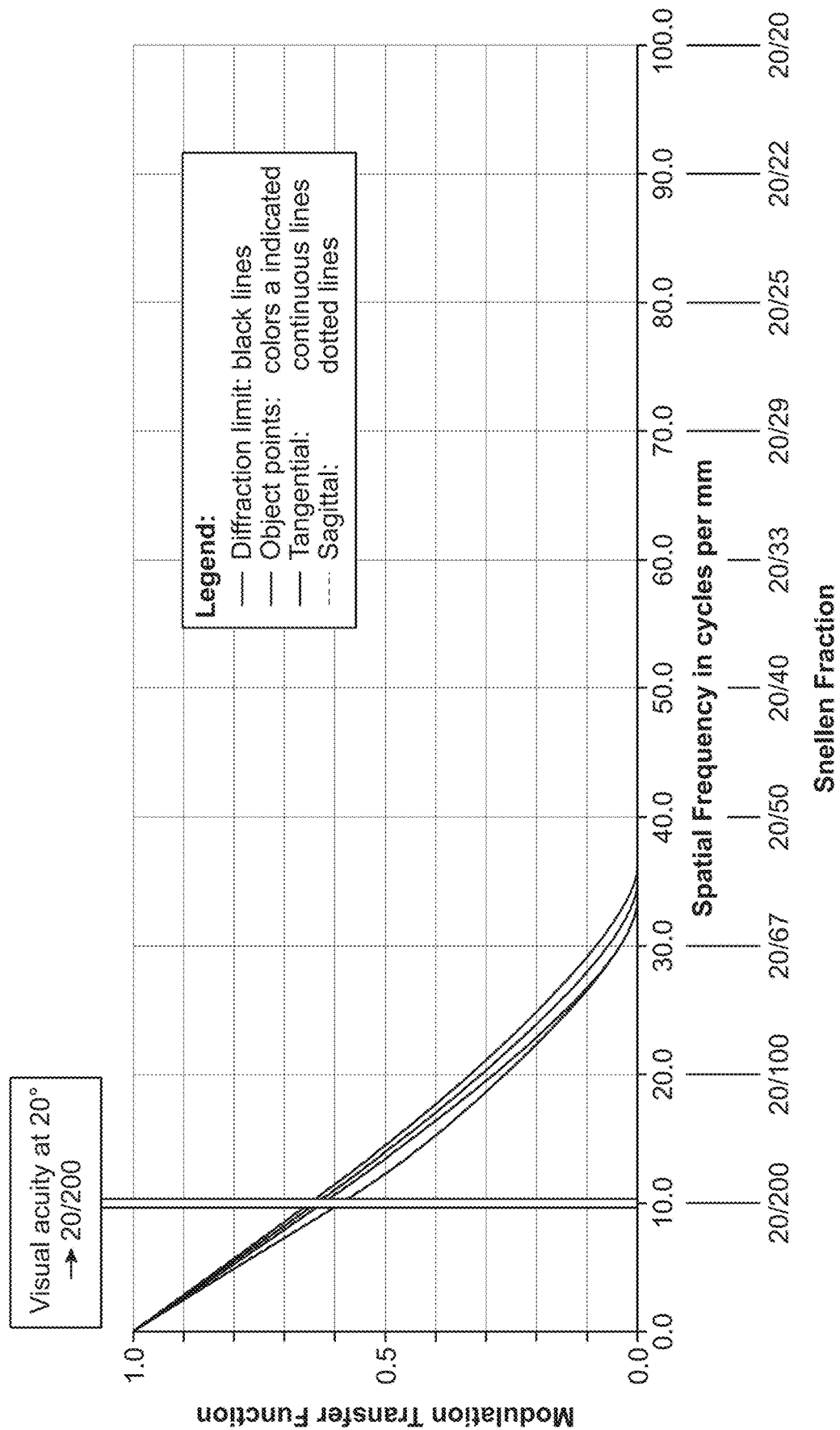
FIG. 18 shows MTF plots of the retinal image formed by the refractive optic for the four object points shown in FIG. 14, in accordance with some embodiments.
Figure 19:
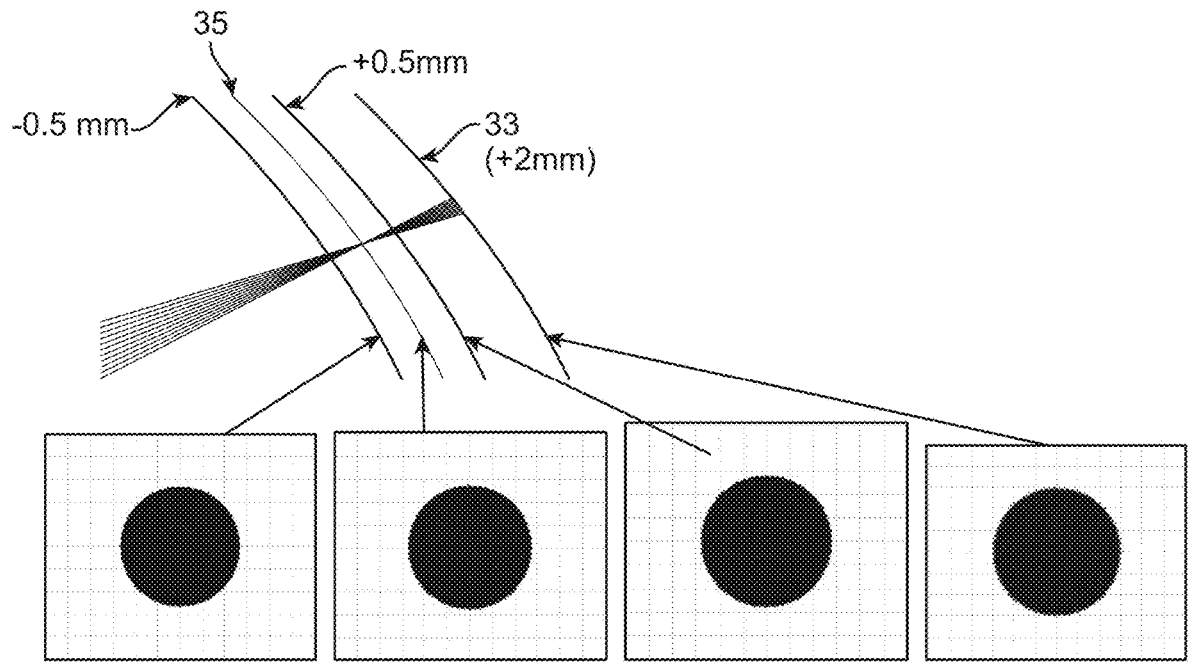
FIG. 19 shows depth of focus of the image formed by the refractive optic, in accordance with some embodiments.
Figure 20:
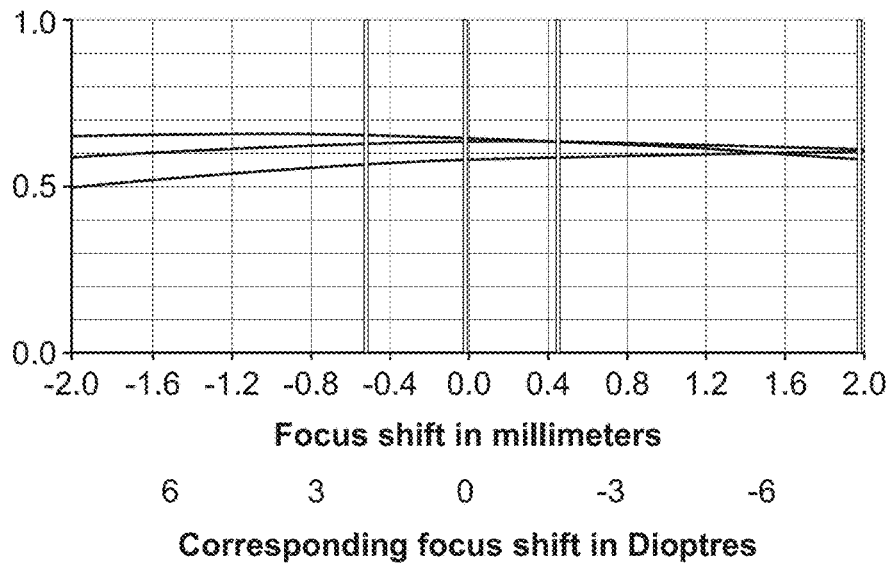
FIG. 20 shows MTF computed for a single spatial frequency (20/200 or 10 lp/mm, or 10 arc min) as a function of myopic defocus, in accordance with some embodiments.
Figure 21:
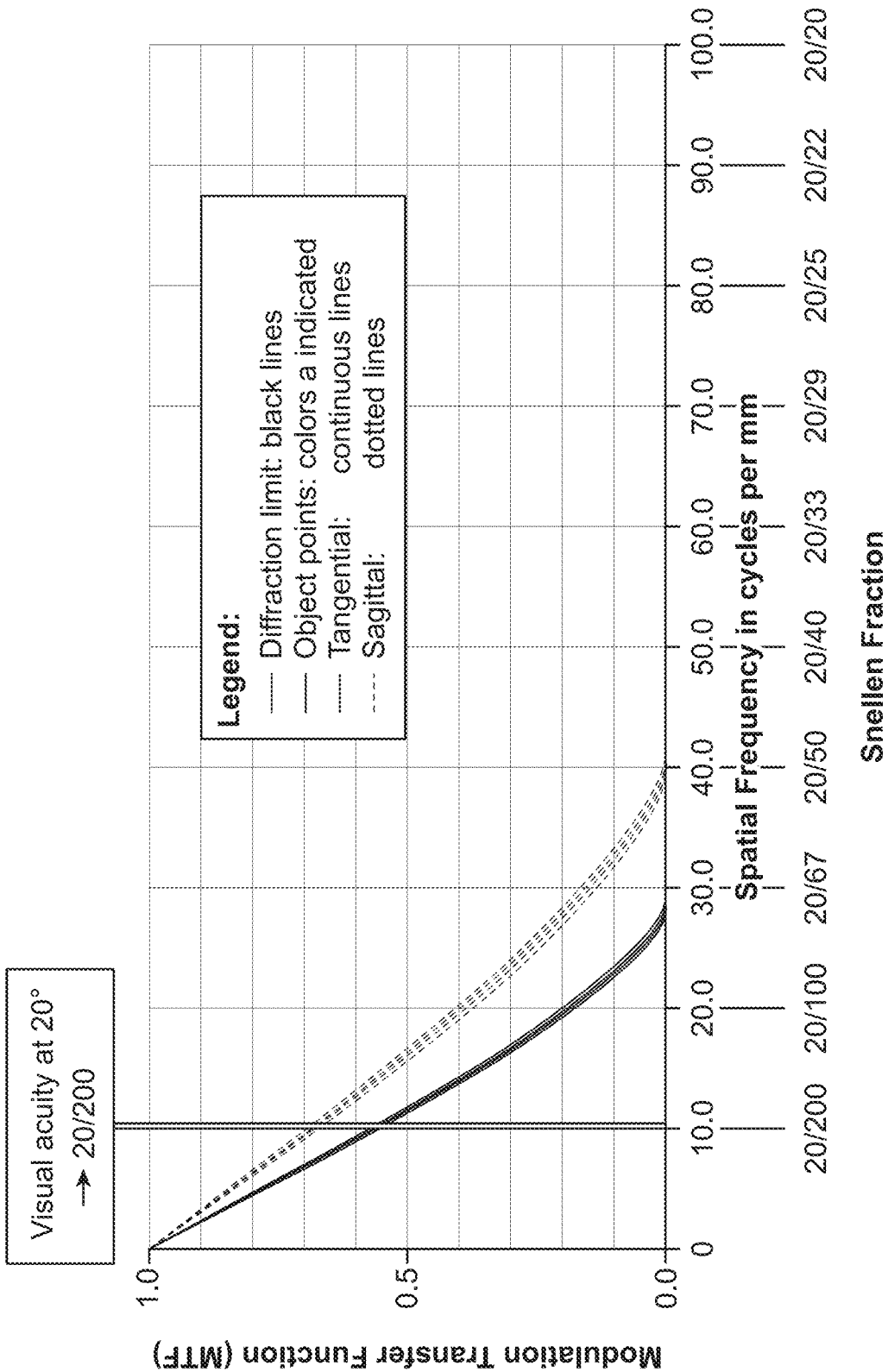
FIG. 21 shows MTF plots of the four object points in FIG. 14 for embodiments comprising a miniature lightguide, in which a substantial difference in image quality exists between sagittal and tangential planes, indicating non-symmetrical aberrations, in accordance with some embodiments.
Figure 22:
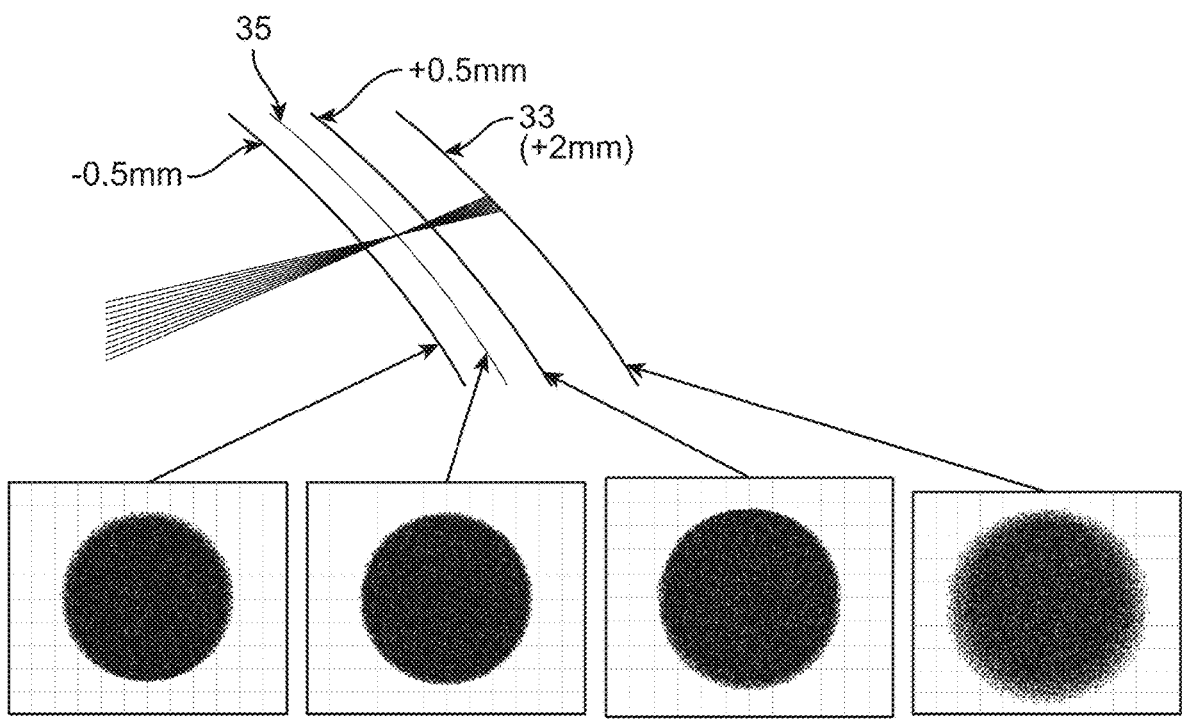
FIG. 22. Depth of focus of the peripheral retinal image projected by the lightguide optic, in accordance with some embodiments.
Figure 23:
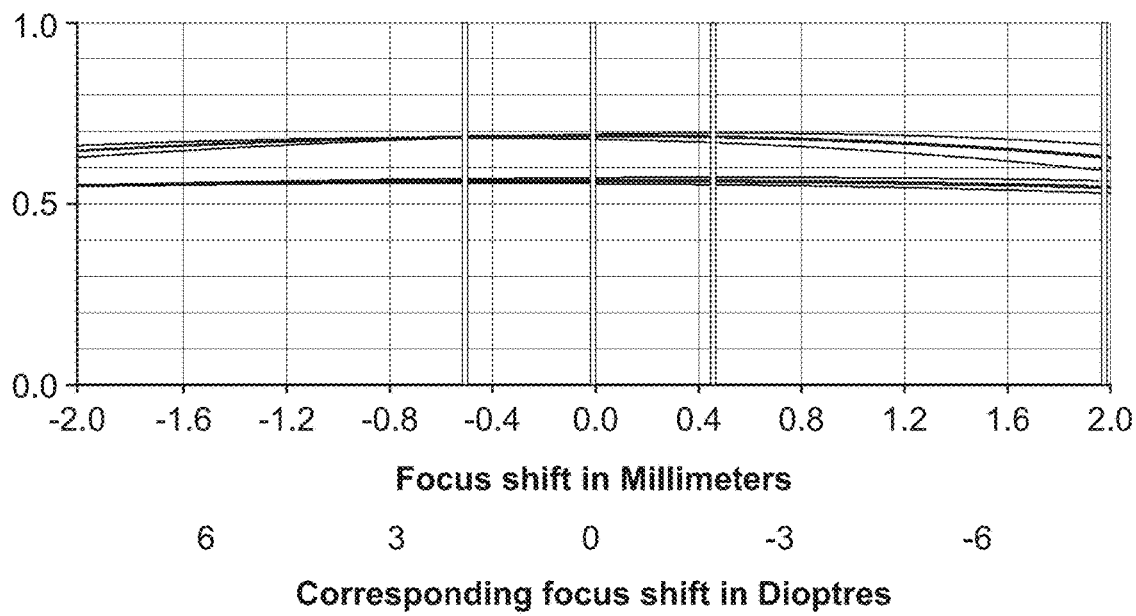
FIG. 23 shows MTF plots at a single spatial frequency (20/200) plotted against the magnitude of myopic defocus of the peripheral image on the retina for embodiments with light guides.

The results of these simulations show that the image size is 1100 microns with an image magnification of 110. The MTF plots are shown in FIG. 18 for the four object points 40 shown in FIG. 14. The magnitude of MTF plots at high spatial frequencies are substantially lower than those for the reflective optic. The MTF plots show that image resolution is adequate for image of eccentricity 27 degrees. The optical design of the second preferred embodiment leads to a much greater depth of focus, as shown in FIG. 19. This means that in some embodiments the effective image blur is much less for a myopic defocus in the range of 2D to 5D, relative to the reflective optic, in accordance with the first and second simulations. The increased depth of focus is reflected in the MTF plots shown in FIG. 20, which may have a lesser dependence on the magnitude of myopic defocus relative to the reflective optic configuration, shown in FIGS. 3 and 4.

The third optical simulations show that the refractive optic may successfully project a peripheral retinal image with an acceptable image size and image magnification and depth of focus. Although the image size, magnification and depth of focus may be somewhat larger than for the reflective configuration of the second simulations.

Although MTF values at high spatial frequencies (50 lp/mm and above) are lower for this refractive optic design than the reflective design, image quality at high spatial frequencies can be somewhat is less relevant at the peripheral locations of the retinal image due to decreased visual acuity. The third simulations show that the focal length of the projection unit is 0.15 mm with an image size of 1100 microns and an image magnification is 110×. The Airy disk diameter is computed to be 36.7 microns, while the Raleigh criterion is 44.8 microns.

Referring again to FIGS. 11A and 11B, which shows a light guide, fourth simulations were conducted for this configuration comprising a light guide, a mirror and a lens. In the simulated embodiments, the focusing lens is located at the end (exit aperture) of the light pipe. In some embodiments, the light pipe comprises a curved lens surface on the end to focus light. In this lightguide embodiment, the projection optic comprises a light guide comprising a mirror and a lens.

In some embodiments, the light source 30 is placed in an outer portion of the contact lens 10, e.g. near the periphery, and light from the source is guided to a mirror that collects the light and deflects the light towards the eye 11 to generate an image in front of the peripheral retina 33 with a myopic defocus as described herein. In some embodiments, the function of the light guide is to increase the length of the light path, so as to reduce image magnification and increase resolution of the image formed anterior to the retina 33.

TABLE 5

Lens parameters used as inputs to the fourth simulations.

| Optics Property or Parameter | Value |
| --- | --- |
| Diameter of source | 10 microns |
| Wavelength of simulation | 510 nm |
| Length of Light Guide | 2.7 mm |
| Refractive index of material of projection optics | 2.2 |
| Diameter of mirror | 400 microns |
| Decenter of optic relative to center of contact lens | 1.75 mm |
| Thickness of optic | 290 microns |
| Image location | 25 degrees eccentric to fovea |
| Optical design and Image simulation | Aspheric $6^{th}$ order, Zernike $3^{rd}$ order |

Table 5 gives the properties of the projection system used in the fourth simulations of peripheral retinal image quality formed by light guide embodiments. Image magnification was 14 with an image size of 140 microns. These simulations reveal that the image magnification is acceptable, the depth of focus is not as large as the refractive optic, but larger than the reflective optic. The fourth simulations indicate that the focal length of the projection unit is 1.21 mm with an image size of 140 microns and a magnification of 14×. The Airy disk diameter is computed to be 34.8 microns, while the Raleigh criterion is 42.6 microns.

Figure 24:
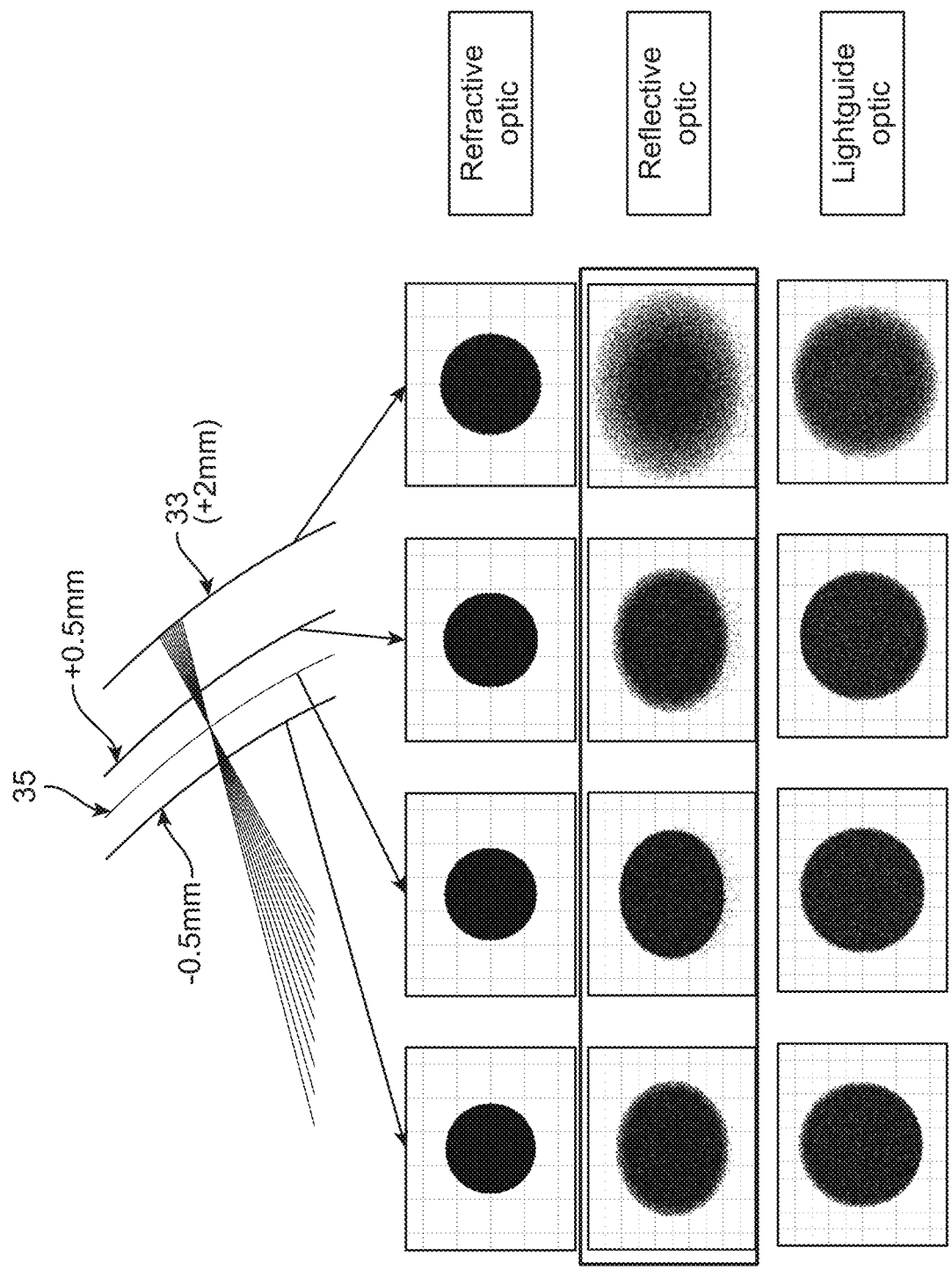
FIG. 24 shows a comparison of depths of focus of the peripheral images generated by the three projection systems, comprising a refractive optic, a reflective optic and a lightguide optic, in accordance with some embodiments.

The three results of the second, third and fourth simulations for the three corresponding configurations were compared with one another in terms of their size, the depth of focus produced by each defining a sharpness gradient of the defocused image as a function of magnitude of myopic defocus, and the beam diameter. The results show that the second simulations comprising the reflective optic has the best sharpness gradient, while the embodiment comprising the refractive optic has the smallest sharpness gradient, with the lightguide based projection unit providing a limited sharpness gradient, as shown in FIG. 24. Each of these approaches can be configured to decrease axial length growth in accordance with the teachings disclosed herein.

The three embodiments also differ considerably in terms of the diameter of the optic, as shown in Table 6.

TABLE 6

Optic diameters used in the three simulations.

| Configuration | Optic Diameter |
| --- | --- |
| Reflective optic | 1.1 mm |
| Refractive optic | 0.3 mm |
| Lightguide optic | 0.4 mm |

The reflective optic and light source 30 can be configured in many ways, and additional simulations can be conducted to determine appropriate configurations in accordance with the teachings disclosed herein. For example, clarity at the central object point shown in FIG. 14 can be disregarded because its contribution to the neurostimulation is likely to be limited. Such simulations and optimizations can allow a reduction of the diameter of the projection unit and its thickness, which can be helpful when the system is embedded into a contact lens 10 that provides a high level of comfort to wearers as described herein. The design input parameters for a fifth simulation are shown in Table 7.

TABLE 7

Input parameters for the fifth simulation.

| Lens parameter | Value |
| --- | --- |
| Diameter of light source | 10 microns |
| Wavelength | 507 nm |
| Diameter of reflective lens optic | 900 microns |
| Decenter of the light source from the center of the contact lens | 1.85 mm |
| Optic thickness | 200 microns |
| Thickness of projection unit, including light source | 200 microns |
| Location of peripheral retinal image | 27 degrees eccentric to fovea |
| Optic design | Aspheric $10^{th}$ order, Zernike polynomials, $4^{th}$ order |

Figure 25:
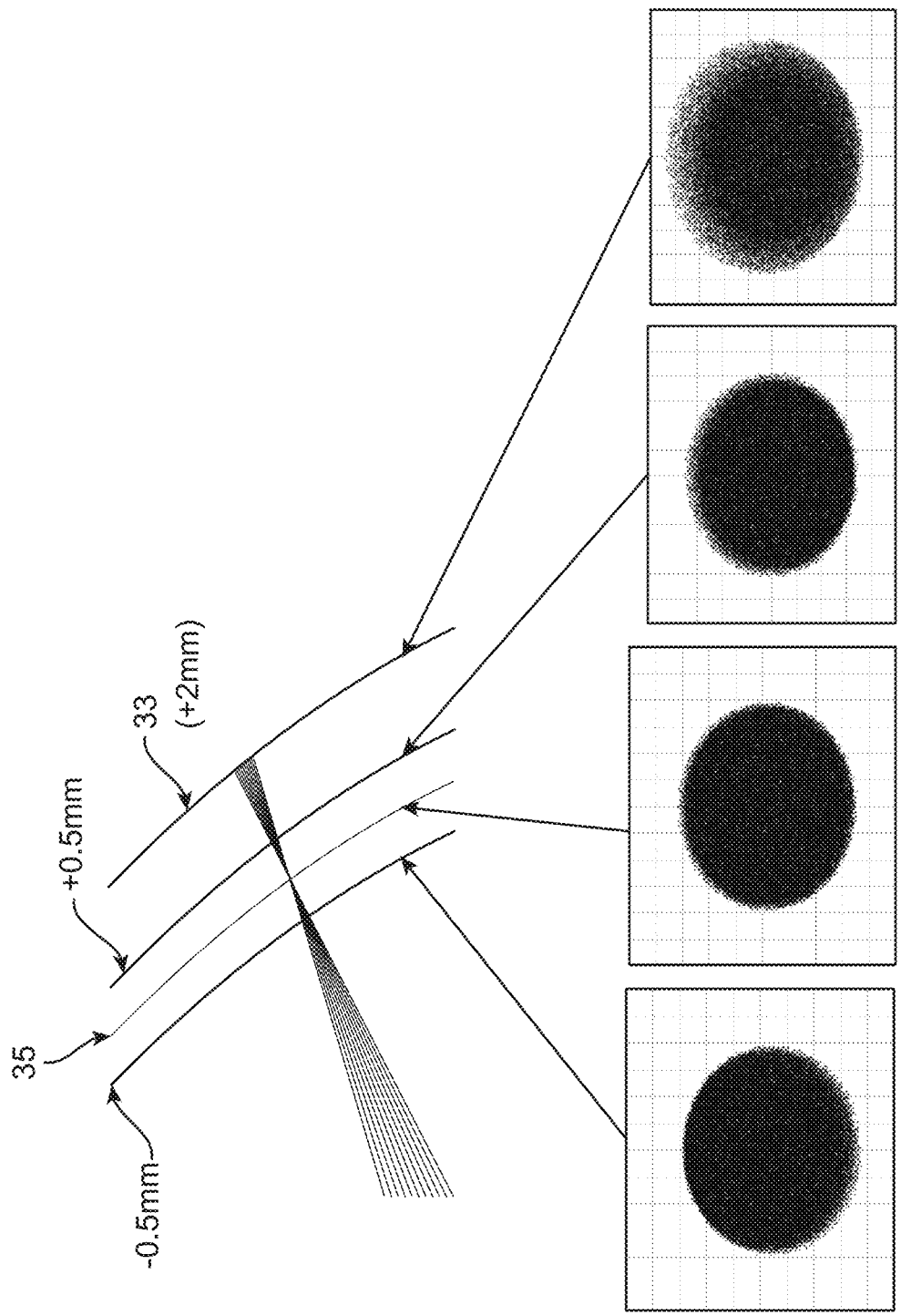
FIG. 25 shows depth of focus of the retinal image generated by a reflective optic design, in accordance with some embodiments
Figure 26:
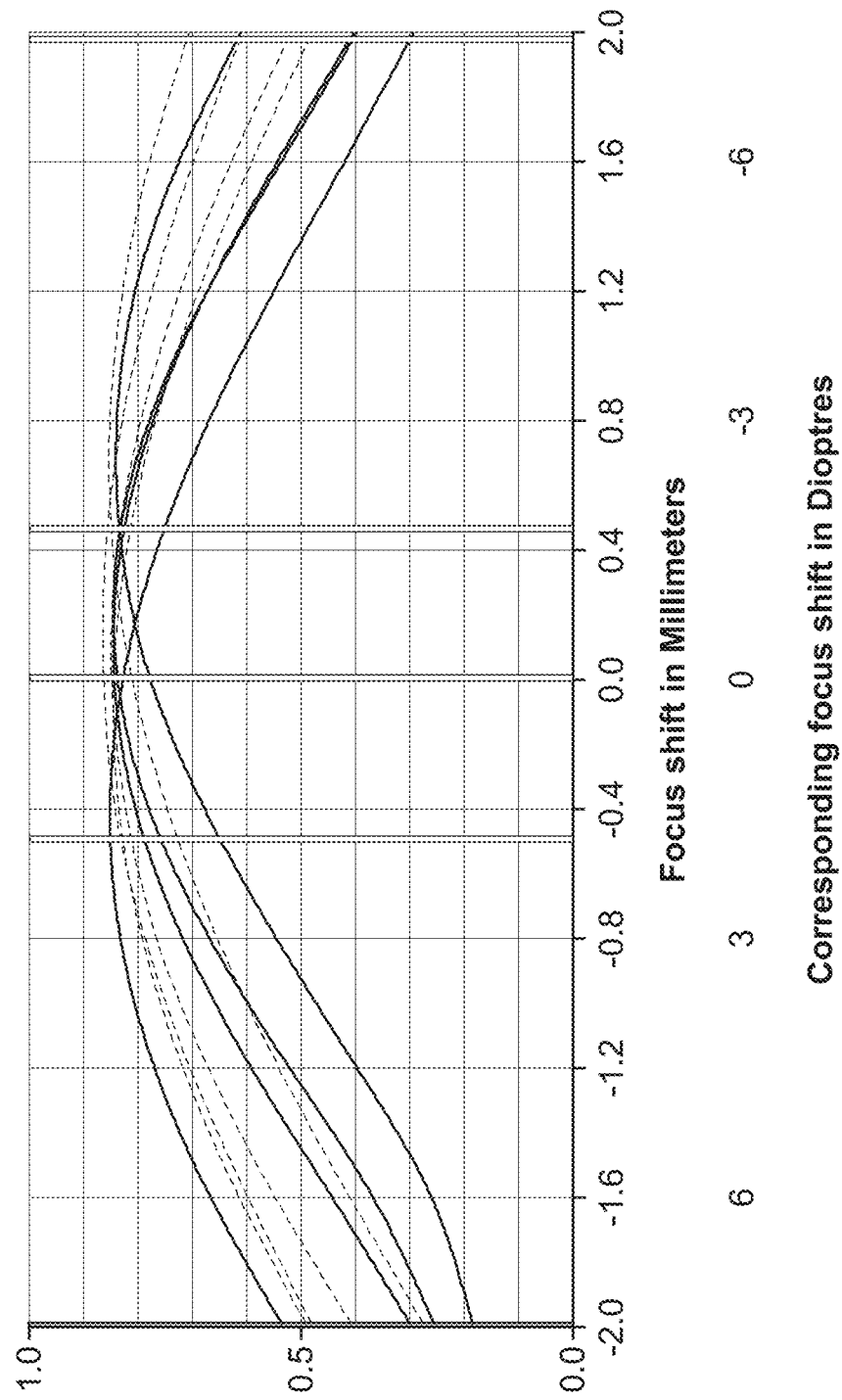
FIG. 26 shows MTF values at a single spatial frequency plotted against magnitude of myopic defocus for the peripheral image created by the reflective optic design of FIG. 25, in accordance with some embodiments.

The results show that the image magnification can be increased to 25, providing an image size of 250 microns for a 10 micron source, which is acceptable for a peripheral image anterior to the retina 33 in accordance with the embodiments disclosed herein. The output of these fourth image simulations is shown in FIGS. 25 and 26. The sharpness gradient, that is the variation of image spot size or MTF at a single spatial frequency as a function of magnitude of myopic defocus are still quite acceptable while providing a decreased size of the projection system.

As detailed herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

Each embodiment disclosed herein can be combined with any one or more of the other embodiments disclosed herein, and a person of ordinary skill in the art will recognize many such combinations as being within the scope of the present disclosure.

The present disclosure includes the following clauses.

Clause 1. A device to provide stimulation to a retina of an eye, comprising: one or more optics to project one or more images on the retina outside a fovea in order to promote one or more of a change in an axial length or a choroidal thickness of the eye.

Clause 2. The device of clause 1 wherein said one or more images comprises one or more of a still image or a dynamic image.

Clause 3. The device of clause 2, wherein the image comprises the dynamic image with a refresh rate within a range from 1 Hz to 200 Hz.

Clause 4. The device of clause 1, wherein the one or more images comprises one or more of monochromatic light or polychromatic light comprising a wavelength within a range from 400 nm to 800 nm.

Clause 5. The device of clause 1, wherein said image has information or content in the spatial frequency range of 1 cycle per degree to 60 cycles per degree and optionally from 1 cycle per degree to 10 cycles per degree, Clause 6. The device of clause 1, wherein said image comprises a contrast within a range from 99.9% to 2.5%.

Clause 7. The device of clause 1, wherein said image comprises an eccentricity with respect to a fovea within a range from 5, degrees to 40 degrees.

Clause 8. The device of clause 7, wherein said image illuminates the retina within the range with a pattern extending substantially continuously for 360 degrees around the fovea.

Clause 9. The device of clause 7, wherein said image illuminates a portion of the retina within the range.

Clause 10. The device of clause 1, further comprising circuitry to stimulate the retina with the one or more images with temporal illumination comprising one or more of continuous illumination, discontinuous illumination, periodic illumination or aperiodic illumination.

Clause 11. The device of clause 10, wherein the temporal illumination comprises the periodic illumination for a duration within a range from 1 second to 24 hours.

Clause 12. The device of clause 10, wherein the temporal illumination comprises the discontinuous illumination for a duration within a range from 1 second to 24 hours.

Clause 13. The device of clause 10, wherein said circuitry is configured to illuminate the retina when the subject is one or more of awake, asleep, or asleep or awake.

Clause 14. The device of clause 1, further comprising circuitry to stimulate the retina with the one or more images with a spatial illumination pattern comprising one or more of a continuous spatial illumination pattern, a discontinuous spatial illumination pattern, a periodic illumination pattern or an aperiodic spatial illumination pattern.

Clause 15. The device of clause 1, wherein said one or more images comprises a brightness within a range 1 to 1000 Trolands.

Clause 16. The device of clause 1, wherein said one or more optics is configured to project said one or more images with a luminance with in a range from 100 to 50,000 nits or within a range from 1 to 10,000 nits.

Clause 17. The device of clause 1, wherein said one or more images is corrected for a refractive error of the eye.

Clause 18. The device of clause 1, wherein said one or more images is defocused with respect to one or more locations of the retina where the one or more images illuminates the retina.

Clause 19. The device of clause 18 wherein said one or more images is myopically defocused within a range from 2.0D to 7.0D and optionally from 2.0D to 5.0D.

Clause 20. The device of clause 18, wherein said one or more images is hyperopically defocused by an amount within a range from 2.0D to 7.0D and optionally from 2.0D to 5.0D.

Clause 21. The device of clause 1, wherein said one or more optics comprises a component of a light projection system.

Clause 22. The device of clause 21, wherein the light projection system comprises a component of one or more of a projector, an ophthalmic device, a TV screen, a computer screen, a handheld, a mobile computing device, a tablet computing device, a smart phone, a wearable device, a spectacle lens, a near eye display, a head-mounted display, a goggle, a contact lens, an implantable device, a corneal onlay, a corneal inlay, a corneal prosthesis, or an intraocular lens.

Clause 23. The device of clause 21, further comprising a support coupled to the projection system, the support comprising one or more of an ophthalmic device, a TV screen, a computer screen, a handheld, a mobile computing device, a tablet computing device, a smart phone, a wearable device, a spectacle lens frame, a spectacle lens, a near eye display, a head-mounted display, a goggle, a contact lens, an implantable device, a corneal onlay, a corneal inlay, a corneal prosthesis, or an intraocular lens.

Clause 24. The device of clause 1, comprising: a plurality of light sources; wherein the one or more optics comprises a plurality of projection optics coupled to the plurality of light sources to project a plurality of images anterior to the retina.

Clause 25. The device of clause 24, wherein said plurality of projection optics is arranged to project the plurality of images of the plurality of light sources at a plurality of outer regions of the retina of the eye with an eccentricity within a range from 5 degrees to 30 degrees with respect to a fovea of the eye and optionally within a range from 15 degrees to 30 degrees.

Clause 26. The device of clause 24, wherein each of said plurality of projection optics is arranged to project an image myopically defocused with respect to a retinal surface, wherein an amount of said defocus is within a range from 2.0D to 7.0D and optionally within a range from 2.0D to 5.0D.

Clause 27. The device of clause 24, wherein each of said plurality of projection optics is located 1.5 mm to 5.0 mm from a center of a contact lens and optionally wherein the plurality of projection optics is located along the circumference of a circle.

Clause 28. The device of clause 24, wherein said plurality of projection optics comprises a plurality of image forming optics optically coupled to said plurality of light sources to project the plurality of images anterior to the surface of the retina.

Clause 29. The device of clause 28, wherein each of said plurality of light sources has a maximum distance across not exceeding 26 microns and optionally no more than 10 microns and optionally wherein said maximum distance across comprises a diameter.

Clause 30. The device of clause 28, wherein each of the plurality of projection optics comprises one or more of a mirror, a lens, or a lightguide.

Clause 31. The device of clause 30, wherein each of the plurality of image forming optics comprising one or more of a diffractive element, a Fresnel lens, or a compound Gabor lens.

Clause 32. The device of clause 30, wherein each of the plurality of image forming optics has a maximum distance across within a range from 200 microns to 1.5 mm and optionally wherein said maximum distance across comprises a diameter.

Clause 33. The device of clause 30, wherein each of the plurality of image forming optics is aspheric and corrected for image aberrations.

Clause 34. The device of clause 30, wherein each of the plurality of image forming optics comprises a combination of convex and concave mirrors.

Clause 35. The device of clause 33, wherein said each of the plurality of image forming optic forms an image anterior to an outer portion of the retina at an eccentricity within a range from 1 degree to 30 degrees from a fovea, optionally within a range from 10 degrees to 30 degrees from the fovea, optionally from 15 degrees to 30 degrees and further optionally from 25 degrees to 30 degrees.

Clause 36. The device of clause 33, wherein said each of the plurality of image forming optics creates an image anterior to the retina with an image of magnification within a range from 5 to 20 or within a range from 25 to 100.

Clause 37. The device of clause 24, wherein the image anterior to the outer portion of the retina comprises a magnitude of modulation transfer function of no less than 0.75 at a spatial frequency of 10 lp/mm, and no less than 0.40 at a spatial frequency of 30 lp/mm and optionally a magnitude of modulation transfer function of no less than 0.75 at a spatial frequency of 10 lp/mm, and no less than 0.40 at a spatial frequency of 50 lp/mm.

Clause 38. The device of clause 30, wherein each of the plurality of projection optics comprises an image forming optic comprising a collimating optic configured to form the image anterior to the retina.

Clause 39. The device of clause 30, wherein said projection optic comprises a single lens to function both as a collimating optic and an image forming optic.

Clause 40. The device of clause 30, wherein said projection optic comprises an image forming optic to create an image anterior to an outer portion of the retina with eccentricity no more than 30 degrees and a depth of focus of no more than 1.0D.

Clause 41. The device of clause 39, wherein said optic creates the image anterior to an outer portion of the retain with an eccentricity no more than 30 degrees, wherein a modulation transfer function of said image decreases by a minimum of 0.1 units for a defocus of 1.0D and optionally wherein the defocus of 1.0D comprises an incremental defocus.

Clause 42. The device of clause 24, wherein the plurality of light sources comprises a plurality of micro-displays.

Clause 43. The device of clause 24, wherein the plurality of light sources comprises a plurality of light emitting diodes (LEDs).

Clause 44. The device of clause 24, wherein each of said plurality of optical elements comprises a mirror assembly that collimates light emitted by a corresponding micro-display and directs a resulting light beam into the pupil of the eye, wherein said light beam is focused to form the peripheral image in front of the retina.

Clause 45. The device of clause 24, wherein each of said plurality of optical elements comprise a lens that receives light emitted by a corresponding micro-display and directs a resulting light beam into the pupil of the eye, wherein said light beam is focused to form an image in front of the retina.

Clause 46. The device of clause 24, wherein the plurality of light sources generates a polychromatic illumination and optionally wherein the plurality of light sources comprises a plurality of micro-displays generating polychromatic illumination.

Clause 47. The device of clause 24, wherein said image is about 0.5 mm to 2.0 mm in front of the retina.

Clause 48. The device of clause 24, wherein said image has a resolution of at least 10 lp/mm and optionally at least 30 lp/mm.

Clause 49. The device of clause 24, wherein said image has a magnification of no more than 200× and optionally no more than 100×.

Clause 50. The device of clause 24, wherein said image has a depth of focus no more than 2.5 diopters and optionally wherein said depth of focus is no more than about 0.9 mm.

Clause 51. The device of clause 24, wherein said image is projected at an eccentricity in the within a range from about 7.5 degrees to about 45 degrees and optionally within a range from about 15 degrees to about 45 degrees.

Clause 52. The device of clause 51, wherein said range is from about 15 degrees to about 30 degrees.

Clause 53. The device of clause 24, wherein said micro-display illuminates the pupil with an illuminance within a range from about 100 cd/m2 to 50,000 cd/m2. Or within a range from about 0.1 cd/m2 to 10 cd/m2

Clause 54. The device of clause 24, wherein the image is focused at a distance in front of the peripheral retina at a location and the image comprises a depth of focus and a spatial resolution, the depth of focus less than the distance, the spatial resolution greater than a spatial resolution of the peripheral retina at the location.

Clause 55. The device of clause 24, further comprising a sensor to receive input from the wearer when the contact lens has been placed on an eye of the wearer.

Clause 56. A spectacle lens comprising a display wherein said display projects images at the periphery of the retina in order to decrease progression of myopia.

Clause 57. The spectacle lens of clause 56, wherein said display comprises a micro-display.

Clause 58. The spectacle lens of clause 56, wherein said display comprises a pico-projector coupled to an eyeglass frame at a location corresponding to a temple of a wearer.

Clause 59. The spectacle lens of clause 56, wherein said display comprises a near eye display.

Clause 60. The spectacle lens of clause 56, wherein said display is configured to stimulate inwards growth of the retina.

Clause 61. The spectacle lens of clause 56, wherein said display comprises a micro-display and a micro-optic array.

Clause 62. The spectacle lens of clause 56, wherein said display enables clear viewing of the real world over a field of view in the range +/−2.0 degrees to +/−15 degrees and optionally within a range from about +/−2.0 degrees to +/−12.5 degrees.

Clause 63. The spectacle lens of clause 61, wherein said display projects images of light sources of said micro-display that are myopically defocused by an amount within a range from 2.0D to 7.0D and optionally within a range from 2.0D to 5.0D.

Clause 64. The spectacle lens of clause 56, wherein said display projects images at an outer region of the retina at an eccentricity to the foveola within a range from 15 degrees to 40 degrees, and optionally within a range from 20 degrees to 30 degrees.

Clause 65. The spectacle lens of clause 56, wherein said lens comprises a plurality of near eye displays in order to enable binocular stimulation of the outer retina.

Clause 66. The spectacle lens of clause 56, wherein said display transmits over 80% of light incident on it over a field of view not less than +/−5 degrees laterally and +/−7 degrees vertically and optionally not less than +/−12 degrees laterally and +/−20 degrees vertically.

Clause 67. The spectacle lens or device of any one of the preceding clauses, wherein the projected images move to compensate for eye movement and optionally wherein the projected images move to provide stimulation to overlapping regions of the periphery of the retina in response to eye movement.

Clause 68. The spectacle lens or device of any one of the preceding clauses, wherein the periphery of the retina comprises an outer location of the retina located away from the macula.

Clause 69. The device of any one of the preceding clauses, further comprising a processor coupled to the plurality of light sources to control illumination of the plurality of light sources.

Clause 70. The device of any one of the preceding clauses, further comprising wireless communication circuitry operatively coupled to the plurality of light sources to control illumination of the plurality of light sources.

Clause 71. The device of any one of the preceding clauses, further comprising wireless communication circuitry operatively coupled to a mobile device for the wearer to control illumination of the plurality of light sources.

Clause 72. The device of any one of the preceding clauses, further comprising wireless communication circuitry operatively coupled to a processor for a health care provider to program illumination cycles and intensities of the plurality of light sources.

Clause 73. The device of any one of the preceding clauses, wherein the device does not comprise a contact lens.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

We claim as follows:

1. A device to provide stimulation to a retina of an eye, comprising:
    one or more image forming optics; and
    one or more light sources coupled to the one or more image forming optics to generate and project one or more images on the retina outside a fovea in order to promote one or more of a change in an axial length or a choroidal thickness of the eye;
    wherein the one or more images comprises a plurality of images and wherein the one or more image forming optics comprises a plurality of projection optics coupled to a plurality of light sources to project the plurality of images anterior or posterior to the retina and each of said plurality of images has a depth of focus of no more than 2.5 Diopters.

2. The device of claim 1, wherein the one or more images comprises one or more of monochromatic light or polychromatic light comprising a wavelength within a range from 400 nm to 800 nm.

3. The device of claim 1, wherein said one or more images comprises a contrast within a range from 99.9% to 2.5%.

4. The device of claim 1, wherein said one or more images comprises an eccentricity with respect to the fovea within a range from 5 degrees to 40 degrees.

5. The device of claim 1, wherein said one or more image forming optics is configured to project said one or more images with a luminance within a range from 100 to 50,000 nits.

6. The device of claim 1, wherein said one or more images is corrected for a refractive error of the eye.

7. The device of claim 1, wherein said one or more images is myopically defocused within a range from 2.0 Diopters (D) to 7.0D.

8. The device of claim 1, wherein said one or more image forming optics comprises a component of a light projection system.

9. The device of claim 8, wherein the component of the light projection system comprises one or more of a projector, an ophthalmic device, a TV screen, a computer screen, a handheld, a mobile computing device, a tablet computing device, a smart phone, a wearable device, a spectacle lens, a near eye display, a head-mounted display, a goggle, a contact lens, an implantable device, a corneal onlay, a corneal inlay, a corneal prosthesis, or an intraocular lens.

10. The device of claim 1, wherein the one or more images comprises a plurality of images and wherein the one or more image forming optics comprises a plurality of projection optics coupled to a plurality of light sources to project the plurality of images anterior to the retina, wherein each of said plurality of projection optics is arranged to project an image myopically defocused with respect to a retinal surface and wherein an amount of defocus is within a range from 2.0 Diopters (D) to 7.0D.

11. The device of claim 1, wherein each of the plurality of projection optics comprises one or more of a mirror, a lens, or a lightguide.

12. The device of claim 1, wherein each of the plurality of images comprises a magnitude of modulation transfer function of no less than 0.75 at a spatial frequency of 10 line pairs/millimeters (lp/mm), and no less than 0.40 at a spatial frequency of 30 lp/mm.

13. The device of claim 1, wherein each of said plurality of projection optics comprises an image forming optic to create an image of the plurality of images anterior or posterior to an outer portion of the retina with eccentricity no more than 30 degrees and a depth of focus of no more than 1.0 Diopters (D).

14. The device of claim 1, wherein each of the plurality of projection optics comprises an image forming optic comprising a collimating optic configured to form an image of the plurality of images anterior or posterior to the retina, wherein each of said plurality of projection optics creates the image anterior or posterior to an outer portion of the retina with an eccentricity of no more than 30 degrees and wherein a modulation transfer function of said image decreases by a minimum of 0.1 units for a defocus of 1.0 Diopters (D).

15. The device of claim 1, wherein the plurality of light sources comprises a plurality of light emitting diodes (LEDs).

16. The device of claim 1, wherein each of said plurality of projection optics comprises a mirror assembly that collimates light emitted by a corresponding micro-display and directs a resulting light beam into a pupil of the eye and wherein said resulting light beam is focused to form an image of the plurality of images anterior or posterior to the retina.

17. The device of claim 1, wherein the plurality of light sources generates a polychromatic illumination.

18. The device of claim 1, wherein said plurality of light sources illuminates a pupil with an illuminance within a range from 100 candelas/meter2 (cd/m2) to 50,000 cd/m2.

19. The device of claim 1, wherein said device comprises one or more sensors, the sensors including one of a global positioning system sensor and a pulse oximeter.

* * * * *